(12) United States Patent
Reinhart et al.

(10) Patent No.: US 8,968,540 B2
(45) Date of Patent: *Mar. 3, 2015

(54) TRANS-BASE TUNNEL READER FOR SEQUENCING

(75) Inventors: Kevin Reinhart, Chandler, AZ (US); Stuart Lindsay, Phoenix, AZ (US); Peiming Zhang, Gilbert, AZ (US)

(73) Assignee: Arizona Board of Regents, a Body Corporate of the State of Arizona Acting for and on Behalf of Arizona State University, Scottsdale, AZ (US)

( * ) Notice: Subject to any disclaimer, the term of this patent is extended or adjusted under 35 U.S.C. 154(b) by 734 days.

This patent is subject to a terminal disclaimer.

(21) Appl. No.: 13/122,104
(22) PCT Filed: Oct. 6, 2009
(86) PCT No.: PCT/US2009/059693
§ 371 (c)(1),
(2), (4) Date: Jul. 9, 2011
(87) PCT Pub. No.: WO2010/042514
PCT Pub. Date: Apr. 15, 2010

(65) Prior Publication Data
US 2013/0186757 A1 Jul. 25, 2013

Related U.S. Application Data

(60) Provisional application No. 61/103,019, filed on Oct. 6, 2008.

(30) Foreign Application Priority Data

Mar. 18, 2009 (WO) .................. PCT/US09/037563
Mar. 18, 2009 (WO) .................. PCT/US09/037570

(51) Int. Cl.
*G01N 27/447* (2006.01)
*G01N 27/453* (2006.01)
(Continued)

(52) U.S. Cl.
CPC ........ *G01N 27/44791* (2013.01); *C12Q 1/6869* (2013.01); *G01N 33/48721* (2013.01); *G01N 27/447* (2013.01)
USPC .......................... 204/452; 204/603; 205/777.5

(58) Field of Classification Search
CPC .................... G01N 27/3278; G01N 33/48721; C12Q 2565/631
See application file for complete search history.

(56) References Cited

U.S. PATENT DOCUMENTS 6,537,755 B1 * 3/2003 Drmanac ..................... 435/6.11
(Continued)

FOREIGN PATENT DOCUMENTS

WO        03031464        4/2003
WO    WO 2007/084163    7/2007
(Continued)

OTHER PUBLICATIONS

Loakes et al., "5-Nitroindole as an universal base analogue," Nucleic Acids Research, 1994, vol. 22, No. 20, pp. 4039-4043.*
(Continued)

*Primary Examiner* — Alex Noguerola
(74) *Attorney, Agent, or Firm* — Cooley LLP

(57) ABSTRACT

A device for reading the sequence of a polymer, consisting of a first electrode and a second electrode, each electrode being functionalized with a reader molecule strongly bonded to the electrodes, but forming weak bonds with a molecule to be sequenced. In particular, the reader molecule is designed to form bonds with at least two points on the target molecule such that the target molecule is trapped between a first reader molecule on one electrode and a second reader molecule on the second electrode, with the overall size of the molecular complex being small enough to permit significant electric current to flow.

14 Claims, 68 Drawing Sheets

(51) Int. Cl.
*G01N 27/327* (2006.01)
*C12Q 1/68* (2006.01)
*G01N 33/487* (2006.01)

(56) References Cited

U.S. PATENT DOCUMENTS

| | | | |
|---|---|---|---|
| 6,627,067 B1 | 9/2003 | Branton et al. | |
| 6,821,730 B2 | 11/2004 | Hannah | |
| 8,003,319 B2 | 8/2011 | Polonsky et al. | |
| 8,628,649 B2* | 1/2014 | Lindsay et al. | 204/452 |
| 2002/0033345 A1 | 3/2002 | Meade | |
| 2002/0117659 A1 | 8/2002 | Lieber et al. | |
| 2003/0148289 A1 | 8/2003 | Sundararajan et al. | |
| 2003/0215376 A1 | 11/2003 | Chopra | |
| 2004/0144658 A1 | 7/2004 | Flory | |
| 2004/0262636 A1 | 12/2004 | Yang et al. | |
| 2005/0202444 A1 | 9/2005 | Zhu | |
| 2006/0194228 A1 | 8/2006 | Rakitin et al. | |
| 2006/0211016 A1 | 9/2006 | Kayyem et al. | |
| 2006/0263255 A1 | 11/2006 | Han et al. | |
| 2007/0009379 A1 | 1/2007 | Bau et al. | |
| 2008/0121534 A1 | 5/2008 | White et al. | |
| 2008/0171316 A1 | 7/2008 | Golovchenko et al. | |
| 2009/0198117 A1 | 8/2009 | Cooper et al. | |
| 2010/0084276 A1 | 4/2010 | Lindsay | |

FOREIGN PATENT DOCUMENTS

| | | |
|---|---|---|
| WO | WO-2008124706 A2 | 10/2008 |
| WO | WO 2009/117522 | 9/2009 |
| WO | WO-2009117517 A2 | 9/2009 |
| WO | WO 2010/042514 | 4/2010 |

OTHER PUBLICATIONS

Meunier et al. "Enhancement of the Transverse Conductance in DNA Nucleotides", The Journal of Chemical Physics 128, 0411003, Jan. 29, 2008.
International Search Report of PCT/US09/59693 dated Dec. 17, 2009.
T. Ito, L. Sun, R. M. Crooks, Chemical Communications, 1482 (2003).
R. Fan et al., Nano Letters 5, 1633 (Sep. 2005).
J. He, L. Lin, P. Zhang, S. Lindsay, Identification of DNA base-pairing via tunnel current decay. Nano Letters 7 (12), 3854-3858, 2007.
Clark et al., Nature Nanotechnology, 2009. 4:265-270.
Doronina, S. O. and J.-P. Behr, Towards a general triple helix mediated DNA recognition scheme. Chemical Society Reviews, 1997. 26: p. 63-71.
Fox, K.R. and T. Brown, An extra dimension in nucleic acid sequence recognition. Quarterly Reviews of Biophysics, 2005. 38: p. 311-320.
International Prelimainary Report on Patentability & Written Opinion PCT/US2009/059693 dated Apr. 12, 2011 (7-pages).
International Search Report and Written Opinion for International Application No. PCT/US2009/037570, mailed Jan. 25, 2010, 9 pages.
International Preliminary Report on Patentability for International Application No. PCT/US2009/037570, dated Sep. 21, 2010, 5 pages.
International Search Report and Written Opinion for International Application No. PCT/US2009/037563, mailed Nov. 2, 2009, 8 pages.
He, H. et al., "Functionalized nanopore-embedded electrodes for rapid DNA sequencing," The Journal of Physical Chemistry C Letters, 112:3456-3459 (2008).
"Base Pair," Wikipedia, downloaded on Nov. 28, 2012, 4 pages.
Ito, T. et al., "Observation of DNA transport through a single carbon nanotube channel using fluorescence microscopy," The Royal Society of Chemistry, 2003:1482-1483 (2003).
Ohshiro, T. et al., "Complementary base-pair-facilitated electron tunneling for electrically pinpointing complementary nucleobases," Proc. Nat. Acad. Sci. (USA), 103(1):10-14 (Jan. 3, 2006).
Porath, D. et al., "Direct measurement of electrical transport through DNA molecules," Nature, 403:635-638 (Feb. 10, 2000).
Shimmin, R. G. et al., "Polymer size and concentration effects on the size of gold nanoparticles capped by polymeric thiols," Langmuir, 20(13): 5613-5620 (2004).
Schug, K. A. et al., "Noncovalent binding between guanidinium and anionic groups: Focus on biological-and synthetic-based arginine/guanidinium interactions with phosph[on]ate and sulf[on]ate residues," Chemical Reviews, 105(1):67-113 (2005).
Lee, M. et al., "GC base sequence recognition modified by oligo (imidazolecarboxamide) and C-terminus-modified analogues of distamycin deduced from circular dichroism, proton nuclear magnetic resonance, and methidiumpropylethylenediaminetetraacetate4on(II) foolprinting studies," Biochemistry, 32(16):4237-4245 (1993).
Walti, C. et al., "Direct selective functionalization of nanometer-separated gold electrodes with DNA oligonucleotides," Langmuir, 19(4):981-984 (2003).
Peng, H. et al., "Slowing down DNA translocation using magnetic and optical tweezers," American Physical Society, APS March Meeting, Mar. 13-17, 2006, Abstract #N26.010. Available online at URL: http:/meetings.aps.org/MeetinwMAR06/Event142679, 1 page.

* cited by examiner

Grow Oxide on Si Substrate

Grow Nanotube

Deposit Pd

Deposit SiN

Etch Back

Functionalize with COOH Group

Etch Window on Back Side

Functionalize – COOH With Guanidinium

Attach Nucleotide to Guanidinium

Add Contact Nanotube

Add Passivation Layer

Add Ring-shaped Pd Connecting Layer

Top View of FIG.2L After Removal of Passivation Layer of removal of sacrificial nucleotide

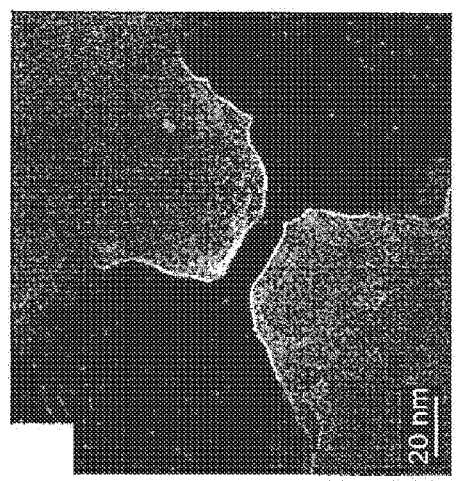
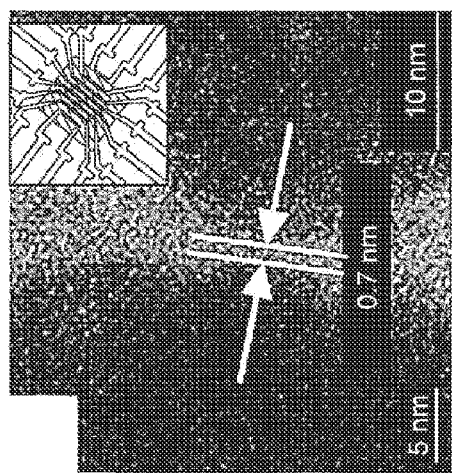
FIG. 6A
FIG. 6B

View into trench

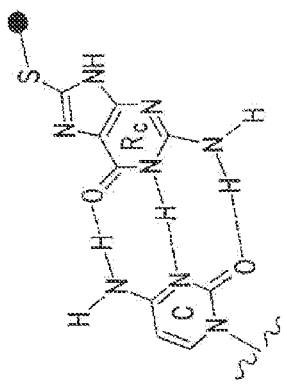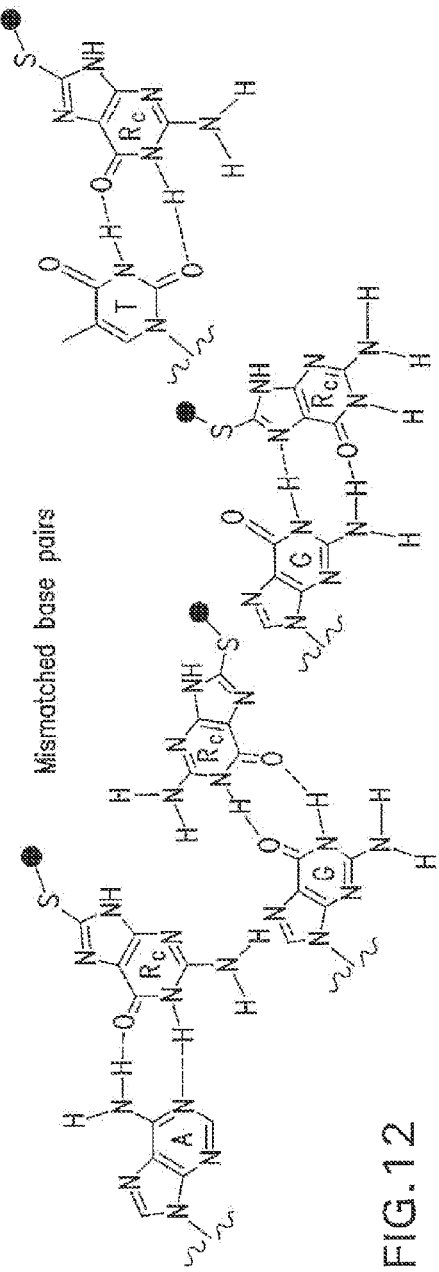
FIG. 12

Thymine Reader: 2,6-amino-8-mercaptopurine($R_T$)
The Watson-Crick base pair
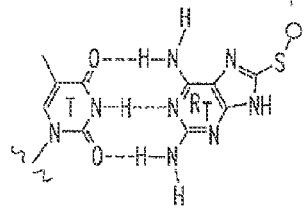
Mismatched base pairs
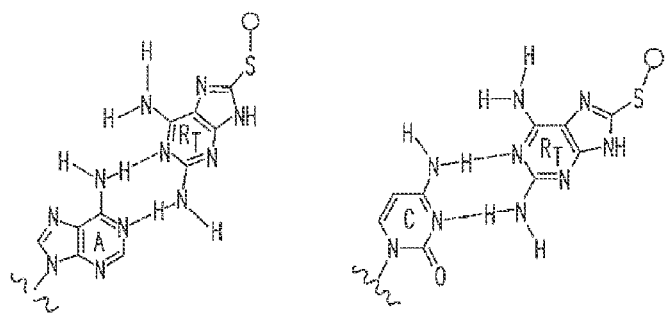
Analogues of 2-diaminoadenine
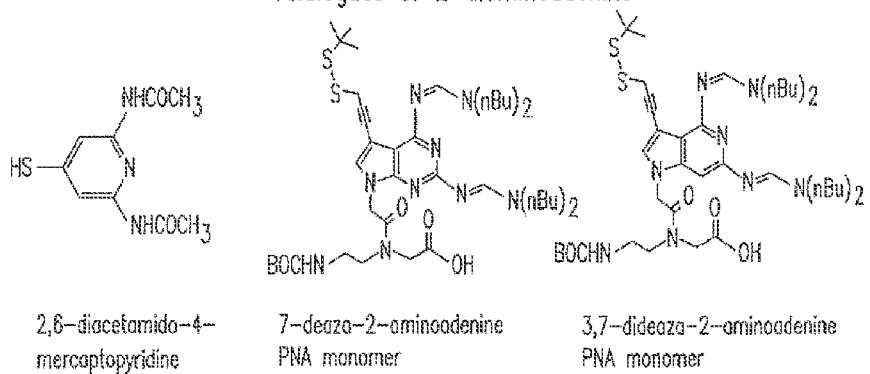
2,6-diacetamido-4-mercaptopyridine
7-deaza-2-aminoadenine PNA monomer
3,7-dideaza-2-aminoadenine PNA monomer
FIG.16

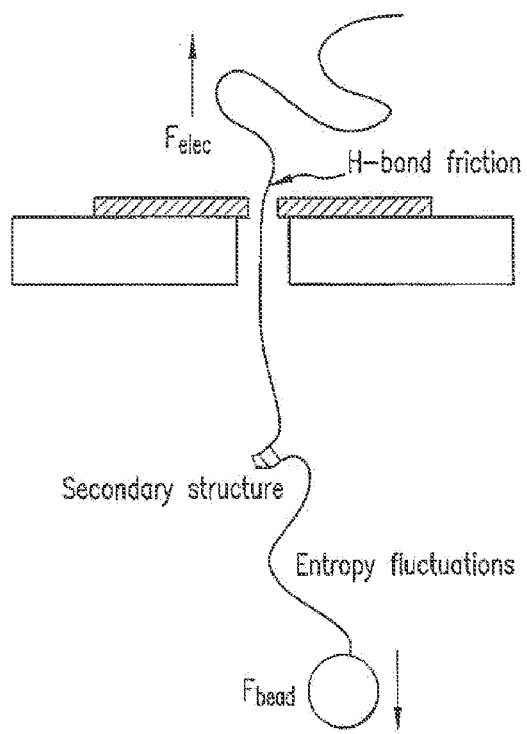
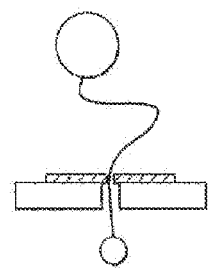
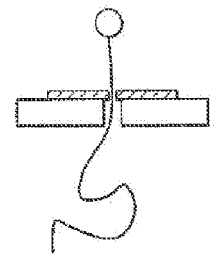
FIG.19A
FIG.19B
FIG.19C

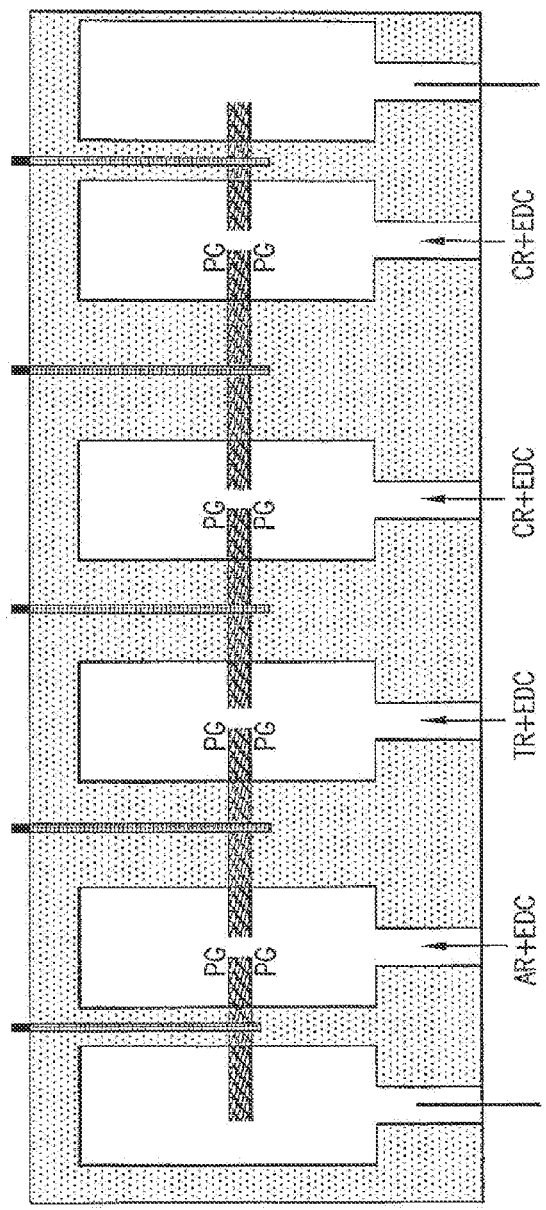

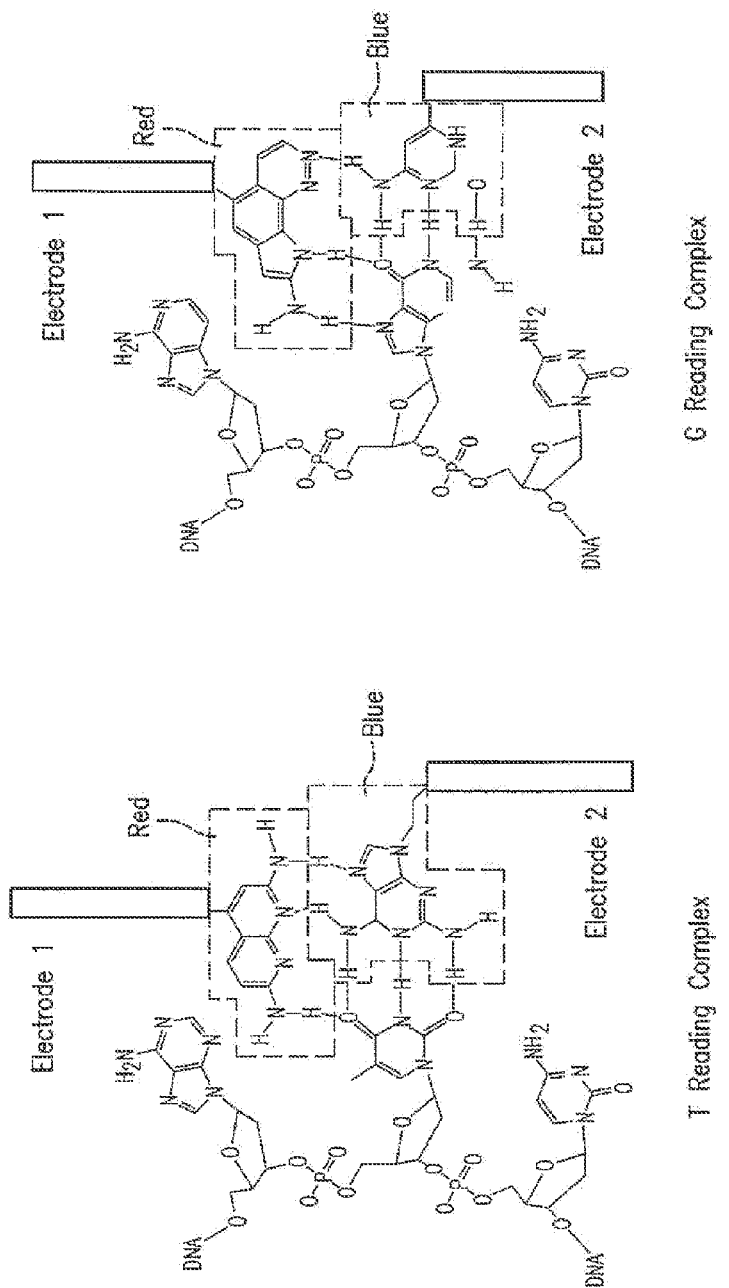

Reagents and conditions: (a) I₂, H₅IO₆ in acetic acid with H₂O (7%) and concentrated H₂SO₄ (0.1%); (b) Propargyl S-thiobenzoate (2.5 eq), Pd(PPh₃)₄ (0.1 eq), CuI (0.2 eq), Et₃N (1.0 eq.) in DMF, heating by microwave.

Scheme 1: Incorporation of the propargyl S-thiobenzoate linker into [1,8]Napthyridine-2,7-diamine

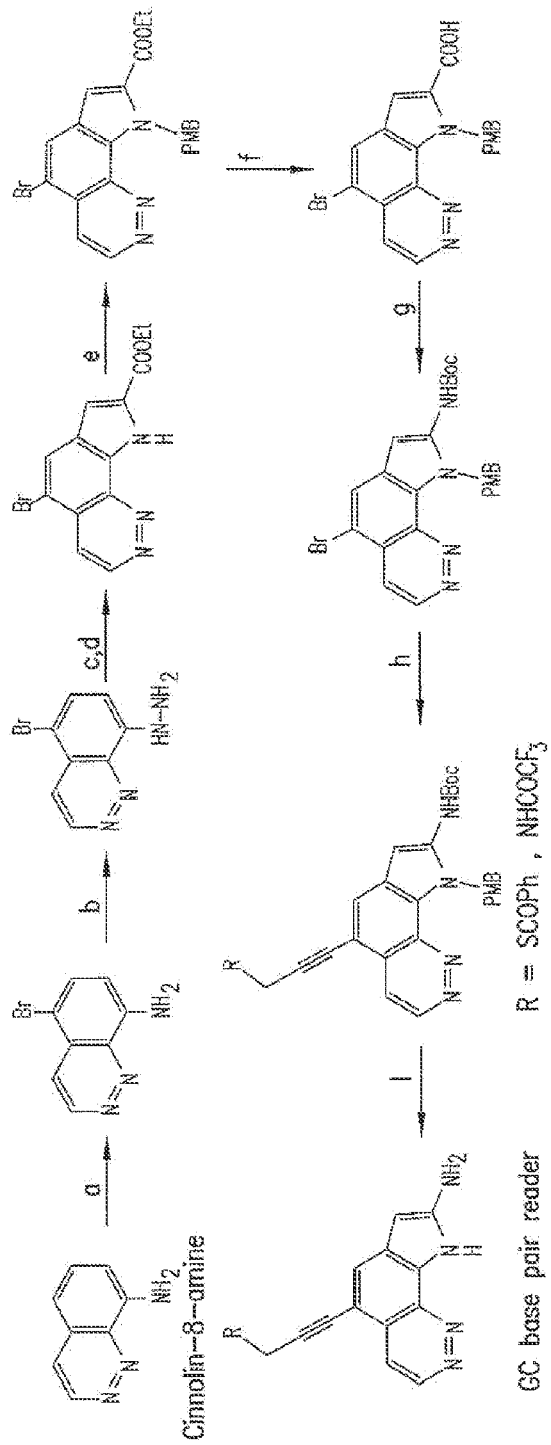

FIG. 41

Scheme1: Synthetic route to the GC trans-base-pair reader

Reagents and conditions: (a) dibromodimethylhydantoin, DCM, −0 °C; (b) SnCl₂, aq. HCl; (c) ethyl pyruvate, EtOH, AcOH; (d) ZnCl₂, AcOH; (e) NaH, DMF, 4-methoxybenzyl (PMB) chloride; (f) NaOH, THF, EtOH, then aq. HCl; (g) NaN₃, Boc₂O, 1,2-dimethoxyethane (DME); (h) propargyl S-thiobenzoate or N-propargyltrifluoroacetamide, Pd(PPh₃)₄, CuI, Et₃N; (i) trifluoroacetic acid, 1,2-dichloroethane.

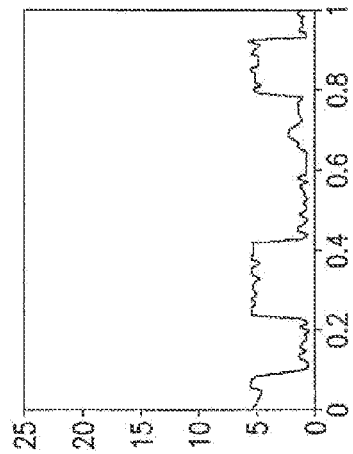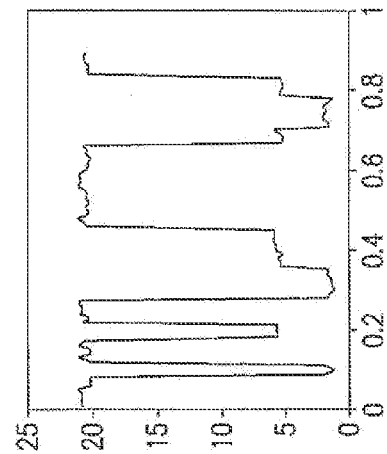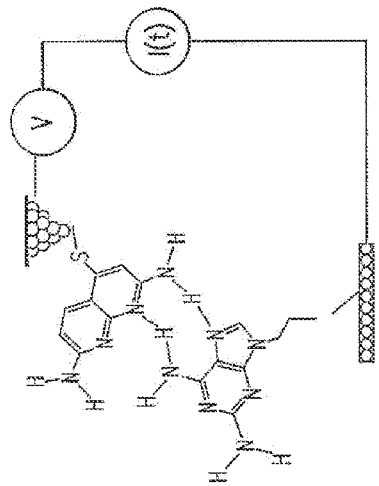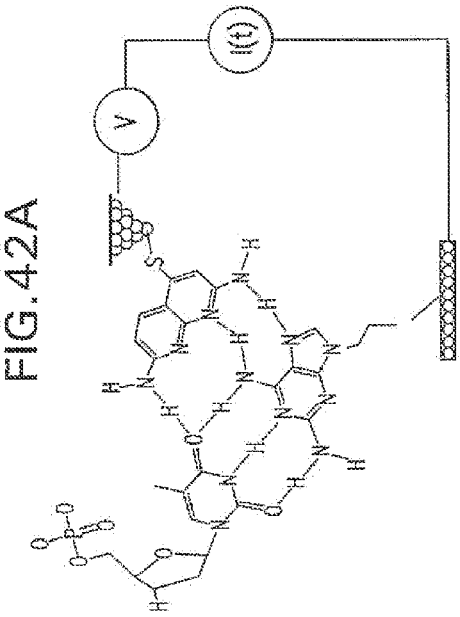

2

1

TRANS-BASE TUNNEL READER FOR SEQUENCING

CROSS REFERENCE TO RELATED APPLICATIONS

This application is a §371 National Stage Application of PCT/US2009/059693 filed Oct. 6, 2009 which claims priority to U.S. provisional application 61/103,019, filed on Oct. 6, 2008 and PCT application, PCT/US2009/037563, filed on Mar. 18, 2009, and PCT/US2009/37570, filed on Mar. 18, 2009.

GOVERNMENT RIGHTS

This invention was made with government support under NHGRI Grant No. 1R21 HG004378-01 and 5R21 HG004378-02 awarded by the National Institute of Health. The government has certain rights in the invention.

FIELD OF THE INVENTION

The present invention is directed to systems, devices and methods for identifying biopolymers, such as strands of DNA, as they pass through a constriction such as a carbon nanotube nanopore. More particularly, the invention is directed to such systems, devices and methods in which a newly translocated portion of the biopolymer forms a transient electrical circuit between the nanotube nanopore and a second electrode, which may also be a nanotube. Further, the invention is directed to such systems, devices and methods in which the constriction is provided with a functionalized unit which, together with a newly translocated portion of the biopolymer, forms a temporary electrical circuit that can be used to characterize that portion of the biopolymer.

BACKGROUND OF THE INVENTION

Several approaches have been employed or proposed to perform DNA sequencing. Among the various approaches, the nanopore approach has the great advantage of only allowing one base to pass a particular point at a time (if the orifice is small enough). It can also be highly precessive (moving from one base to the next without "stuttering") if the driving force is high enough.

Nanotubes have been considered as one way to implement a nanopore. For instance, the use of carbon nanotubes as nanopores through which DNA may be translocated electrophoretically has been described in T. Ito, L. Sun, R. M. Crooks, Chemical Communications, 1482 (2003) (Ref 1). Silica nanotubes have also been used as nanopores, as reported in R. Fan et al., Nano Letters 5, 1633 (September, 2005). A new approach for reading the sequence of a DNA molecule passing between electrodes on a nanopore using hydrogen bond-mediated tunneling signals has been proposed in J. He, L. Lin, P. Zhang, S. Lindsay, Identification of DNA base-pairing via tunnel current decay. Nano Letters 7 (12), 3854-3858, 2007. U.S. Pat. No. 6,821,730 discloses the use of carbon nanotube probes to sequence DNA. U.S. Pat. No. 6,627,067 discloses a method of translocating molecules through nanopores for sequencing purposes.

The aforementioned articles and patents are incorporated by reference to the extent necessary to understand the present invention.

SUMMARY

In one aspect, the present invention is directed to a readout device and scheme for DNA sequencing through a constriction, such as a nanopore. The device is adapted so that a DNA strand can translocate through the nanopore of a first nanotube ("translocating nanotube"). As the DNA strand emerges from the translocating nanotube, a portion of the strand completes a temporary electrical circuit between the translocating nanotube and a second electrode, which may comprise a nanotube ("contact nanotube"). The electrical circuit utilizes the electron tunneling current mediated by specific hydrogen-bonding molecular recognition events between portions of the DNA strand and functionalized entities attached to the two nanotubes.

The scheme utilizes the electron tunneling current mediated by specific hydrogen-bonding molecular recognition events.

In another aspect, the present invention is directed to the design and construction of a manufacturable instrument, constructed so as to allow for parallel operation of many constrictions for performing sequencing, such as of ssDNA or dsDNA.

The system employs at least one device having at least two sensing electrodes spaced apart by a gap and positions on either side of a constriction, such as a nanopore. The nanopore electrode gap construction may be achieved by electrochemical assembly to produce gaps that are reformable in-situ. Alignment of a nanogap sensing electrode pair with a constriction is achieved by means of novel 'though-pore' plating process. Thereafter, active gap control may be used to dynamically-control the gap. Since the natural DNA bases frequently form mismatched base pairs, custom recognition elements (referred to herein as "affinity elements") are used for molecular recognition. Each constriction is functionalized with at least one such custom affinity element. Electrophoresis, magnetic bead technology and the signal from the pore itself can be used to effect translocation through the constriction and characterization of the molecule. The system is thus configured to acquire data related to the locations of specific bases in a single strand of DNA.

In the device, a pair of spaced apart sensing electrodes border on the constriction. The first sensing electrode is connected to a first affinity element (e.g., a phosphate grabber when the target molecule is ssDNA) while the second sensing electrode is connected to a second affinity element. Each affinity element may be connected to its corresponding electrode via one or more intermediary moieties, such as a molecular linker, which itself typically is connected to the electrode via an electrode anchoring group, such as a thiol. The first and second affinity elements are configured to temporarily form hydrogen bonds with first and second portions of the molecule as the latter passes through the constriction. During translocation, the electrodes, affinity elements and first and second portions of the target molecule complete an electrical circuit and allow a measurable electrical current to pass between the first and second electrodes. The time-varying nature of this electrical current, and the specific affinity elements employed, allow one to characterize the first and second portions of the target molecule.

The present invention's approach to nanopore electrode construction is directed to mimicking the scanning tunneling microscopy that has proved effective and successful in experiments with hydrogen-bond-based electronic recognition. Three elements of this are: 1) self-aligned metal-gap-metal junctions capable of being reformed in-situ; 2) active control of the tunnel gap; and 3) manufacturability. The metal used in these junctions can be gold. Trials with gold electrodes have indicated that the "blinking" of contacts made to soft metals is not a significant problem.

The present invention further provides an embodiment where the first recognition element comprises a base reader as discussed above and the second recognition element comprises a base pair reader instead of phosphate grabber. This provides a new method for forming chemically-specific chemical contacts to single stranded DNA, by forming self-assembled hydrogen bonded contacts across each base. Preferred G-C/C-G base pair readers include, but are not limited to cinnoline derivatives described herein. Preferred A-T/T-A base pair readers include, but are not limited to 1,8-napthyridine derivatives and 1,10-phenanthroline derivatives described herein.

The present invention provides a device for characterizing a biopolymer. The device has a carbon nanotube with an interior channel through which the biopolymer is translocated. Preferably the translocation is driven by electrophoresis. The carbon nanotube comprises a plurality of gaps cut into the carbon nanotube. Each of the plurality of gaps is functionalized to provide a characteristic signal at each of the plurality of gaps. Preferably the biopolymer is a nucleic acid such as DNA or RNA and the carbon nanotube comprises four gaps cut into the carbon nanotube, wherein each gap is functionalized with a different base reader.

The present invention also provides a device for determining the sequence of a nucleic acid comprising: a) a solid surface to support a carbon nanotube having an interior channel through which the nucleic acid can travel; and b) an insulating film layer disposed on top of the carbon nanotube.

The insulating film layer is preferably PMMA. The film layer comprises an origination, a first, a second, a third, a fourth and a termination well capable of containing an electrolyte. The origination well is proximal to the first, second, third, fourth and termination wells, and the termination well is distal to the first, second, third, fourth and origination wells.

The carbon nanotube comprises a first, second, third and fourth gap cut into the carbon nanotube and each of the gaps contact a separate well. For example, the first gap contacts the first well, the second gap contacts the second well, the third gap contacts the third well and the fourth gap contacts the fourth well.

Each of the gaps of the carbon nanotube has a first gap end and a second gap end; and each of the first gap ends is functionalized with a first recognition element, and each of the second gap ends is functionalized with a second recognition element.

The carbon nanotube has an origination end contacting the origination well and a termination end contacting the termination well, and an origination electrode contacts the origination well and a termination electrode contacts the termination well. The origination and termination electrodes do not contact the carbon nanotube.

The device further comprises a first electrode contacting the carbon nanotube between the origination well and the first well; a second electrode contacting the carbon nanotube between the first and second well; a third electrode contacting the carbon nanotube between the second and third well; a fourth electrode contacting the carbon nanotube between the third and fourth well; and a fifth electrode contacting the carbon nanotube located between the fourth and termination well;

In certain embodiments, the solid surface comprises an oxidized silicon wafer and the carbon nanotube is grown directly on the silicon wafer.

In certain embodiments the nucleic acid is DNA or RNA and the first recognition element comprises a phosphate grabber such as guanidinium and the second recognition element comprises a nucleobase reader, such as a nucleobase reader that specifically recognizes its Watson-Crick base pair complement.

The present invention also provides a method of making devices of the present invention. A carbon nanotube is grown on a silicon wafer. A plurality of electrodes are deposited on the silicon wafer and contact the carbon nanotube. A plurality of electrodes are deposited on the silicon wafer that do not contact the carbon nanotube. A plurality of gaps having a first and second gap end are cut into the carbon nanotube. Each gap is cut so that it is located between two of the plurality of electrodes that contact the carbon nanotube. First and second recognition elements are conjugated to each of the plurality of first gap ends and second gap ends, respectively.

The present invention also provides a method of detecting a tunnel current signal that switches between two levels, which is characteristic of an interaction with a single base, and wherein said signal is used to identify the target base in the tunnel gap. The present invention also provides a method of identifying a target base in a tunnel gap by detecting a tunnel-current signal that switches between two levels, wherein the signal switch is characteristic of an interaction with a single base.

The present invention also provides a molecular recognition chip configured to identify at least one portion of a target molecule, the chip comprising:

a substrate; a first nanotube passing through at least a portion of the substrate, the first nanotube provided with a nanopore and configured and dimensioned to permit the translocation of a target molecule therethrough; a second nanotube supported by the substrate and disposed in a fixed relationship with respect to said first nanotube so as to form a first gap with the first nanotube; and an electrical circuit configured to detect an electrical current between the first and second nanotubes, upon passage of the target molecule past said gap, wherein: the first nanotube comprises a first recognition element connected to an end thereat and the second nanotube comprises a second recognition element connected to a first end thereof, and wherein the first and second recognition elements comprise a universal base reader.

The invention also provides a device for obtaining an electrical signal characteristic of a DNA base pair comprising a first universal base reader attached to a first electrode and a second universal base reader attached to a second electrode, wherein the universal base readers are capable of recognizing different DNA bases and are also capable of forming an additional set of hydrogen bonds with a complex of a DNA base and the universal base reader, and wherein the universal base readers comprise a conjugate of a planar $\pi$ system with a functional group, amine, amide, nitro, carboxylic acid, and halogen, connected to a molecular linker.

The invention also provides a device for obtaining an electrical signal characteristic of a DNA base pair comprising a universal base reader attached to a first electrode and a universal base reader attached to a second electrode, wherein the universal base reader is capable of recognizing different DNA bases (including methylated DNA bases) and is also capable of forming an additional set of hydrogen bonds with a complex of a DNA base and the universal base reader. In certain embodiments, the universal base reader comprises 1H-imidazole-2-carboxamide containing a molecular tether, such as 2-aminoethyl or mercaptomethyl, at its 4 position.

The present invention also provides a method of sequencing DNA as the DNA molecule translocates through a constriction, the method comprising: a) providing an apparatus comprising a DNA sequencing device in accordance with claim 2, the device being located in the apparatus such that a first chamber is located on the first side of the device and a second chamber is located on the second side of the device; b) introducing the DNA molecule into the second chamber; c) electrophoresing the DNA molecule so that it translocates through the constriction; and d) detecting an electrical current passing through the first electrode, a first universal base reader, a nucleo base of the DNA molecule, a second universal base reader, and the second electrode.

The present invention also provides a composition comprising a universal base reader wherein the reader is selected from the group consisting of 5-(2-aminoethyl)-1H-imidazole-2-carboxamide.

The present invention also provides a method of synthesizing the universal base readers.

BRIEF DESCRIPTION OF THE DRAWINGS

For a better understanding of the present invention and to show how the same may be carried out in practice, reference will now be made to the accompanying drawings.

FIG. 6A-6B: FIG. 6A shows a high-resolution imaging of a prior art nanogap. FIG. 6B shows a prior art nanogap sculpted by e-beam ablation (from Fischbein and Drndić, 2006 and 2007).

FIG. 7A shows a schematic layout, including a covering layer of $SiO_2$. FIG. 7C shows a cross section of gap.

FIG. 7B shows a SEM image of a real device with another view into the nanogap shown in FIG. 7D.

(FIG. 8A) i-v plots for tunnel devices (as-made) similar to that shown in FIG. 7. (FIG. 8B) Current vs. time after closing the gaps electrochemically and then stripping them open. Quantum-conductance steps (indicated by arrows) are clearly observed as Au is removed.

FIG. 12. Base pairing of the cytosine reader ($R_C$) with natural DNA bases.

FIG. 16. Base pairing of DAP with DNA bases and proposed analogues of DAP as candidates for the T reader.

FIG. 19A-19C: (a) Forces on a molecule with bead stretching and electrophoretic translocation. (b) Bead arrangement for 'flossing' experiment. (c) Magnetic force added to electrophoretic force.

FIG. 33: Functionalization of the remaining side of the readers with the adenine reader (AR), thymine reader (TR), cytosine reader (CR) and guanine reader (GR).

FIG. 41 provides Scheme 2 to synthesize a base-pair reader.

FIG. 42 Telegraph noise measurements on trans-base-pair readers. (A) Without target and (B) simulated current-time signal. (C) After capture of a thymine nucleotide with (D) simulated signal.

FIG. 59(a) shows the tunnel current in pure solvent and FIG. 59(b) shows tunnel current after the addition of 500 nM Guanidine. The inset shows a blow up of a typical peak—the residence times are typically 0.5 to 1 ms.

DETAILED DESCRIPTION OF THE INVENTION

The present invention relates to nanopore based DNA sequencing. Such system utilized the concept of sequence by recognition: use of hydrogen-bond mediated chemical recognition to transduce an electrical signal for a recognized base. See PCT/US08/59602, filed Apr. 7, 2008, which is herein incorporated by reference. In addition to sequence by recognition, the present inventors have developed additional inventions which are described and claimed herein, namely, a trans-base tanner reader for sequencing, the use of single-walled carbon nanotubes (SWCNTs) as nanopores, and the integration of the electrode system into the SWCNT itself, which simplifies the manufacture of the reader. Described herein are various devices of the invention, methods of making those devices, recognition elements (such as phosphate grabbers, base readers and base-pair readers) useful in the devices and various experiments performed to show the feasibility of using such devices.

Device Utilizing a Translocation Nanotube and a Contact Nanotube for Tunneling Current Formation.

Figure 1:
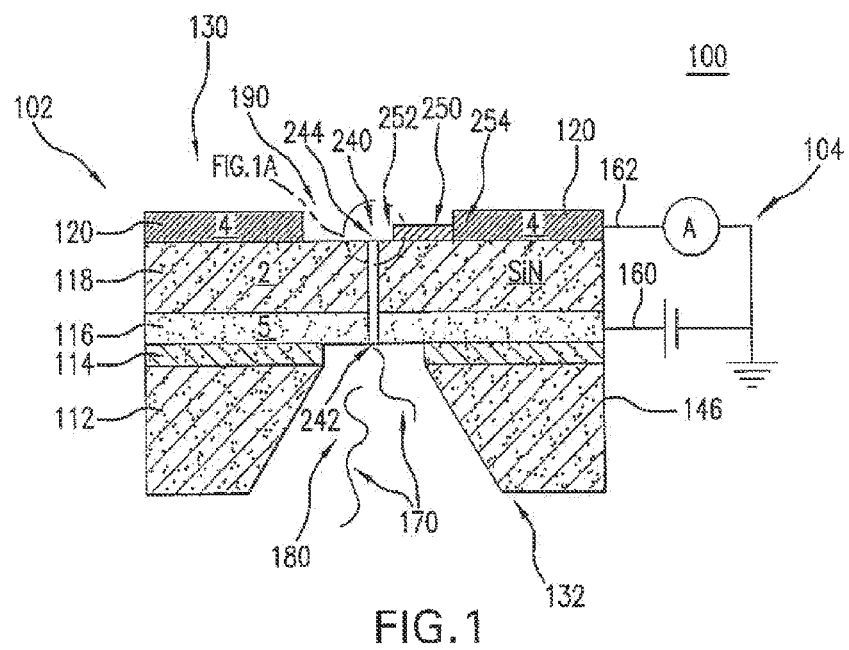
FIG. 1 shows the overall structure of a device in accordance with one embodiment of the present invention, with the molecular recognition chip shown in vertical cross-section.
Figure 1A:
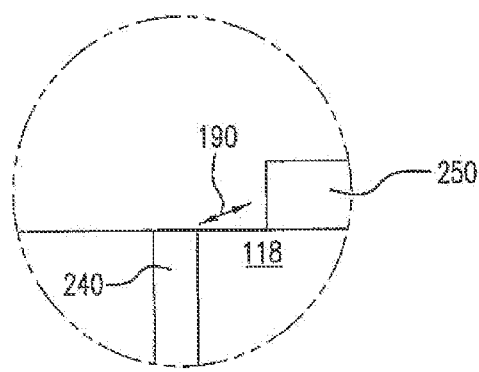
FIG. 1A is an enlarged view of a portion of FIG. 1 showing the tunnel gap between the translocation nanotube and the contact nanotube.

One embodiment of the present invention provides a device 100 shown in FIG. 1. The device 100 includes a molecular recognition chip 102 connected to an electrical measurement circuit 104. In one embodiment, the electrical measurement circuit 104 is configured to measure a tunneling current as discussed further below.

In one embodiment, the chip 102 comprises a substrate 112, a first insulating layer 114 formed over the substrate 112, a first metal contact layer 116 formed over the first insulating layer 114, an second insulating layer 118 formed over the first metal contact layer 116, and a second metal contact layer 120 formed over the second insulating layer 118. In one embodiment, the second metal contact layer 120 may be ring-shaped. In one embodiment, the substrate 112 is formed from silicon, the first insulating layer 114 is an oxide layer (e.g., silicon dioxide) and the second insulating layer 118 is a silicon nitride (SiN) layer. The first and second metal contact layers 116, 120 are formed from a material capable of forming an ohmic contact with a nanotube. In one embodiment, palladium is used for the first and second metal contact layers 116, 120. Palladium is known to form ohmic contacts with carbon nanotubes, which are used in conjunction with the chip 102 as described further below.

The chip 102 has a upper surface 130 and a lower surface 132. The various layers of the chip 102 made be etched to result in the shape shown in FIG. 1 using techniques known to those skilled in the art.

A first nanotube 240 (the "translocation nanotube") is formed through a thickness of the chip 102. The translocation nanotube 240 has a lower end 242 and an upper end 244 connected by a through channel 146. Proximate its lower end 242, outer walls of the translocation nanotube 240 make an ohmic contact with the first metal contact layer 116. Proximate its upper end 244, outer walls of the translocation nanotube are surrounded by the insulating material from the second insulating layer 118. The through channel 146 of the translocation nanotube 240 provides the chip 102 with a nanopore 146 through which molecules, such as DNA, can translocate. In one embodiment, the translocation nanotube 240 is a carbon nanotube (CNT).

In one embodiment, a second nanotube 250 (the "contact nanotube") is formed on the second insulating layer 118 at a location where the second insulating layer forms a portion of the chip's upper surface 130. The contact nanotube 250 has a first end 252 that is separated by a gap 190 (a "tunnel gap") from the upper opening 244 of the translocation nanotube 240. The contact nanotube 250 also has a second end 254 which forms an ohmic contact with a portion of the second metal contact layer 120. As stated above, the second metal contact layer 120 may have a ring-shape, and so may partially or entirely encircle the translocation nanotube's upper end 244. In one embodiment, the contact nanotube 250 is also a carbon nanotube (CNT). In some embodiments, the translocation nanotube 240 and the contact nanotube 250 are substantially identical in structure.

A first lead 160 of the electrical measurement circuit 104 contacts the first metal contact layer 116 (which forms an ohmic contact with the lower end of the translocation nanotube 240). A second lead 162 of the electrical measurement circuit forms an ohmic contact with the second metal contact layer 120 (which forms an ohmic contact with the second end of the contact nanotube). Thus, when the tunnel gap 190 between the translocation nanotube's upper end 244 and the contact nanotube's first end 252 is occupied by an electrically conductive moiety, such as a portion of a DNA strand, a measurable current flows through the electrical measurement circuit 104.

In one embodiment, the device 100 is configured to read one of the bases as a DNA strand 170 passes from a lower side 180 of the chip 102 to an upper side 190 of the chip 102, through the translocation nanotube 240. One nanotube is used for translocating DNA while the second nanotube is used to contact the DNA and generate an electrical signal. The contact nanotube is functionalized for recognition of a particular nucleotide. It is therefore understood that multiple such chips 102 may be required so that all nucleotides may be read as identical DNA strands simultaneously translocate through chips having differently-functionalized contact nanotubes.

As a DNA strand 170 passes through the translocating nanotube 240, it will form a first set of bridging hydrogen bonds between its phosphates and a phosphate grabber molecule attached to the end of the translocating nanotube 240. It will also form a second set of bridging hydrogen bonds between its bases and a recognition element tethered to the contact nanotube 250, thereby completing an electrical circuit, but only if a nucleotide on the DNA strand is in some sense complementary to the recognition element (e.g., a recognition 'base') tethered to the contact nanotube 250. In one embodiment, the phosphate grabber molecule comprises a guanidinium moiety and the recognition element is a modified base complementary to the base on the DNA strand.

It is understood that to make use of the device 100, the device 100 must be mounted in an assembly configured to cause a DNA strand to pass the lower side 180 of the chip 102 to the upper side 190 of the chip 102. In one embodiment, such an assembly may be provided with electrical circuitry that causes the DNA strand to electrophoresceorese through the translocation nanotube 240. Magnetic beads or the like may affixed to a leading end of the DNA strand so as to properly orient the DNA strand in preparation for translocation.

FIGS. 2A-2M illustrate one embodiment for fabricating the device 100 seen in FIG. 1

Figure 2A:
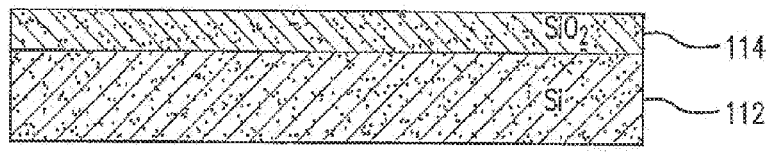
FIGS. 2A-2M illustrate different stages in the fabrication of the chip of FIG. 1, in accordance with one embodiment of the present invention.

As seen in FIG. 2A, one first provides suitable silicon substrate 112 having alignment marks for future processes. Then, a first insulating layer 114 is formed over the silicon substrate. In one embodiment, the first insulating layer 1114 is formed by growing an oxide layer 114 on top of the silicon layer 112. In one embodiment, the oxide layer 114 has a thickness of about 10 nm.

Figure 2B:
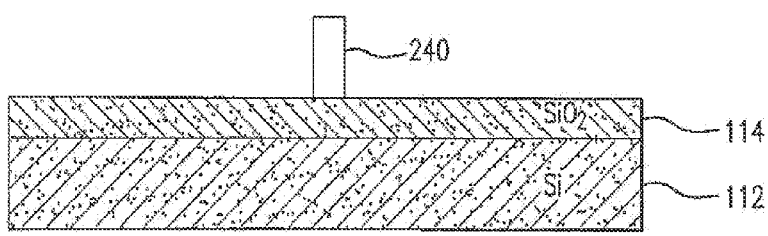

As seen in FIG. 2B, the next step is to provide one or more vertically oriented carbon nanotubes 240 (which will later be used as translocation nanotubes) on the first insulating layer 114. The carbon nanotubes 240 are provided at low density on the insulating layer 114. In one embodiment, the vertically oriented carbon nanotubes are to grown. Dai has reported arrays of 2 nm Fe or Co metals (By EBL) as seeds for single-walled nanotube (SWNT) growth. However, under normal conditions, micron long single-walled carbon nanotubes (SWNTs) lie on the surface. An alumina template may be needed to get the CNTs to grow vertically on the substrate. Another choice is to grow short multi-walled nanotubes (MWNT). Furthermore, silica nanotubes may also be a candidate for this purpose.

Figure 2C:
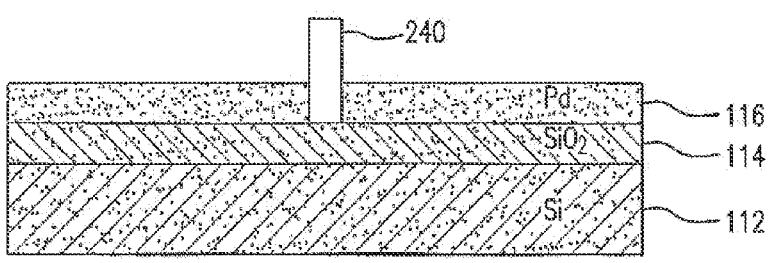

As seen in FIG. 2C, the next step is to form a first metal contact layer 116 over the first insulating layer 114. In one embodiment, palladium (Pd) or a palladium-gold (Pd/Au) alloy is deposited on top of the oxide layer so as to form a metallic ohmic contact to the translocation nanotube 240. Palladium has been shown to be a suitable contact material for metallic SWNTs. In one embodiment, a 5 to 10 nm layer of Pd or Pd/Au alloy is deposited on the first insulating layer 114.

Figure 2D:
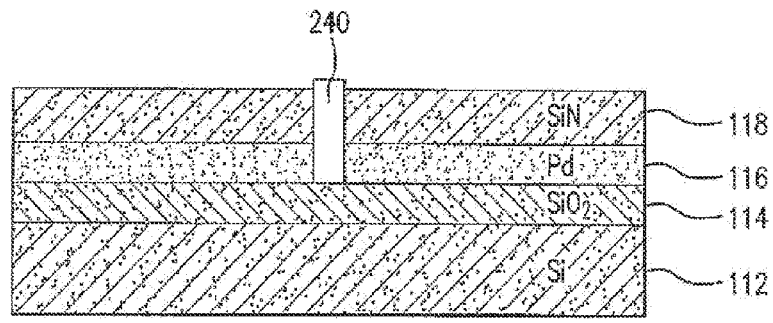

As seen in FIG. 2D, the next step is to form a second insulating layer 116 over the first metal contact layer 114. In one embodiment, the second insulating layer comprises a layer of silicon nitride (SiN). In one embodiment the silicon nitride is deposited on top of the first metal contact layer 114 to a thickness of about 50 to 100 nm layer. The silicon nitride acts as both an electrical insulator (relative to the first metal contact layer) and also acts as a fluid barrier between top and bottom surfaces of the final device 100.

Figure 2E:
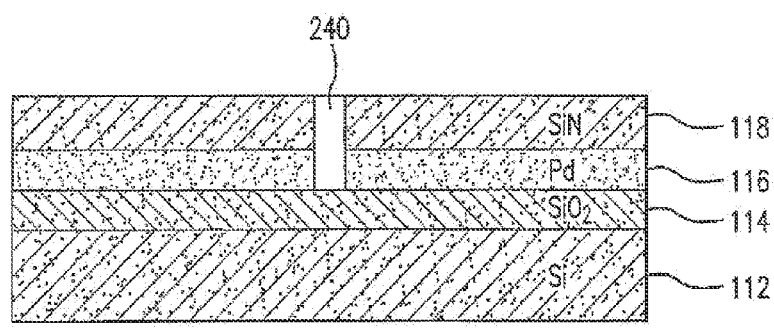

As seen in FIG. 2E, the next step is to perform an "etch back" remove the extra portion of the translocation nanotube 240 protruding above the surface of the second insulating layer 116. In one embodiment, this may be accomplished with a hydrogen plasma etch or anodic electrochemical etching. As a result of this step the upper surface of the second insulating layer 116 may be smoothed.

Figure 2F:
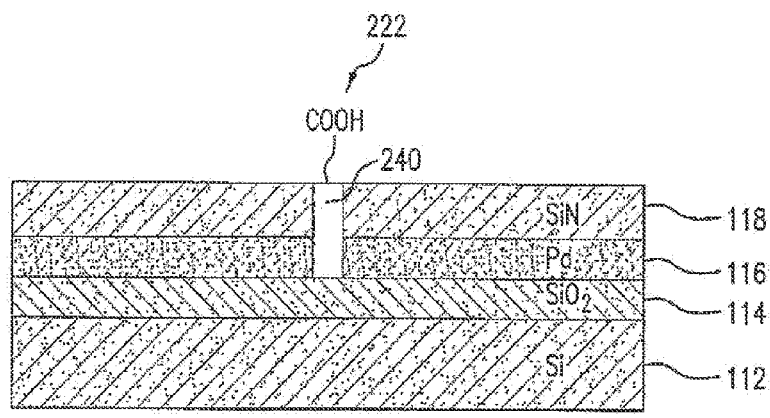

As seen in FIG. 2F, the next step is to functionalize the translocation nanotube 240 with a carboxylic acid group 222.

In one embodiment, this may be accomplished by etching for 2 hours in a 6M $H_2SO_4$, 2M $HNO_3$ solution.

Figure 2G:
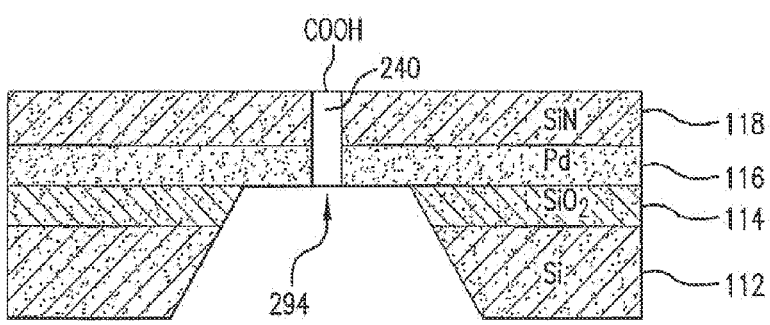

As seen in FIG. 2G, the underside of the silicon substrate 112 is etched to form a window 294. In one embodiment, this may be accomplished by KOH etching under a desired portion of the structure. In one embodiment the window 294 size is chosen based on the density of nanotubes and the final probability of success, given the yield at each stage of the fabrication process. Specifically, if the probability of forming a successful reading junction is pj, and the number of nanotubes per unit area is N/A, then the desired area of the final chip, Am is given by Am=A/(pj×N). This will result in, on average, one properly connected, functioning junction per chip. The remainder of the first insulative layer 114 proximate the window, and metal particles used for seeds for growing the translocation nanotube 240 are removed by reactive ion etching. This can expose the lower end 242 of the translocation nanotube 240.

Figure 2H:
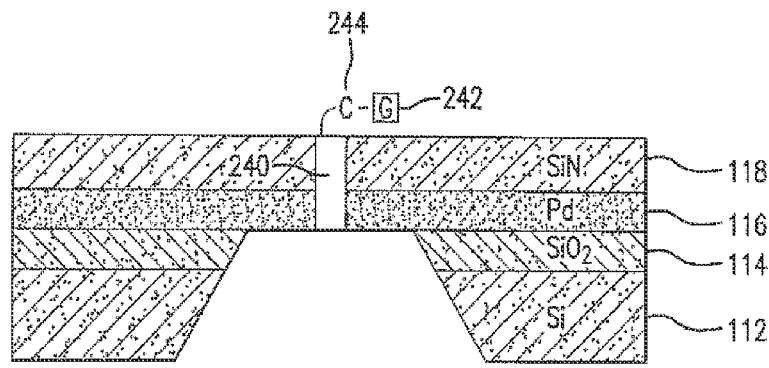
Figure 3:
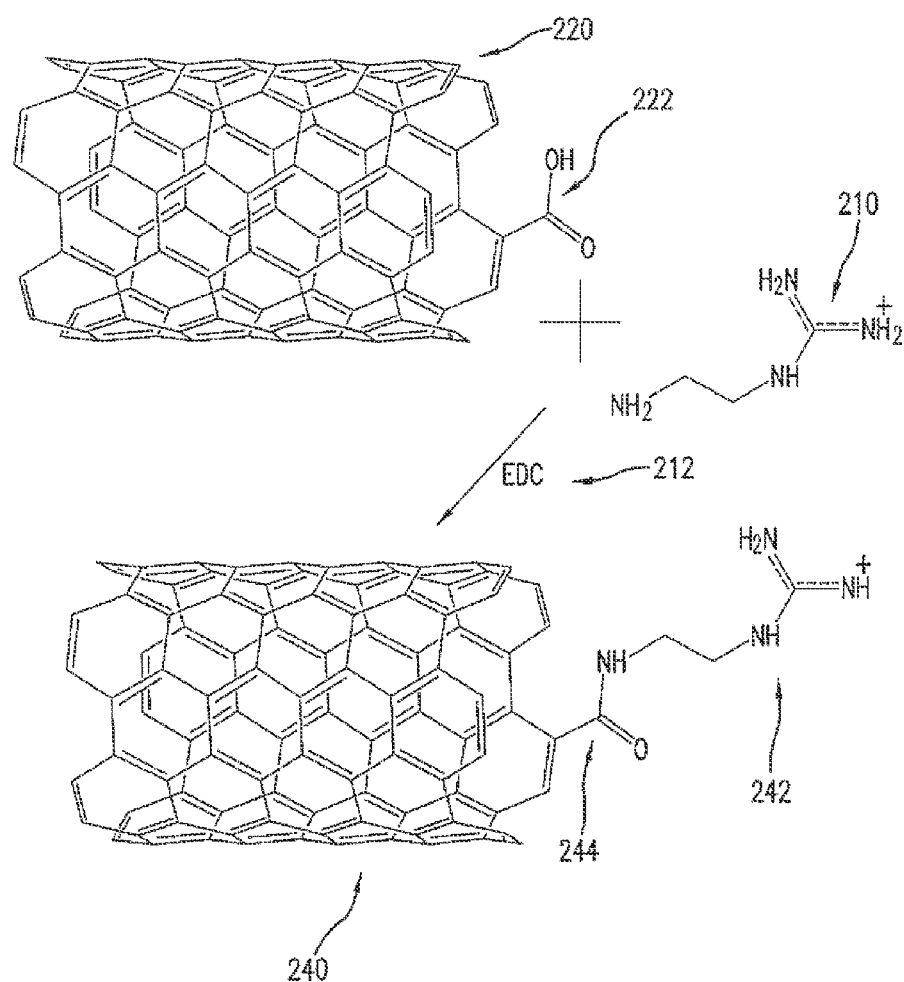
FIG. 3 illustrates one embodiment of a process for functionalizing an end of a nanotube with guanidinium.

As seen in FIG. 2H, the translocation nanotube 240 functionalized with one or more carboxylic acid groups 222 is reacted with a guanidinium group 210 tethered to a primary amine. When reacted with the carboxylate group on the CNT by means of a zero-length cross-linker such as EDC 212 (1-ethyl-3-[3-dimethylaminopropyl]carbodiimide hydrochloride), the result is an amide bond, thereby resulting in a carbon atom 244 anchoring a guanidinium group 242, as seen in FIG. 3.

Separately, a separate batch of micron-long metallic CNTs (which will eventually serve as contact nanotubes) are carboxylated and then reacted with one of the bases (or other recognition elements). These recognition elements are also connected to a primary amine to facilitate attachment to the carboxylated end of nanotubes using EDC or other coupling reagents.

Figure 2I:
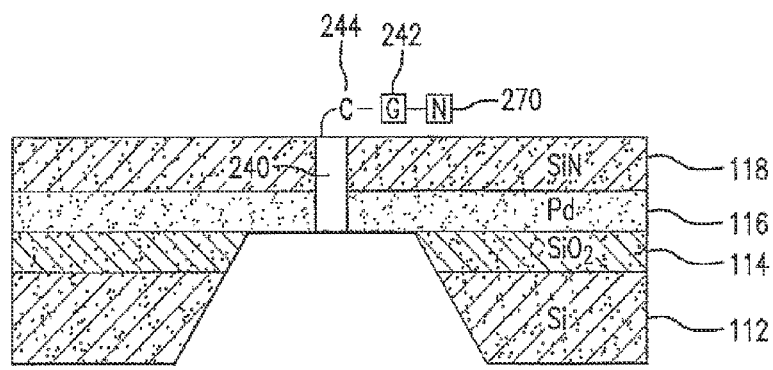

As seen in FIG. 2I, a sacrificial nucleotide 270 (see FIG. 4) is connected to the assembly on the silicon nitride surface 118 containing the guanidinium-functionalized nanotube 240. This sacrificial nucleotide is complementary to the recognition element that was tethered to the contact nanotube discussed immediately above. This is done so that upper ends 244 of the translocation nanotube 240 can become bound to the first end 252 of a carbon nanotube, via phosphate to guanidinium hydrogen bonds.

Figure 2J:
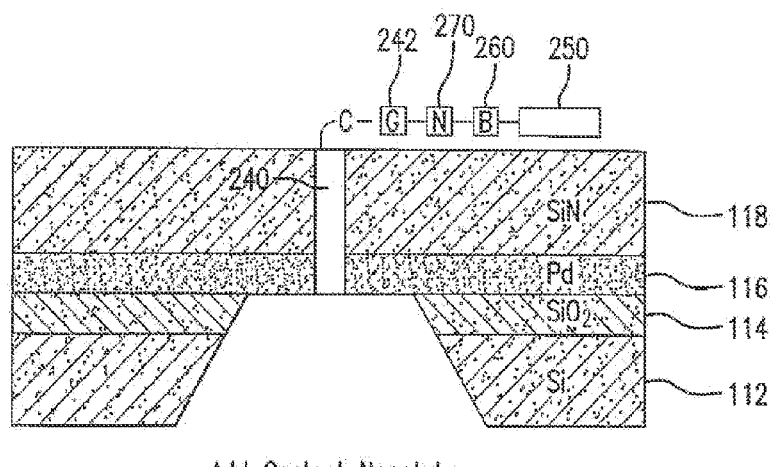
Figure 4:
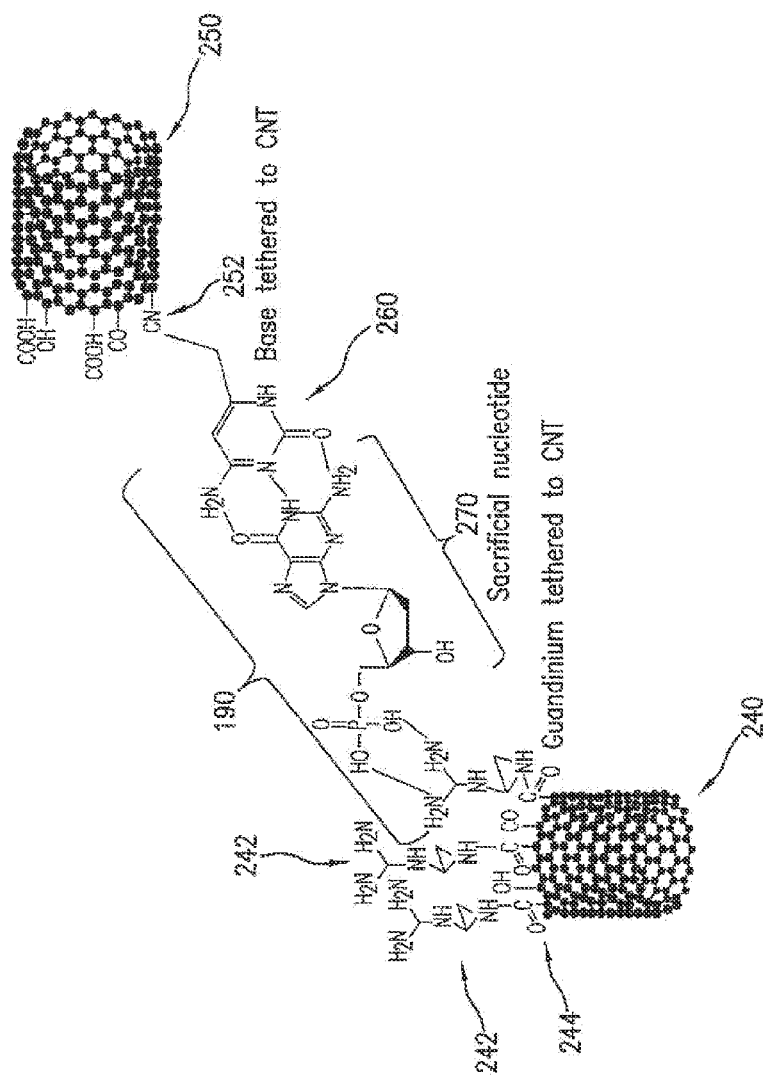
FIG. 4 illustrates one embodiment of a process for aligning a contact nanotube relative to a translocating nanotube.

As seen in FIG. 2J, contact nanotubes 250, which are tethered to recognition elements, are flowed over the silicon nitride surface 118 surface containing the guanidinium-bound nucleotides tethered to the translocation nanotubes 240. As a result, some of the translocation nanotubes 240 will become bound to contact nanotubes 250 bearing recognition elements via hydrogen bonding with the recognition element 260. The overall arrangement of one type of hydrogen-bonded nucleotide is shown in FIG. 4. Other devices for recognizing other bases will be assembled with the appropriate nucleotides and recognition elements. This can be done on a wafer having multiple chips and appropriate masking to control the assembly.

Figure 2K:
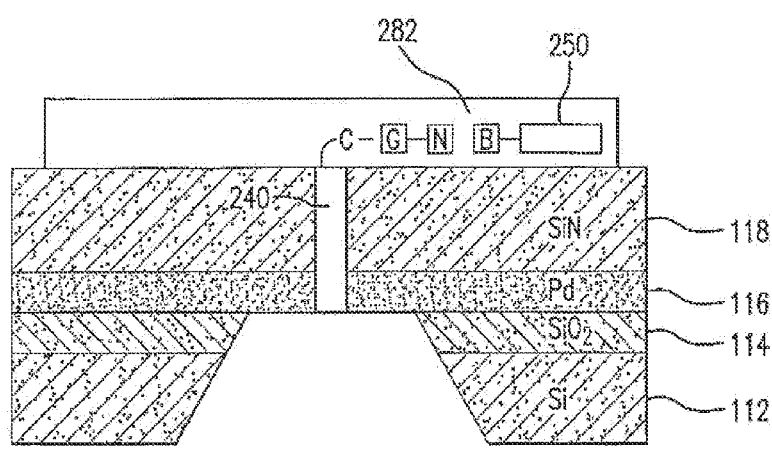

As seen in FIG. 2K, a protective passivation layer 282 is placed over the structure to cover the active area, in preparation for the subsequent steps. In one embodiment, the passivation layer covers at least the translocation nanotube 240 and the contact nanotube 250.

Figure 2L:
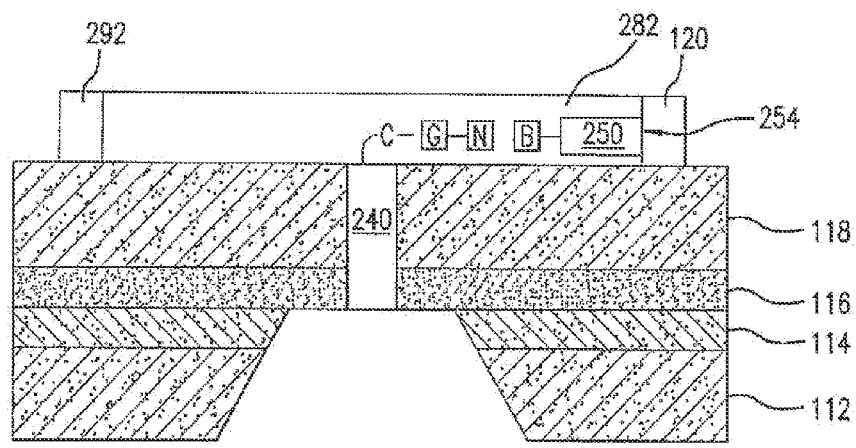

As seen in FIG. 2L, a second metal contact layer 120 is formed such that it contacts the second end 254 of the carbon nanotube 250. In one embodiment, the second metal contact layer 120 is formed from the same materials as the first metal contact layer (for instance, formed from Pd or a Pd/Au alloy). In one embodiment, the second metal contact layer is formed in the shape of a ring. The ring-shape facilitates an ohmic contact to the contact nanotube, and also facilitates the formation of contacts to electrical leads 160, 162 of an electrical measurement circuit configured to measure a tunneling current between the translocation nanotube 240 and the contact nanotube 250.

Figure 2M:
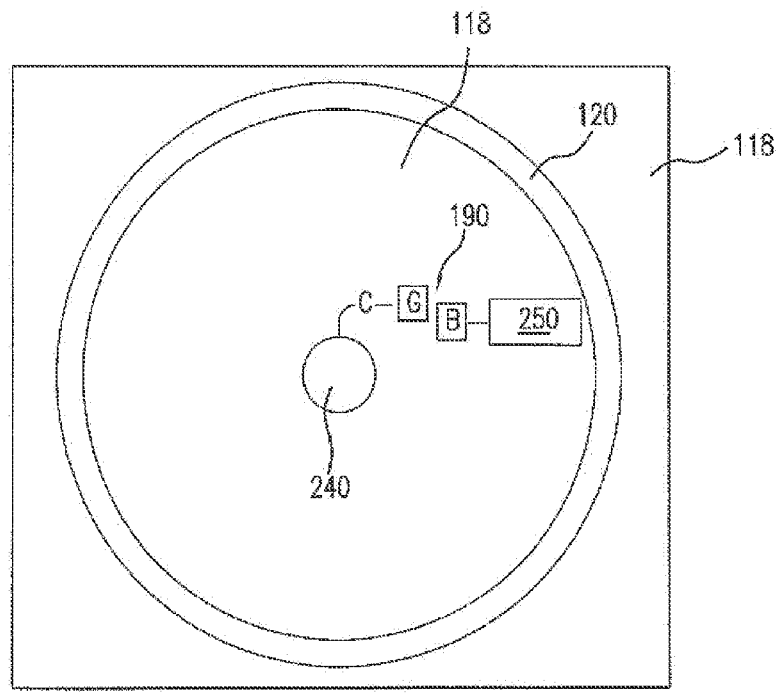

Finally, as seen in FIG. 2M, the passivation layer 282 is removed, as is the sacrificial nucleotide 270 used as an alignment template. In one embodiment, these two items are removed with acid. This leaves the desired gap 190 for bases on a DNA strand to be trapped via the phosphates by the translocation nanotube 240 and via the complementary recognition element on the contact nanotube 250.

FIG. 3 shows the process for functionalizing a nanotube with guanidinium 210 to form the translocation nanotube 242. One or more guanidinium molecules 210 are attached to an available carboxyl group 222 (—COOH) formed on the end of a carbon nanotube 220. Techniques for attaching guanidinium to a carboxyl group are known to those of ordinary skill in the art. This results in a carbon nanotube 240 in which guanidinium moieties 242 are tethered to the carbon atoms of what formerly were available carboxyl groups 222 on the original carbon nanotube 220.

Similarly, one of four bases (A, C, T or G) derivatives can be tethered to an available carboxyl group on a carbon nanotube to form a functionalized recognition element of the contact nanotube. In this manner, the contact nanotube serves as a functionalized recognition nanotube which is adapted to recognize a nucleotide complementary to the base tethered thereto.

During sequencing operations, as the DNA strand 170 translocates through the nanopore of the translocation nanotube 240, it emerges from the latter's upper end 244. As this happens, a phosphate from the backbone of the emerging DNA strand 170 forms a first set of temporary hydrogen bonds with a guanidinium moiety 242. At roughly the same time, a nucleobase of the emerging DNA strand 170 forms a second set of temporary hydrogen bonds with the functionalized recognition element belonging to the contact nanotube. When both sets of bonds form, a detectable tunneling current is created and measured by the electrical measurement circuit 104. Analysis of the time-varying magnitude of the detected tunneling current can provide information about the nucleotide's identity. The principle behind this paradigm for identifying nucleotides are discussed in J He, Jin, Lin, Lisha, Zhang, and Lindsay. Identification of DNA base-pairing via tunnel current decay. Nano Letters 7 (12), 3854-3858, 2007, whose contents are incorporated by reference.

FIG. 4 illustrates the process for aligning the first end 252 of the contact nanotube 250 on the upper surface 130 of the chip 102, relative to the upper end 244 of the translocation nanotube 240. As seen in FIG. 4, guanidinium moieties 242 are tethered to the upper end 244 of the translocation nanotube 240 while a base 260 (in this instance, cytosine) is tethered to the first end 252 of the contact nanotube 250. The cytosine base 260 serves as the functionalized recognition element 260 for the contact nanotube 250.

The alignment technique relies on self-alignment of the contact nanotube 250 relative to the translocation nanotube 240, with the assistance of a sacrificial nucleotide 270. In the shown embodiment, the sacrificial nucleotide 270 is deoxyguanosine monophosphate. The sacrificial nucleotide is introduced so that its phosphate group 272 forms a first set (in this instance, a pair) of hydrogen bonds with one of the guanidinium moieties 242. The sacrificial nucleotide's forms a second set of hydrogen bonds with the functionalized recognition element 260 belonging to a contact nanotube 250.

The position of the contact nanotube 240 is adjusted to align and form this second set of hydrogen bonds, thereby creating an optimal tunnel gap 190 between the contact nanotube 250 and the translocation nanotube 240. It is understood that the precise distance of the tunnel may vary slightly from chip to chip, depending on the exact configuration and morphology of the guanidinium moieties 242 and the base 260. Once alignment has been completed, the sacrificial nucleotide 270 may be removed and the chip 102 prepared for use in DNA sequencing.

It is understood that the association of the guanidinium moieties 242 with the translocation nanotube 240 and the functionalized recognition element 260 with the contact nanotube 250 is a matter of design choice. One may equally configure the chip 102 such that the translocation nanotube 240 is provided with the functionalized recognition element 260 while the contact nanotube 250 is provided with the guanidinium moieties 242. In other embodiments, the translocation nanotube may be functionalized with a recognition element, such as a base (A, G, C or T) or a base reader and the contact nanotube may be functionalized with a base-pair reader as disclosed herein below. Alternatively the translocation nanotube may be functionalized with a base pair reader and the contact nanotube may be functionalized with the base or base reader recognition element.

Furthermore, in another embodiment, instead of using self-alignment, an active positioning device is used to position the contact nanotube 250. In this embodiment, the contact nanotube 250 would be attached to a nanopositioning device, such as the scanning head of a scanning tunneling microscope or atomic force microscope, and moved into position by using electronic tunneling between the two nanotubes as an indicator of their proximity.

The present invention uses chips provided with both a translocation nanotube and a functionalized contact nanotube, in conjunction with and hydrogen bonding for molecular recognition. Since the natural DNA bases frequently form mismatched base pairs, custom recognition elements are used for molecular recognition and so each contact nanotube is functionalized with at least one such custom recognition element.

Thus, in one embodiment, a device may be used to sequence a strand of DNA by the following set of principal steps:

Step 1. Provide a wafer having a plurality of chips 102 of the sort seen in FIG. 1. The wafer should have at least four types of chips, each type having a contact nanotube functionalized to recognize one of the four bases, should be provided. Instead of single wafer, one may instead provide an apparatus having the four types of chips separately mounted therein.

Step 2. Place the wafer in an apparatus configured to accommodate DNA sequencing, with copies of the DNA strand to be sequenced present on the lower side of each such chip. Optionally, the DNA may be modified so as to allow entry into the translocation nanotube from one direction only. In one embodiment, this may be done by tethering the DNA to a bead.

Step 3. Electrophorese the DNA strands through the nanopore of the translocation nanotubes of each chip, in synchrony. If extra pulling force is needed, functionalize the end that passes through pore (after having been modified with e.g., biotin) and attach magnetic bead.

Step 4. Pull DNA through by electrophoresis and/or magnetic bead.

Step 5. Record current pulses ($I_t$) as a function of time as the DNA strands emerge from the nanopore of the translocation nanotube and form temporary hydrogen bonds with the guanidinium and the different recognition elements attached to the contact nanotube, thereby creating a detectable tunneling current.

Step 6. Align data from a plurality of reads for each type of base reader.

Step 7. Align data from all 4 reads.

Although the present invention has been described to a certain degree of particularity, it should be understood that various alterations and modifications could be made without departing from the scope of the invention as hereinafter claimed.

Device Utilizing a Trans Base Tunnel Reader

Figure 5:
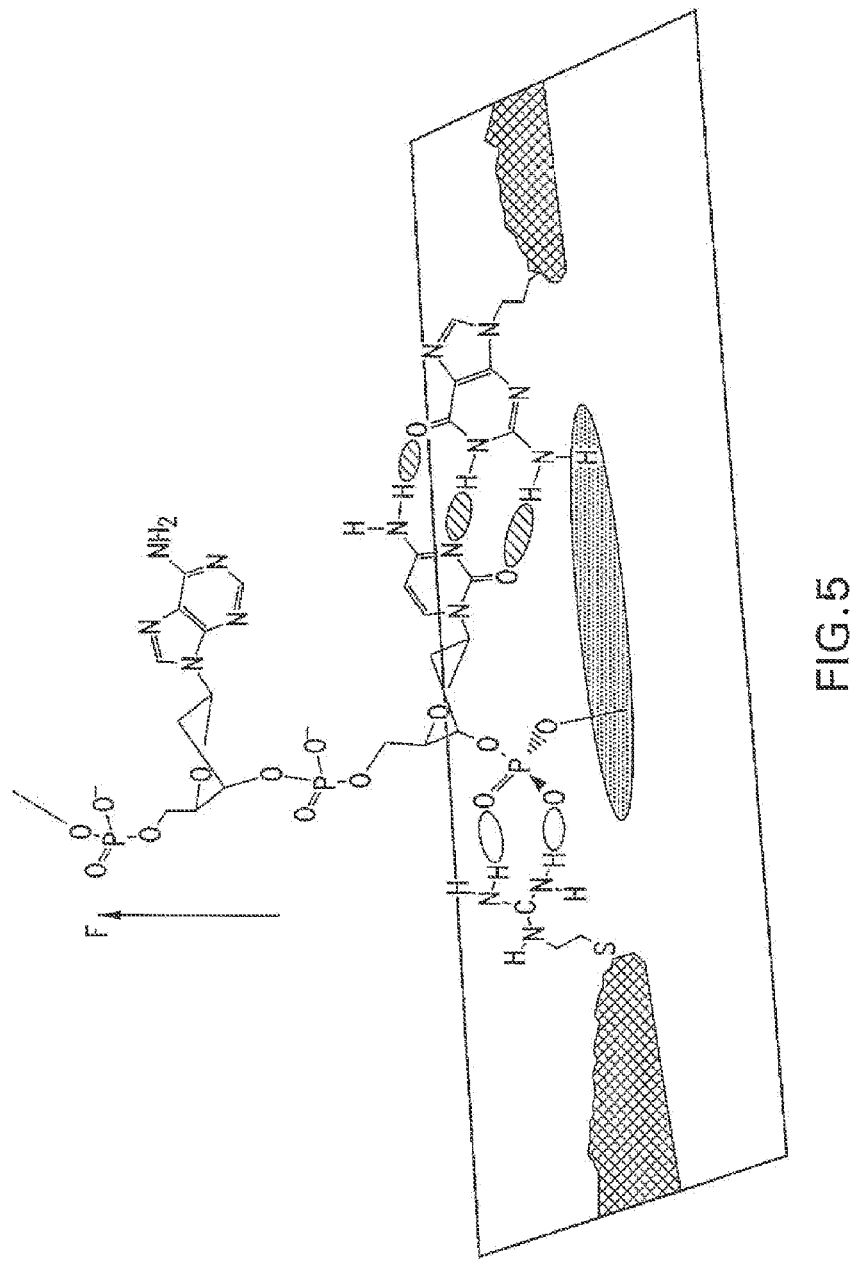
FIGS. 5 and 5A: Sequencing by recognition through affinity elements, showing one of four types of reader (this one is for C). A guanidinium ion tethered to one electrode via a flexible linker, hydrogen bonds (yellow H-bonds) onto the nearest passing phosphate on an ssDNA translocating a nanopore. If a flexibly tethered base on a second electrode finds it is a Watson-Crick complement on the other side of the DNA (red H-bonds) a large current passes between the two electrodes, signaling a base recognition event. The components require an electrode gap of about 3 nm and an electrode height of no more than 0.6 nm or 0.7 nm. The H-bonding also serves to align the DNA in the device, while the flexible linkers provide alignment tolerance. Translocation is controlled via electrophoresis and magnetic beads (with net force F) an arrangement compatible with a parallel assembly of many reading heads.

FIG. 5 shows one embodiment of a device for sequencing single-stranded DNA (ssDNA) by hydrogen-bonding recognition, in accordance with the present invention. In its simplest form, each recognition-molecule (referred to as a 'base-reader') reads a specific DNA base, the full sequence being assembled by juxtaposing data from four different readers. As the ssDNA passes the electrodes via a constriction (e.g., a nanopore), a guanidinium ion grabs the nearest phosphate (depicted in FIG. 5 by the two yellow hydrogen bonds), while a base reader recognizes its Watson-Crick complement (depicted in FIG. 5 by the three red hydrogen bonds) when it is present. So long as both molecular recognition events overlap in time, a large current will flow, with the consequent charge pulse signaling identification of the target base. In another embodiment, one electrode is fitted with a base or base reader that will recognize its Watson-Crick complement and the other electrode is fitted with a base-pair reader, described herein below.

Figure 5A:
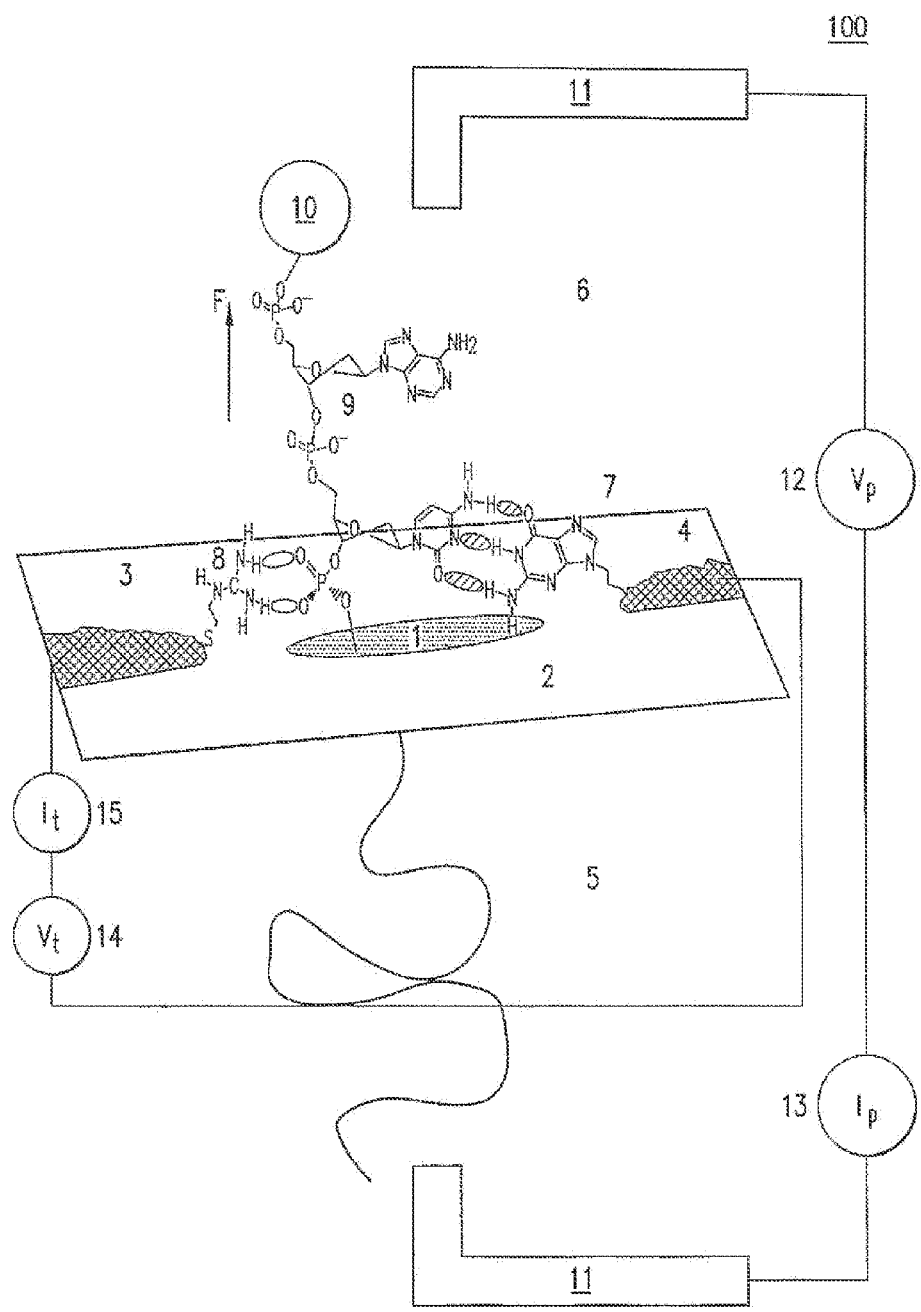
Figure 7A:
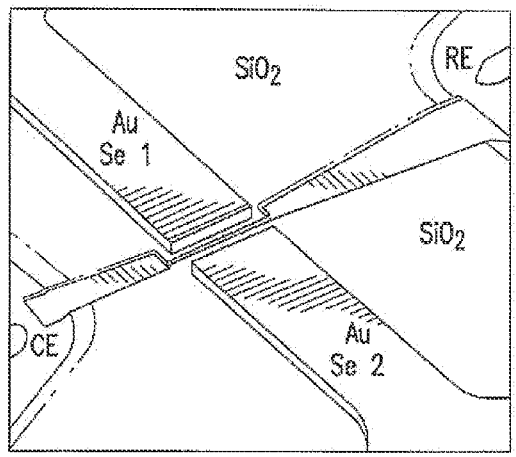
FIG. 7A-7D: Testbed nanogap made by lithography and FIB.
Figure 7B:
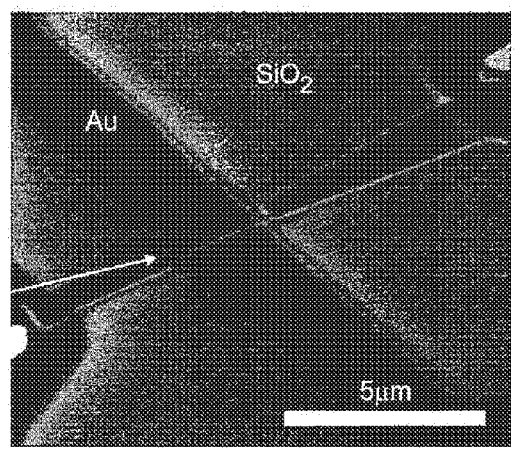
Figure 7C:
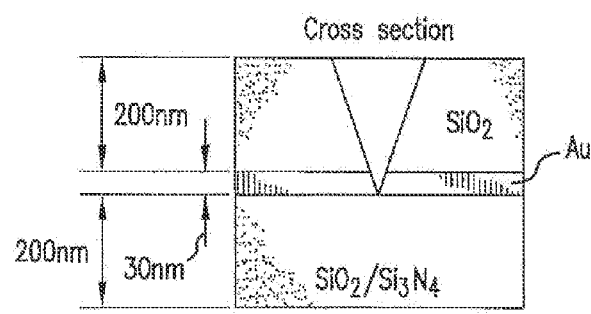
Figure 7D:
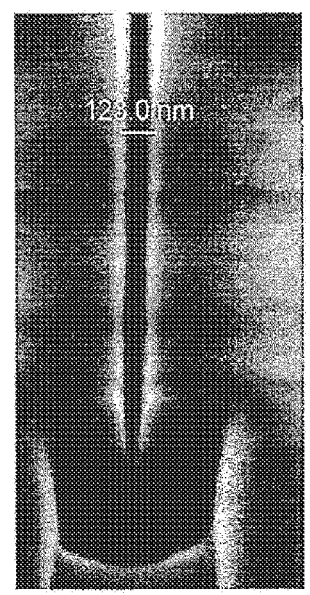

FIG. 5a shows the device 2 of FIG. 5 arranged in an apparatus 100 configured to read bases in ssDNA, by measuring tunneling current. A constriction in the form of a nanopore 1, is formed in the device 2. In the embodiment of FIGS. 5 and 5A, the constriction is in the form of a nanopore 1 which passes through a thickness of a substrate. It is understood, however, that a constriction may take on other forms and arrangements as well. Thus, in an alternate embodiment, the constriction may comprise a narrowed portion of a microfluidic channel formed on a surface of a substrate. In other words, the constriction may lie on top of a device with the target molecule passing from a first chamber on top of the device to a second chamber on top of the same device. In such case, the constriction connects the two chambers which are separated by a surface partition. In another embodiment, the constriction comprises a nanopore created by a single walled carbon nanotube (SWCNT).

In one embodiment, the device 2 comprises a chip 2 which, in turn, comprises a substrate provided on a thin $Si_3N_4$ membrane. The top of the chip 2 seen in FIG. 5A comprises a first side while the bottom of the chip 2, which is hidden from view in FIG. 5A, comprises a second side. Thus, the device 2 may be considered to comprise a partition having a first side and a second side, and the ssDNA translocates from one side of the partition to the other side of the partition, via the constriction 1. First and second electrically conductive sensing electrodes, 3, 4 which are spaced apart from one another by a gap, are provided adjacent the nanopore 1 on the first side of the chip 2. In one embodiment, the gap between the first and second electrodes is between 1.0-5.0 nm, though larger gaps may be possible. The first and second sensing electrodes are preferably formed of gold, though they may instead be formed of other electrically conductive materials.

The chip 2 is mounted in the device 100 such that the chip's first side (top) is exposed to a first fluid chamber 6 ("upper chamber") and the chips second side (bottom) is exposed to a second fluid chamber ("lower chamber"). As seen in FIG. 5A, the second fluid chamber 6 contains the ssDNA 9 to be read, while the first fluid chamber receives the ssDNA 9 translocating through the nanopore 1 which forms a passage between the two fluid chambers 5, 6.

On the first side of the nanopore 1, a first affinity element 8 is tethered to the first sensing electrode 3 via a first flexible linker. Generally speaking, a "linker" is a chemical entity designed so as to permit adequate motion of the affinity element to self-assemble on the target while remaining in electrical communication with an electrode. The first flexible linker itself may be bonded to the first electrode via an electrode molecular anchor, such as a thiol. In one embodiment, the first affinity element 8 comprises guanidinium or a guanidinium derivative such as guanidinoethyl disulfide. Guanidinium performs the function of grabbing the phosphate of backbone of the ssDNA 9 and thus serves as "phosphate grabber."

On the second side of the nanopore, a second affinity element 7 is tethered to the second sensing electrode 4 via a second flexible linker. The second flexible linker itself may be bonded to the second electrode via an electrode attachment molecule, as described above. In one embodiment, the second affinity element 7 comprises a base reader which is configured to recognize one of the four bases on the ssDNA 9. In general, both the phosphate grabber and the base reader form hydrogen bonds that are readily broken at room temperature. Thus, the bonds formed during translocation are made and broken on a timescale that permits rapid binding and release of the target while still allowing for detection and measurement of a tunneling current.

In one embodiment, the flexible linkers associated with either or both sensing electrodes may comprise an alkane. A thiol serves as the electrode molecular anchor, and so the combined linker-electrode attachment molecule may comprise —$CH_2$—$CH_2$—SH. The flexible linkers allow the reader to rotate freely and also allow the bases in the reader to rotate and associate with its complement.

In one embodiment of the present invention, reference (RE) and counter (CE) electrodes are incorporated into the chip itself, spaced a few microns from the tunneling gap.

As also seen in the embodiment of FIG. 5A, a first magnetic bead 10 may be affixed to a leading end of the ssDNA 9 and used to pull the ssDNA 9 through the nanopore 1. Optical tracking of the bead allows transit of the ssDNA to be followed to within 20 nm. It is understood, however, that a second magnetic bead may be used on the second side of the device (i.e., in second fluid chamber 5) to help untangle the secondary structure of the DNA.

A pair of polarization electrodes 11 are used to polarize the nanopore 1 for electrophoretic transport of the ssDNA 9. A voltage bias 12 and a current monitor 13 are used to control the electrophoretic transport.

The first and second sensing electrodes 3, 4 are connected to a sensing electrode bias 14 and also to current measuring circuitry 15 to gauge the tunneling current as each nucleotide is detected during translocation of the ssDNA 9. It is from the measured tunneling current at one or more nanopores that the corresponding portion of the ssDNA can be identified.

Figure 20:
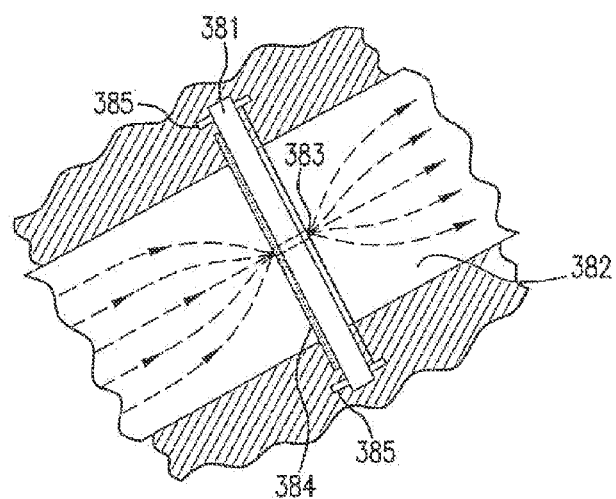
FIG. 20 shows an embodiment of a device in which the constriction in found in a microfluidic channel formed on a surface of the device.

FIG. 20 shows an exemplary arrangement, where the device 381 is placed in a microfluidic channel 382. The stream lines show the fluid being diverted in order to pass through the constriction 383. The electrode surfaces within the microfluidic channel are insulated from the fluid in the channel by a protective layer of insulation 384. Connections to the electrodes 385 exit the structure outside of the fluid channel.

Figure 21A:
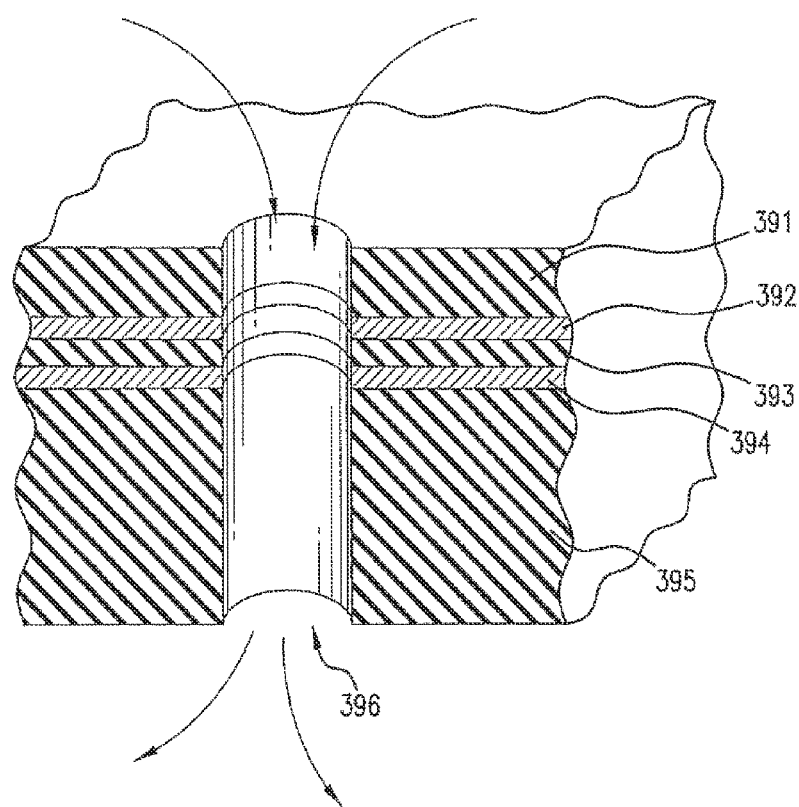
FIGS. 21A and 21B show an embodiment of a device in which the constriction is a pore through a substrate and the electrodes comprise layers along the thickness of the pore.

FIG. 21A shows an exemplary cross section of an embodiment of a device 391 through a fluid channel showing a planar electrode arrangement. 391 is the top layer of insulation, 392 is a first metal or doped semiconductor layer, 393 is a second layer of insulation, 394 is a second metal or doped semiconductor layer and 395 is the insulating substrate on which the structure is formed. The size of the constriction between the electrodes is determined by the thickness of the second layer of insulation 393. The structure is assembled by planar deposition of alternating conducting and insulating layers on the substrate, followed by formation of a channel, 396, through the entire structure.

Figure 21B:
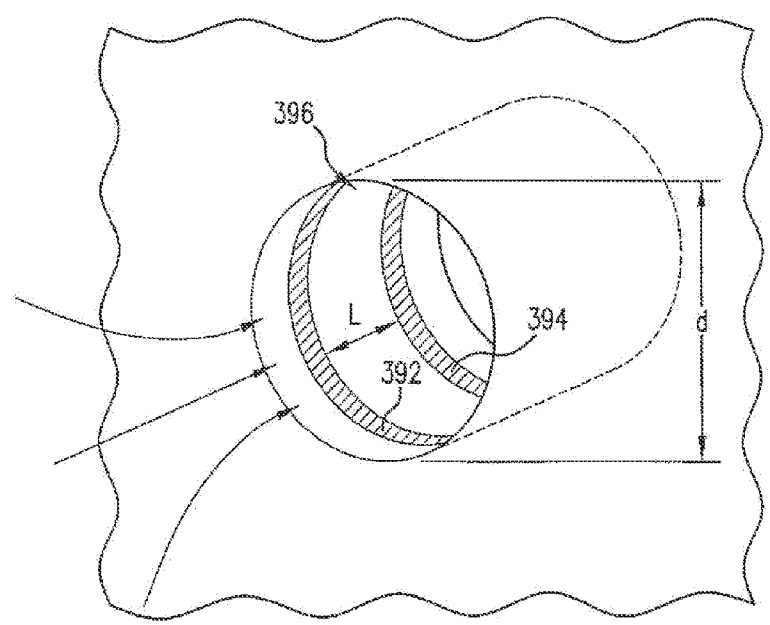

FIG. 21B illustrates one embodiment of dimensions for operation of the device seen in FIG. 21A. In this embodiment, the spacing between the electrode pair, 392 and 394, is L and the diameter of the channel 396 diameter is d. In order to obtain adequate tunnel conductance through the target molecule, L lies in the range from 0.5 to 10 nm. The channel diameter is constrained only by the requirement that a molecule entering the channel touch the sides, and hence the electrodes, during its transit through the channel. If the speed of fluid flow through the channel is V meters per second than the time spent between the electrode pair is:

$t = V/L$ seconds.

In this time the molecule must diffuse a lateral distance d, given by $d = \sqrt{Dt}$ where D is the diffusion constant of the molecule. Thus the maximum speed of transit of the sample passed the electrodes is given by:

$V \leq DL/d^2$.

Thus the speed with which fluid can be processed decreases rapidly as the constriction size is increased. For example, with L=5 nm, d=10 nm and D=100 (μm)2/s (typical of a small protein), V is preferably less than 5 mm/s.

Figure 22A:
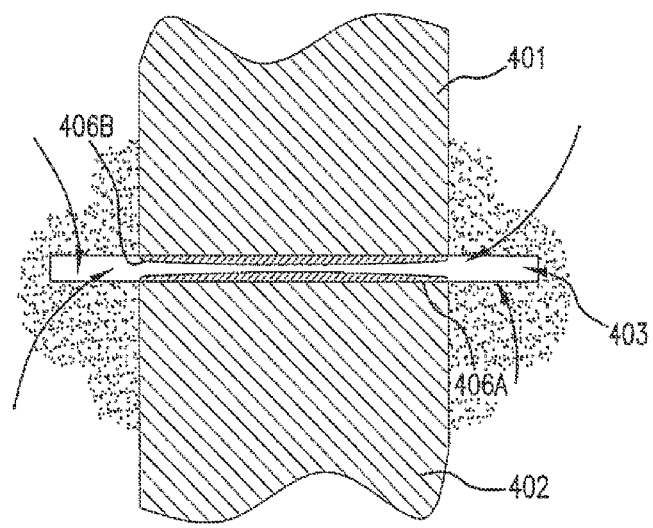
FIGS. 22A and 22B show an electrode comprising chemically deposited layers of conducting metal.
Figure 22B:
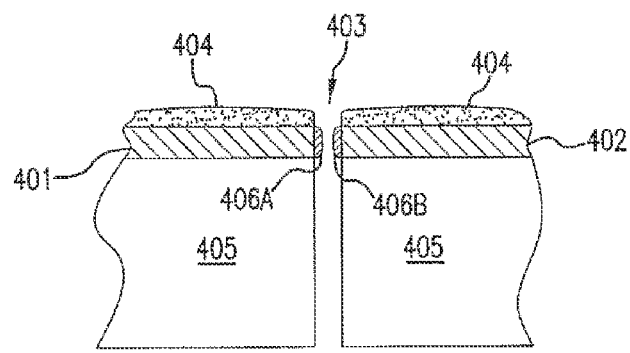

FIG. 22A shows a top view and FIG. 22B shows a cross section of a further embodiment using opposing electrodes. 401 is a first linear metal or doped polysilicon electrode. 402 is a second linear metal or doped polysilicon electrode. 403 is a channel that has been milled through the entire structure. 404 is a protective insulating layer that covers the electrodes. 405 is the underlying insulating substrate. 406A and 406B are electrodes, which may be chemically deposited layers of conducting metal used to achieve a small constriction between the opposing electrodes 401 and 402.

One exemplary manner of assembling the structure of FIGS. 22A and 22B is to make a stripe of doped polysilicon conductor on the substrate 405, then coat over this stripe and the substrate with an insulating layer of oxide, then use a focused ion beam mill to cut a slot through the entire device, separating the stripe of polysilicon into the two opposing electrodes 401 and 402. The channel size resulting from focused ion beam milling is likely to be about 30 nm, so the constriction is narrowed to the desired nanometer dimension by, for example, electric chemical growth of a metal such as gold on to the exposed conducting polysilicon electrodes. This growth can be continued until the junction is short-circuited, and then a small amount of gold removed electrochemically, leaving a constriction of the desired size.

Figure 23:
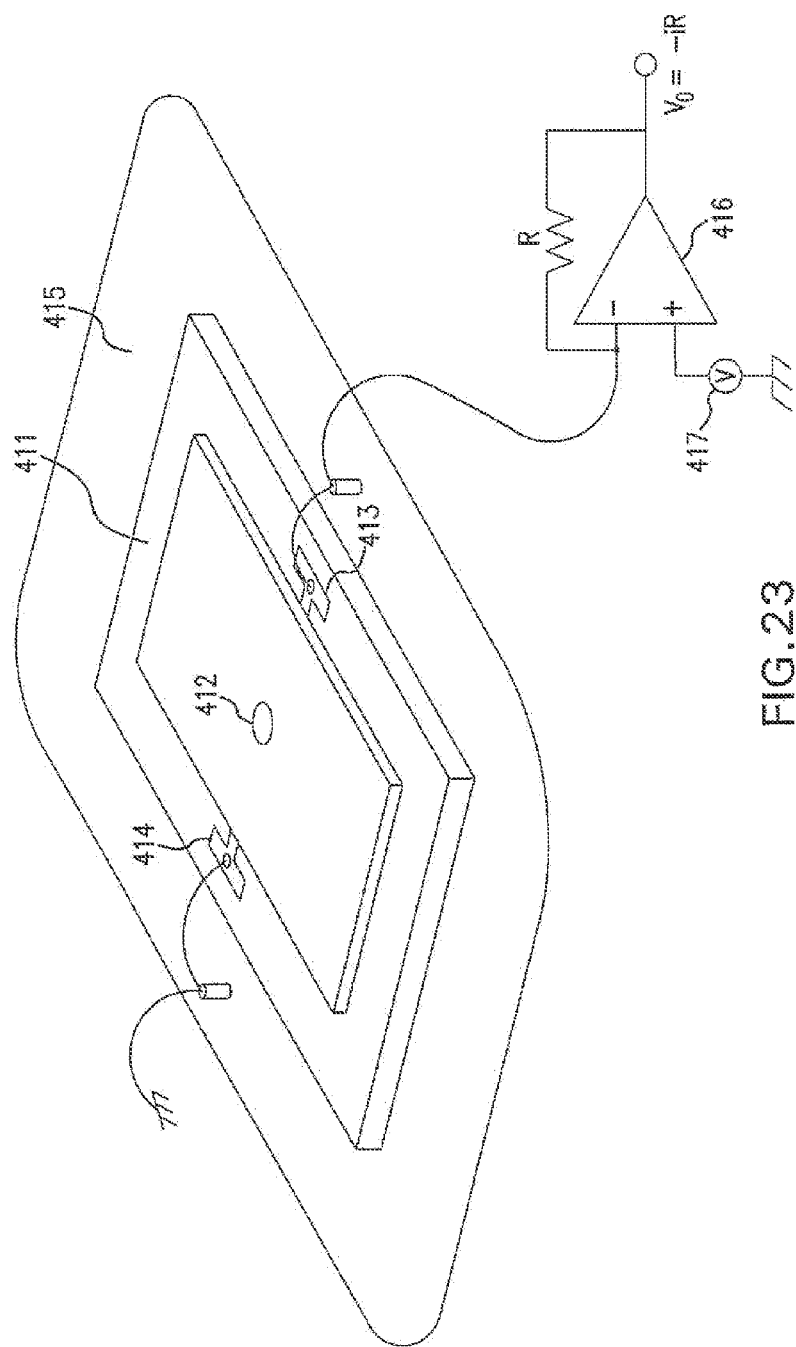
FIG. 23 shows an exemplary electrical arrangement of a device in accordance with one embodiment of the present invention.

FIG. 23 provides an exemplary electrical arrangement embodiment of an apparatus of the present invention. The apparatus comprises a channel 412 formed through a chip 411. Two external connections to the electrodes 413 and 414 are placed on a chip carrier 415 that allows fluid access to the front and back of the channel 412. One electrode 413 is grounded, while the other is connected to the inverting terminal of a current to voltage converter, 416. The non-inverting terminal is connected to a source of bias, 417, so that feedback is applied through the current to voltage conversion resistor R, the inverting terminal is held at a potential of V volts with respect to ground, thus biasing the non-grounded electrode. The output signal of the current to voltage converter 416 is −iR volts where i is the tunnel current signal generated by detection of one or more molecules in the device. Typically V lies in the range from 10 mV to 1V, so that a 1 nS tunnel conductance for a detected molecule would yield a current between 10 pA and 1 nA. With R=1GΩ this leads to output voltages between 10 mV and 1V. The signal to noise of such a detection system may be improved, for example, by using a larger resistor R, but the response time (RCin, where Cin is the electrode stray capacitance) becomes slower. With an R=1GΩ resistor, the shot noise is a tiny fraction of 1 pA, while a stray electrode capacitance of 1 pF (possible with appropriate electrode and instillation design) yields a response time of 1 ms.

In each of the embodiments seen in FIGS. 20-23, it is understood that the various linkers, affinity elements, and the like are connected to the various electrodes to create a functioning apparatus in accordance with the present invention.

Although the present invention has been described to a certain degree of particularity, it should be understood that various alterations and modifications could be made without departing from the scope of the invention as hereinafter claimed.

The chip 2 of the device 100 seen in FIG. 5A may be fabricated in a number of ways.

In one embodiment, a number of such chips 2 may be created at the same time using a single wafer in conjunction with the following principal steps:

Step 1. Grow 100 nm $Si_3N_4$ on the top side of the Si wafer.

Step 2. Photolithographically pattern sensing wires on top of the $Si_3N_4$ using lift-off. The sensing wires will later be cut into two electrodes for each chip.

Step 3. Photolithographically pattern a reference electrode (RE) and a counter electrode (CE) on the underside, the RE and the CE being brought to the edge of the windows (see, e.g., FIGS. 7 & 9).

Step 4. Grow 200 nm $SiO_x$ on both top and bottom to insulate the various electrodes.

Step 5. Pattern and cut windows through $SiO_x$ and Si with HF and KOH etches, exposing part of CE and RE on underside.

Step 6. On FIB, cut through $SiO_x$ and cut sensing wires and shape ends. The gap between the electrodes is about 20 nm. Exposed metal area should be less than a few square microns to minimize leakage current from sensors.

Step 7. Turn chip and FIB mill nanopore through $Si_3N_4$ centered on gap between electrodes. The thus-formed pore is 5 to 10 nm at electrodes. Steps 5 and 6 can be done automatically under computer control for many devices.

Step 8. Clean excess Ga ions from FIB milling with nitric acid.

Step 9. Place gold plating solution below the chip (Si side) and salt solution above it ($Si_3N_4$ side).

Step 10. Plate Au onto sensing electrodes until a predetermined tunnel current is obtained between the two sensing electrodes. If this is coincident with a drop in the pore ionic current (IP) then the electrodes are centered. The parameters may be adjusted so that this process can be automated for production.

Step 11. Open gap by stripping Au to achieve optimal size.

Step 12. Rinse.

Step 13. Functionalize the chips by exposing them to equimolar mix of phosphate grabber and base reader.

Step 14. If specific functionalization is necessary, hold one electrode at >−1V Ag/AgCl and load a first recognition reagent comprising the first affinity element. Rinse and then expose to the second recognition reagent which comprises the second affinity element. Rinse again.

Step 15. Mount chip in device so as to form the lower chamber 5 and upper chamber 6.

It is understood that the wafer may have a large array of such nanopores. In some embodiments, all the nanopores on a wafer may be functionalized in the same exact manner. In other embodiments, however, the nanopores on a wafer need not all be functionalized with the same exact affinity elements.

In one embodiment, the wafer may be considered to comprise an array of 2×2 sub-arrays. Each nanopore in a 2×2 subarray may then have a phosphate grabber (such as guanidinium) as the first affinity element and a different one of the four base readers as the second affinity element. Or in another embodiment, the first affinity element is a base and the second affinity element is a base-pair reader. This way, each 2×2 subarray comprises all four base readers for use in devices configured for "parallel" DNA sequencing. The wafer may then be cut into chips, each chip having a single 2×2. Alternatively, the wafer may be cut into larger chips, each such chip comprising a plurality of such 2×2 subarrays. This redundancy on a chip can increase the certainty of recognition, as discussed further below.

It is understood that multiple 1×4 sub-arrays may be formed instead of 2×2 subarrays. In such case, the wafer may be considered to comprise rows of nanopores whose members are similarly functionalized. For instance, the wafer may comprise a number of rows that is a multiple of four. Each nanopore in a given row may then have a phosphate grabber (or a base) as the first affinity element, and the same base reader (or base pair reader) as the second affinity element. Four rows that are adjacent to one another, may then have a different base reader as the second affinity element in all their nanopores. This allows one to cut up such a wafer into chips comprising a single 1×4 subarray, or even into larger chips comprising a plurality of such 1×4 subarrays.

Each nanopore 1 is functionalized by its associated second affinity element 7 to recognize one of the four bases. Therefore, to sequence DNA, it is understood that either: (a) a single copy of the DNA must pass through a "gauntlet" comprising four differently functionalized nanopores ("serial read"), or (b) four identical copies of ssDNA must pass through four distinct, differently functionalized nanopores ("parallel read").

When a single copy of DNA is used, the nanopores belong to different chips and the DNA is threaded through the four chips. Readouts of the electrical current detected from each of the four nanopores can be aligned, using the known rate of translocation and peak current values signifying a match to determine the DNA sequence.

When four identical copies of DNA are used, it is desirable that they translocate in synchrony. Readouts of the electrical current detected from each of the four nanopores can then be compared to look for peak values signifying a match.

Thus, in one embodiment, a device may be used to sequence DNA by the following set of principal steps:

Step 1. A plurality of such nanopores, each functionalized to recognize one of the four bases, should be provided. This can be done using either serial reads or parallel reads, as described above.

Step 2. Place DNA in lower chamber associated with each such nanopore. Optionally modify the DNA so as to allow entry into the pore from one direction only. In one embodiment, this may be done by tethering the DNA to a bead.

Step 3. Electrophorese the DNA through the pore. If extra pulling force is needed, functionalize the end that passes through pore (after having been modified with e.g., biotin) and attach magnetic bead.

Step 4. Pull DNA through by electrophoresis and/or magnetic bead.

Step 5. Record current pulses (It) as a function of time.

Step 6. Align data from a plurality of reads for each type of base reader.

Step 7. Align data from all 4 reads.

The present invention utilizes the principle of hydrogen bonding for molecular recognition. A number of measurements of hydrogen-bond mediated tunneling using various combinations of bases that form Watson-Crick or mismatch hydrogen bonding have demonstrated the feasibility of this readout.

STM measurements have been made by the present inventors (see FIG. 5 and pages 14-15 of U.S. provisional 61/103, 019). Data measurements of tunnel current as a function of distance were performed by the present inventors (see FIGS. 6-7 and pages 15-16 of U.S. provisional 61/103,019). The present inventors have been able to show that they could distinguish between a G-C and a G-T base pair (one hydrogen bond difference) using the present invention (see FIGS. 8-10 and pages 16-18 of U.S. provisional 61/103,019). The inventors have formed and measured gaunidinium contacts to DNA (see FIGS. 11-14 and pages 18-20 of U.S. provisional 61/103, 019). In addition the inventors have been able to read base compositions from adsorbed DNA (see FIG. 15 and pages 20-21 of U.S. provisional 61/103,019) and have provided a theoretical conformation of the obtained experimental results (see FIG. 16 and pages 21-22 of U.S. provisional 61/103, 019).

Figure 17:
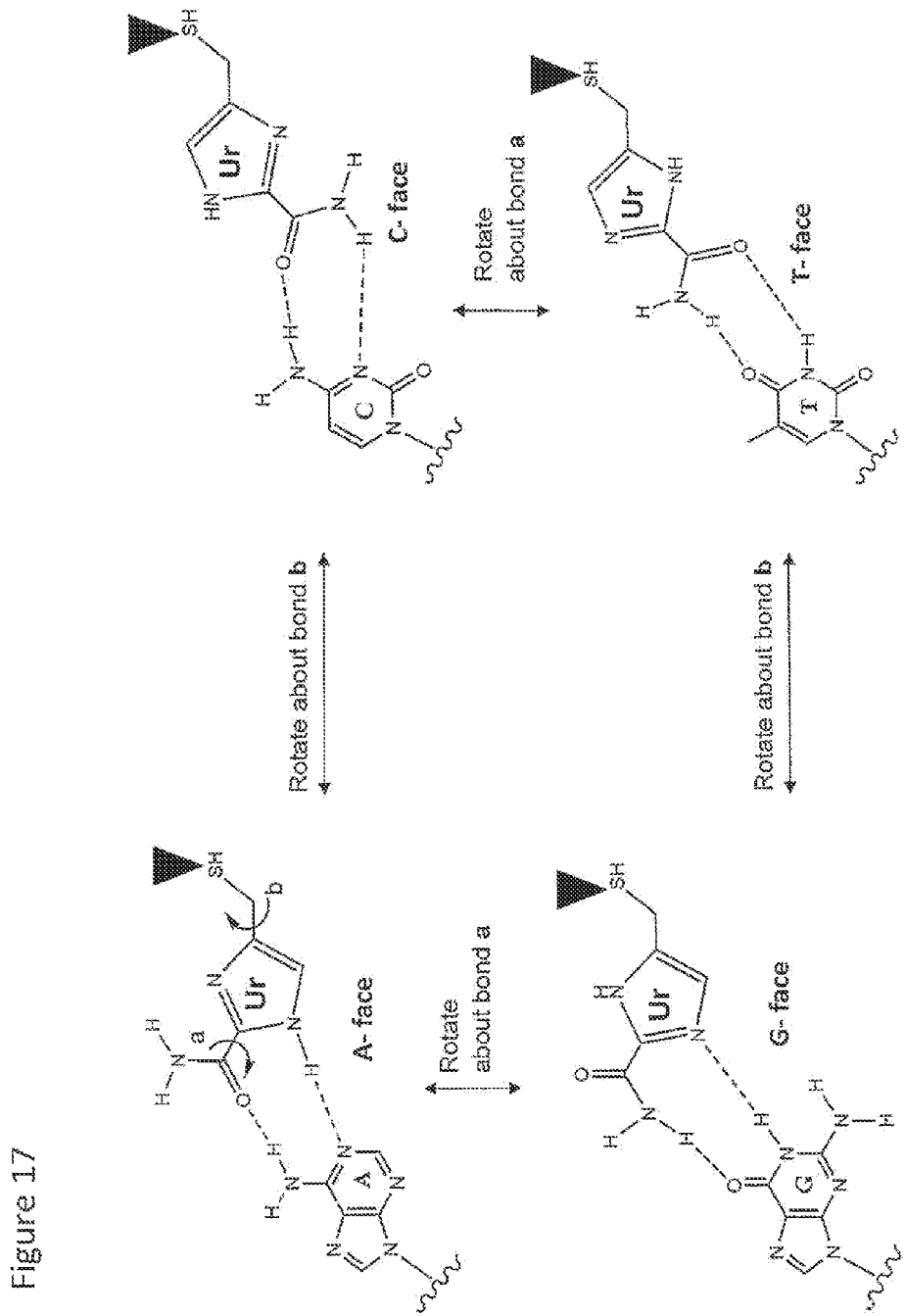
FIG. 17. A universal DNA base reader ($R_U$): hydrogen bonding schematic for 4-(mercaptomethyl)-1H-imidazole-2-carboxamide.
Figure 18:
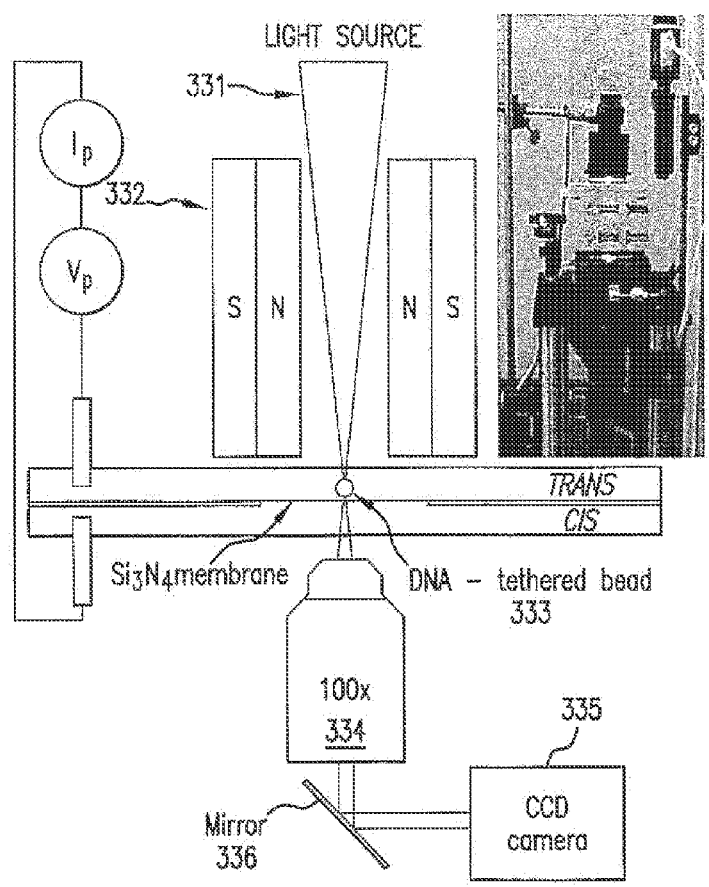
FIG. 18: Magnetic bead apparatus. The CCD can track a bead being pulled into the nanopore to within 10 nm. Inset (upper right) is the prototype laboratory apparatus.

The present inventors have manufactured and tested nm wide tunnel gaps (see FIG. 17 and page 24 of U.S. provisional 61/103,019) and tested the gaps for a recognition response (see FIG. 18 and page 24 of U.S. provisional 61/103,019). In some embodiments, is preferred that that tunnel gap is sized to correspond to a conductance minus the bridging molecule of 0.012 nS.

The inventors have also optimized electrode functionalization (see pages 24-25); optimized electrochemical fabrication of the device (see page 25); characterized electrode stability (see page 25); and have shown active control of the tunnel gap (see FIG. 20 and pages 25-26 of U.S. provisional 61/103, 019).

Generation of Molecular Recognition Signals in a Tunnel Gap Fabricated on a Chip; Optimization of Electrode Design and Fabrication The problem of how to make 'molecular alligator clips' has consumed the molecular electronics community for decades. The problem now appears to have been solved in flexible junctions (like the STM where one electrode is controlled with sub precision) but it is extremely difficult for fixed junctions, at least in the case of single molecules. One reason is that the outermost atoms of each electrode must be in precisely the correct position to satisfy the bonding requirements of the molecule that spans the gap. Some successful experiments have been reported using electromigration, a technique in which a nanogap is formed by "blowing" a fuse consisting of nano-scale neck in a wire. But the same technique has been shown to mimic molecular electronic effects in the absence of molecules owing to the presence of complex metal structures in the gap. The requirements for atomic precision in bonding molecules are mitigated in the embodiment of FIG. 5 because of the use of flexible linkers as part of the tunnel junction. This is possible because the embodiment of FIG. 5 depends on a binary "signal-no signal" output rather than on an absolute conductance of the gap. Thus, reliable manufacture of "clean" gaps of about 2 to 3 nm in size range and chemical functionalization of these gaps for reliable readout, are both realizable.

FIG. 6A-6B shows the results of a different approach to electrode design and the formation of gaps between electrodes. The technology employed to manufacture and inspect such "clean gaps" has undertaken a significant leap as a result of the work of Marija Drndić at the University of Pennsylvania. By using electrodes placed on very thin membranes (exactly as required for nanopores) Drndić's group has been able to image junctions using transmission electron microscopy (TEM) to atomic precision. Moreover, Drndić's group has shown that the lack of electron backscatter in thin-film supports permits very high resolution electron-beam ablation of metal structures.

Another approach to electrode design and the manufacture of nanogaps is electrochemical deposition and stripping. Electrochemical generation of nano-gaps has been in use for some years but may sometimes be unreliable.

The present invention also takes advantage of a new approach to electrochemical generation. In one embodiment of the present invention, reference (RE) and counter (CE) electrodes are incorporated into the chip itself, spaced a few microns from the tunneling gap.

FIG. 7A-7D shows a prototype test-bed large-electrode junction (i.e., large electrodes, small gap) in accordance with one embodiment of the present invention. Gold electrodes that are 2 μm wide by 30 nm high are patterned by lift-off onto a 200 nm thick $SiO_2/Si_3N_4$ substrate in a cruciform pattern. One electrode is a continuous strip that is cut to form the two sensing electrodes (SE1, SE2), which also serve as the working electrodes for gold deposition and stripping. Two other electrodes (RE, CE) are separated from the central wire by gaps of 3 μm and they serve as built-in counter- and reference-electrodes. The electrodes are covered with a 200 nm thick layer of $SiO_2$. The wafer, containing 25 arrays, each of nine devices, is taken to the focused ion beam mill (FIB) where a trench is cut across the central wire to form the two sensing electrodes (SE1 and SE2). The trench is widened and continued out to the RE and CE electrodes to form microfluidic channels in communication with both sensing electrodes and the CE and RE. As a consequence of the geometry of the ion-beam milling, a 100 nm wide trench at the top of the $SiO_2$ corresponds to about one to two nm gap in the gold electrodes. As a result, once the gap is chemically-cleaned of excess Ga ions, stable and somewhat reproducible tunnel gaps are formed.

Figure 8A:
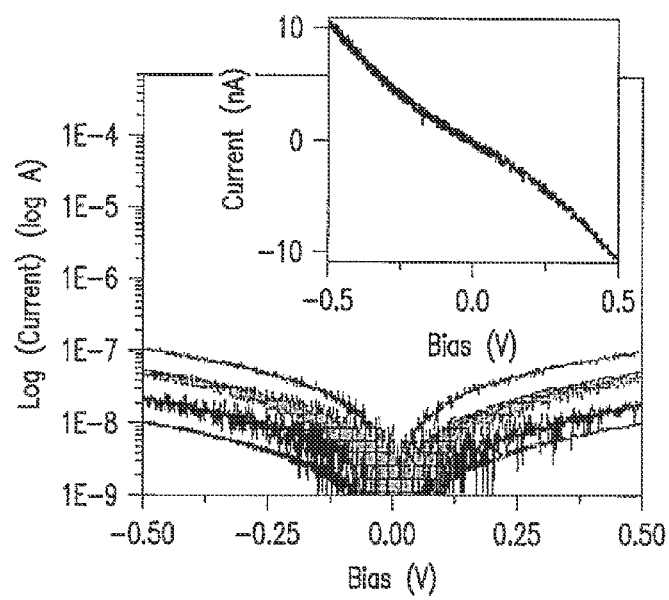
FIG. 8A-8B.
Figure 8B:
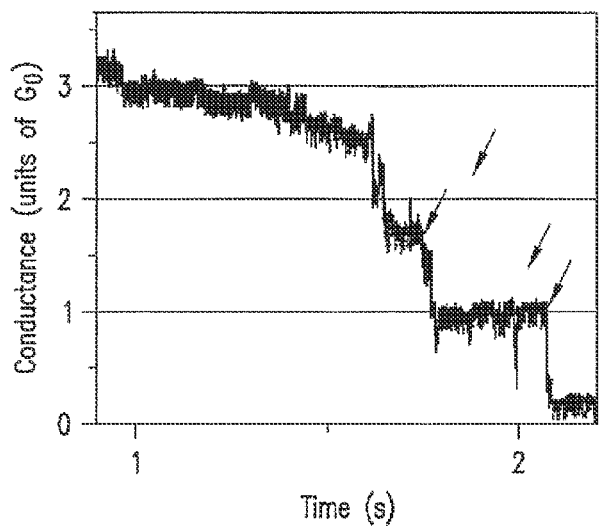

FIG. 8A, which plots the log-current vs. bias voltage data (and the linear data shown in the inset), confirms the presence of such tunnel gaps. Fits of these data to the Simmons formula yield gap dimensions that are on the order of one nm. By placing a drop of gold-plating solution in the gap and controlling the deposition galvanostatically, while monitoring the tunnel current, $I_t$, it is possible to close the gap. Once closed (as detected by current between SE1 and SE2) controlled stripping opens the gap with atomic scale control.

FIG. 5B, which plots conductance as a function of time after the gaps are closed, shows quantum steps in conductance (indicated by arrows) that characterize atom-sized filaments of gold. Thus atomic-scale control of gap size can be achieved by electrochemical deposition and stripping.

Alignment of a Nanogap Electrode Pair with a Nanopore.

Assembly and alignment of the reading head, comprising a pore and electrodes can be achieved through electrochemical self-assembly of electrode pairs. Electrochemical deposition of electrodes minimizes the number of one-off nanofabrication steps, resulting in devices that are easier to manufacture. Furthermore, an electrochemical approach makes it possible to strip and reuse electrodes, a possible cure for failure modes related to electrode geometry and functionalization. This also reduces costs and enhances reliability.

Figure 9:
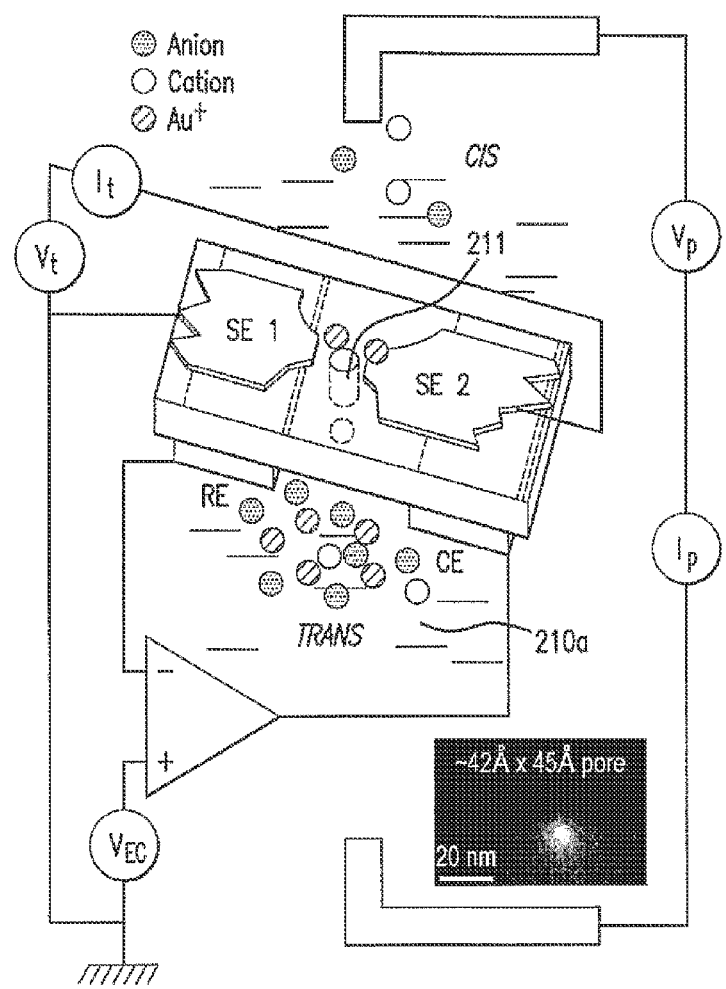
FIG. 9: Scheme for through-pore plating (showing a nanopore made by TEM shrinkage as an inset, lower right). The key feature is through-pore transport of Au+ ions, localizing deposition to parts of the sensing electrodes (SE1, SE2) in close proximity to the pore. Metal deposition and stripping is controlled by the built in counter electrode (CE) using the built-in reference (RE) with the sensing electrodes serving as working electrodes (operated at a small potential difference, $V_t$). VEC sets the potential of the working electrodes. Measurements of pore current ($I_P$) and tunnel-current between the two working electrodes ($I_t$) is used as control parameters for final pore size and tunnel-gap size. The two data sets together can be used to center the electrodes in the pore.
Figure 10:
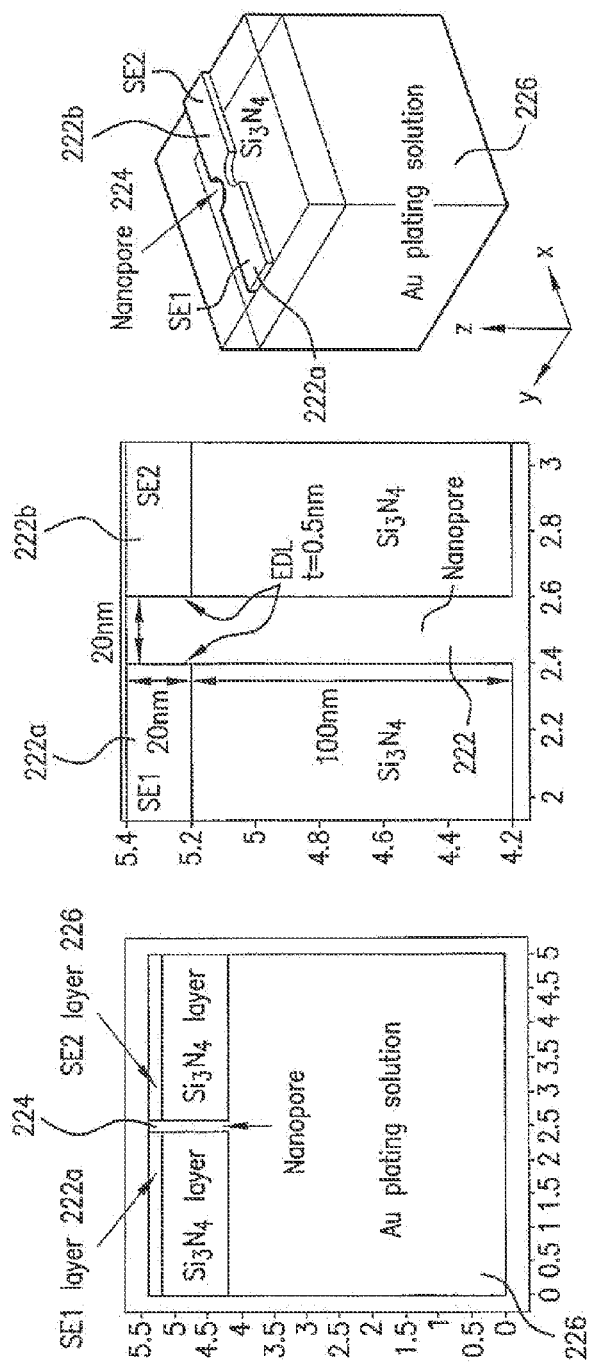
FIG. 10A-10C: Models for finite element analysis. 10A-10D model of the electrodeposition setup. 10B—A close-up including the double layer (EDL). 10C—Full 3D model of the electrodeposition setup including EDL structure.

FIG. 9 presents a strategy for controlled growth of electrodes into the gap, in accordance with one embodiment of the present invention. The deposition process is controlled from the trans solution 210a compartment so that deposition is localized to the region in the immediate vicinity of the pore 211. In addition to the electrode starting geometry, other factors affecting this process are reagent concentrations, electrode potentials and pore geometry. The process is complicated by the high resistance of the pore. Simulations and TEM measurements can be used to characterize real junctions to optimize the process of forming the electrodes. Meller's TEM approach can be advantageously employed to produce small pores, but it may also be possible to eliminate the TEM "filling" step. While the electrode gap can be quite large, the nanopore 211 must be small enough to permit only one DNA strand to pass at a time. Therefore, alternatives to TEM could greatly simplify the production of reading heads. Recent reports of controlled formation of pore as small as 5 nm by FIB indicate that one may start with a 20 nm pore cut into a 20 nm constriction to form the two sensing electrodes (the starting geometry shown in FIG. 10C). One can mill through a thin $Si_3N_4$ from beneath the electrodes (which are visible in the dual-beam FIB through the membrane). The gold electrodes can then be electroplated out into the gap, narrowing both the gap and the pore to the desired size (~2 to 3 nm). Optimizing pore size can be advantageous given that smaller pores result in greater DNA-pore interaction while distinct ssDNA translocations have been observed in rather large pores. In the event that a small (<2 nm) pore is required to ensure translocation of only single strands, or to remove secondary structure, one may start with pores that have been "shrunk" on the TEM.

A computational approach can be used to simulate the electrochemical processes in three stages: (1) 2D modeling of the electrodeposition process ignoring double-layer effects. (2) Subsequent inclusion of double layer effects. (3) Finally, a full 3D model including the double layer. See FIGS. 21-22 and pages 27-29 of U.S. provisional 61/103,019.

Design and Synthesis of DNA Base-Readers

Elimination or reduction of base-pairing mismatches simplifies the robustness of the sequencing. This can be realized by using more specific DNA Base-Readers. Better affinity elements based on chemical principles and theoretical modeling help with the design of recognition reagents. Once synthesized, affinity elements can be readily and rapidly characterized using STM methods, such as those described herein.

Each of the four bases has a distinguishable Watson-Crick edge, allowing one to design a reader for each of them. (See FIG. 23 of U.S. provisional 61/103,019). Four separate readers are likely to be required, although it may also be possible to employ a "universal reader" having a particular structure. A set of candidate structures can be screened to determine their specificity and immunity to mispairing. A DNA base reader should have the following chemical and structural features: (1) donor and acceptors sites for formation of stable hydrogen bonds; (2) planar n system capable of stacking interactions and efficient mediation of tunneling; (3) the molecules must be constructed such that the Watson-Crick base pairing occurs with high specificity; (4) they could incorporate steric obstruction of mismatches; and, (5) should be stable to oxygen, light, water, and electrochemical reactions, once coupled to the electrodes. It is best to reduce manipulations of the target DNA (such as incorporation of modified nucleotides by enzymes) to a minimum in view of the goal of reading long, native DNA.

Electronic structure calculations can be carried out prior to synthesis both to verify the proposed bonding, and to test the effects of altering the structure of the heterocyclic rings on electronic conductance.

The Adenine Reader (A Reader)

Figure 24:
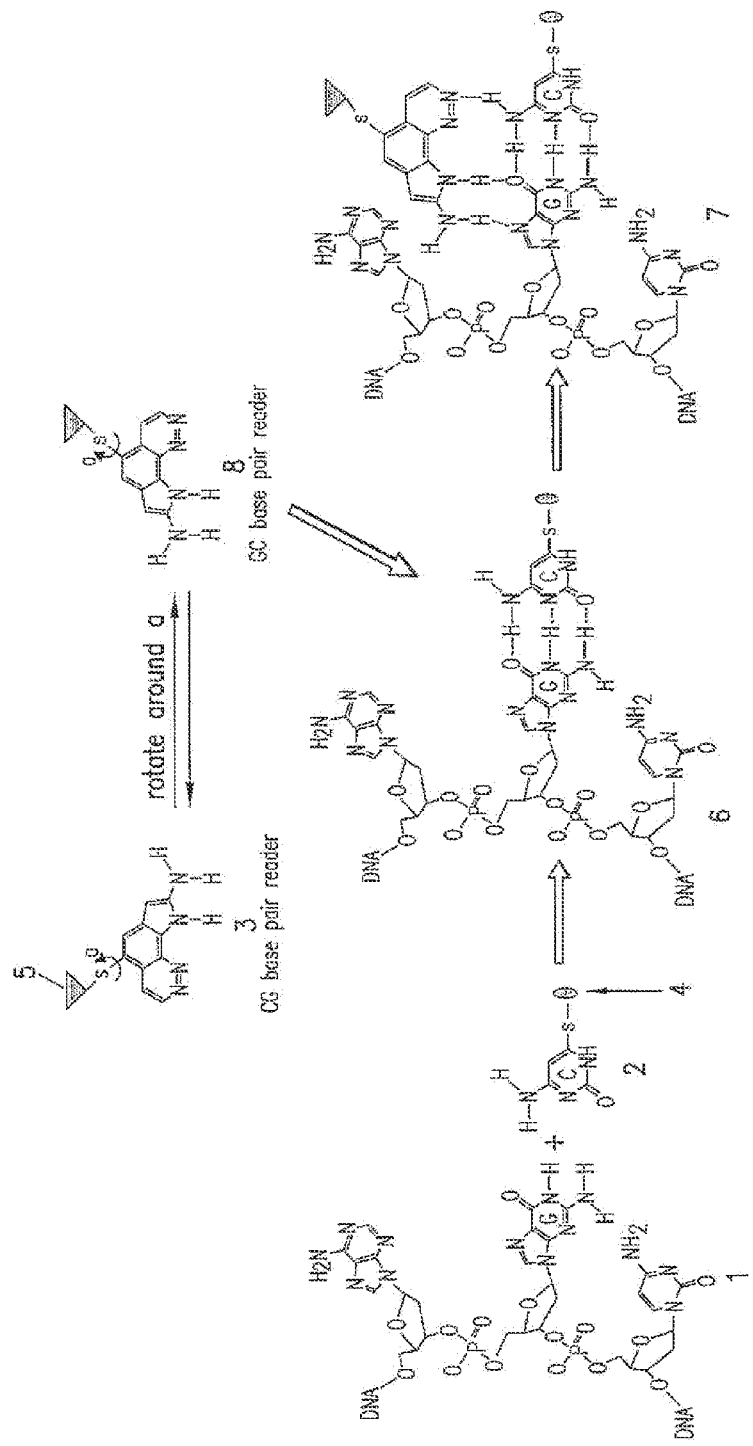
FIG. 24 shows one embodiment of the invention where a G-C or C-G base pair reader forms a triple hydrogen bond with the G base present on the DNA strand and the C base reader attached to one electrode.

A commercially available 5-mercaptouracil may be used as an Adenine reader. 5-mercaptouracil can form a Watson-Crick base pair with adenine, but it can also mispair with other DNA bases C, G, and T (see FIG. 24 of U.S. provisional 61/103,019). Because each of these mismatched base pairs has a similar hydrogen bonding pattern to the Watson-Crick base pair, it may be very difficult to distinguish them electronically, making adenine the most difficult base to identify unambiguously. This problem is not necessarily fatal if high fidelity data are available from the three other readers, but a selective A-reader is highly desirable.

Figure 11:
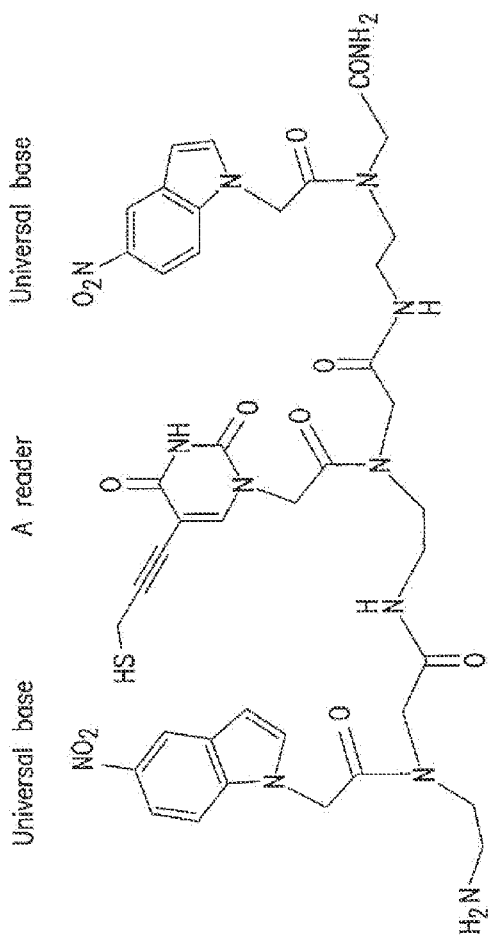
FIG. 11. Structure of a PNA trimer composed of modified uracil and universal bases.

FIG. 11 shows a peptide nucleic acid (PNA) trimer comprising one modified uracil flanked with universal bases, which may be synthesized. Such a PNA may serve as a selective A-reader. PNA is a structural mimic of DNA but it forms more stable DNA duplexes and is more sensitive to mismatches than its DNA counterpart. By using a PNA trimer for recognition, one may convert a single base pairing process into a DNA-PNA hybridization process. Thus, the base pairing specificity of modified uracil relies not only on hydrogen bonding but also on stacking with its nearest neighbors. The additional stacking interaction promotes the preorganization of the base reader into the "right" conformation for Watson-Crick base pairing. Universal bases form base pairs with normal DNA bases indiscriminately so the PNA trimer should have no selectivity to the (n−1) and (n+1) flanking bases on the target DNA. It has been demonstrated that a universal base can enhance the mismatch discrimination in the DNA duplex thermodynamically and enzymatically. In one embodiment of the structure, a propargylthiol linker is attached at 5-position of uracil for connection to the electrode. In the event that this linker is not long enough, another "molecular wire" may be used. The PNA trimer can thus be tested against a series of adenine centered DNA trimers with varied base contexts at their two ends on gold substrates using the STM method. Such a strategy may also be applied to the design of other base readers.

The PNA trimer can be synthesized manually or in an automated peptide synthesizer. The synthesis of universal base PNA monomer has been reported in the literature The modified uracil PNA monomer may be synthesized starting from 5-iodouracil-1-acetic acid. The starting material reacts with ethyl N-[2-Boc-aminoethyl]glycinate, providing a 5-iodouracil PNA monomer that can be converted into the desired product through the Sonogashira coupling with 3-benzoylthio-1-propyne followed by treating with di-tbutyl-1-(tbutylthio)hydrazine-1,2-dicarboxylate.

The Cytosine Reader (C Reader)

FIG. 12 illustrates that 8-Mercaptoguanine can serve as a C reader. Guanine in general forms stable mismatched base pairs such as G-G, G-A, and G-T. Ideally, however, these mismatches would be reduced. Sekine and coworkers have demonstrated that 2-N-acetyl-3-deazaguanine (a2c3G) is more selective to cytosine than guanine (see FIG. 13), and also destabilizes the GA mismatch. Compared to guanine, one of the undesired hydrogen bond acceptors is removed and the rotation of the $NH_2$ group is constrained in a2c3G.

Figure 13:
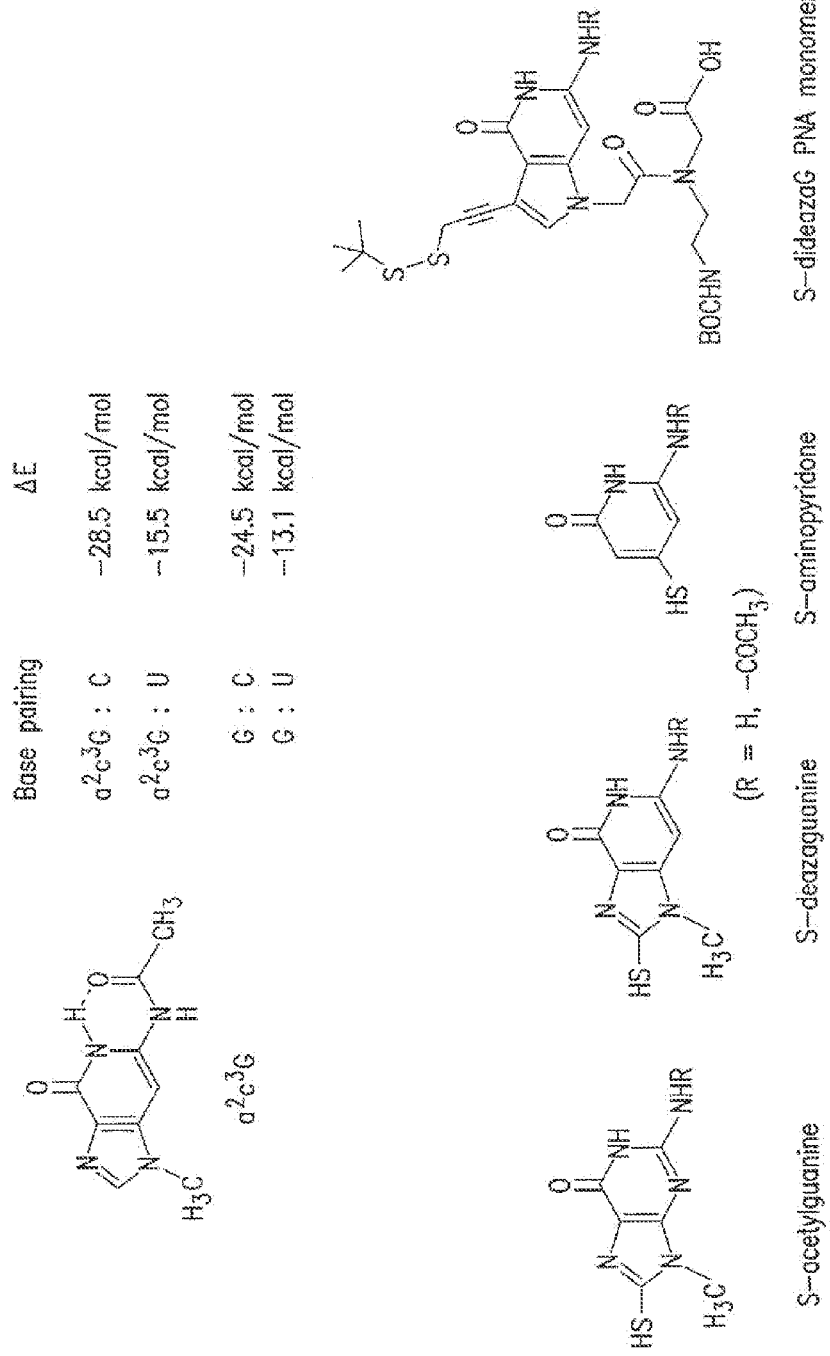
FIG. 13. Proposed structures of modified guanines for improving specificity of the C reader.

FIG. 13 shows a number of modified guanines which, based on the work of Sekine, may serve as C readers. A common feature of these molecules is that their Watson-Crick edge remains unchanged and the undesired atoms are left out. S-acetylguanine is an amine-acetylated derivative of 8-mercaptoguanine, which can be used to determine how acetylation of the amine affects the specificity of the guanine. With this control, S-deazaguanine, a deaza derivative of 5-acetylguanine (with the 3-nitrogen removed) should reduce the sheared G-A mismatch. S-aminopyridone is the simplest candidate C reader and it should have the highest specificity. A PNA trimer containing 3,7-dideazaguanine (S-deazaG) is potentially useful for this purpose as well.

S-acetylguanine can be synthesized starting from 9-methyl-8-mercaptoguanine. The thiol group is first protected in a tbutyl disulfide form, and then the starting material treated with acetyl chloride followed by Al—$NiCl_2$-THF. The synthesis of S-deazaguanine is straightforward using 3-deaza-9-methyl-guanine as the starting material. S-aminopyridone can be synthesized starting from 4-iododiamonopyridine prepared according to the reported procedure. First, 4-iodo-6-acetylaminopyridone can then be synthesized by adopting the method used by Sun et al, and then converted to the desired product by treatment with thiourea. The key step in synthesis of S-dideazaG PNA monomer is iodonation of dideazaguanine. The approach developed by Ramzeva and Seela can be employed for this. If such an approach is found to have a selectivity problem, one may first prepare 7-iododidazaguanine using the regioselective reaction controlled by a bulky group at 9-position of dideazaguanine and then convert it to the desired product.

The Guanine Reader (G Reader)

Figure 14:
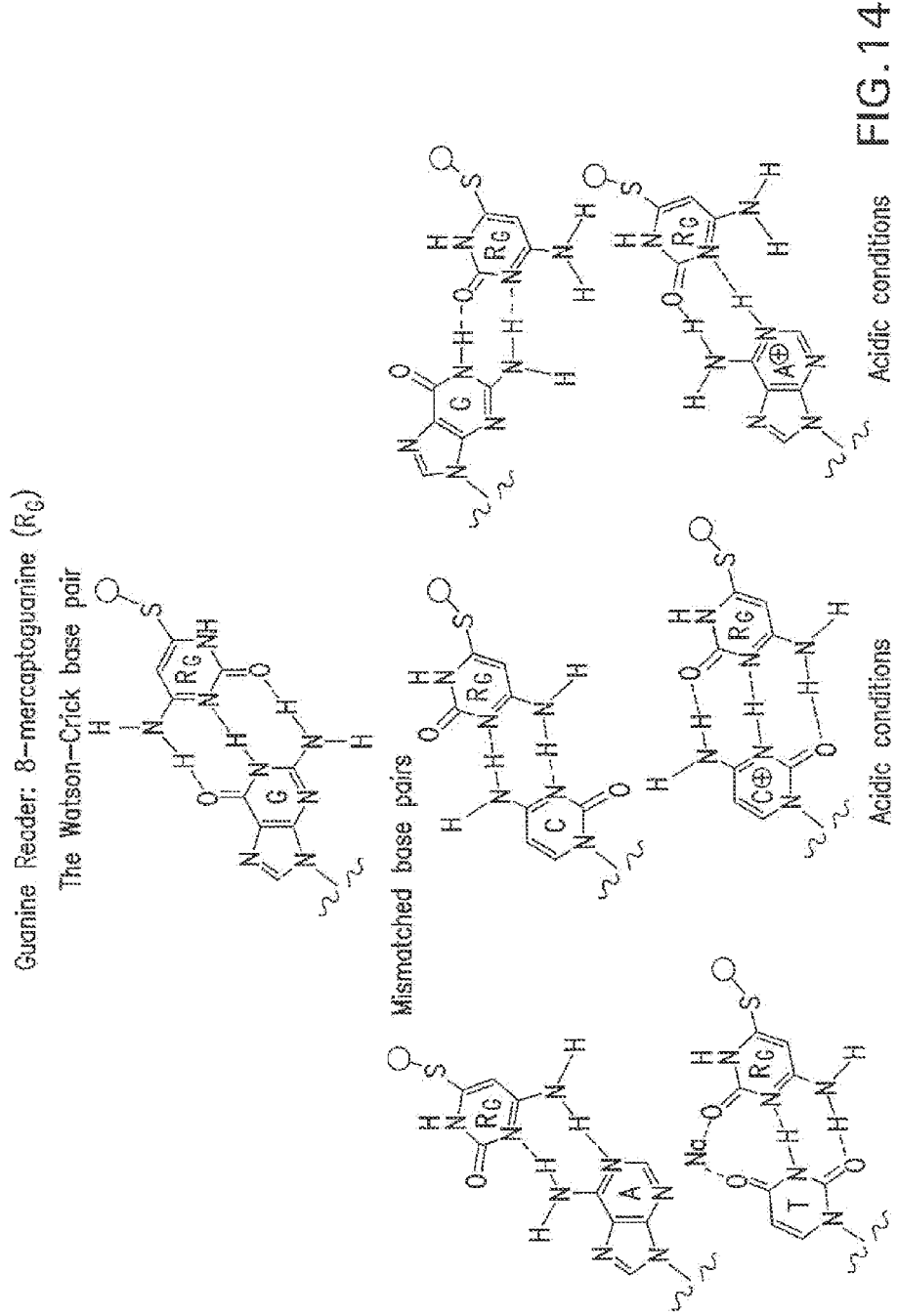
FIG. 14. Base pairing of the guanine reader ($R_G$) with natural DNA bases.

In one embodiment, 6-Mercaptocytosine, a cytosine derivative, can be used as a G reader. FIG. 14 shows that 6-Mercaptocytosine should form a more stable base pair with guanine compared to the mismatches in neutral conditions. Other candidates include 5-mercaptocytosine, 5-mercapto-1-methylcytosine, 6-mercapto-1-methylcytosine, and 1-(2-mercaptoethyl)cytosine, which can easily be synthesized from commercially available starting materials. Studies of these molecules allow one to optimize the G reader attachment and to determine how the N−1 methylation of cytosine affects its specificity. The effects of pH on the recognition of the G reader should also be taken into consideration. It is known that protonation on DNA bases enhances the stability of mismatched base pairs. Under slightly acidic conditions, Cytosine forms stable hydrogen bonded base pairs with protonated cytosine (C+) and adenine (A+). The protonation alters the electronic structure of DNA base pairs, resulting in changes of their electronic properties. Thus, pH is a factor in achieving a high specificity. The electrode side of the pore may be somewhat basic owing to the polarization of the pore used to translocate the DNA into the cis chamber.

Figure 15:
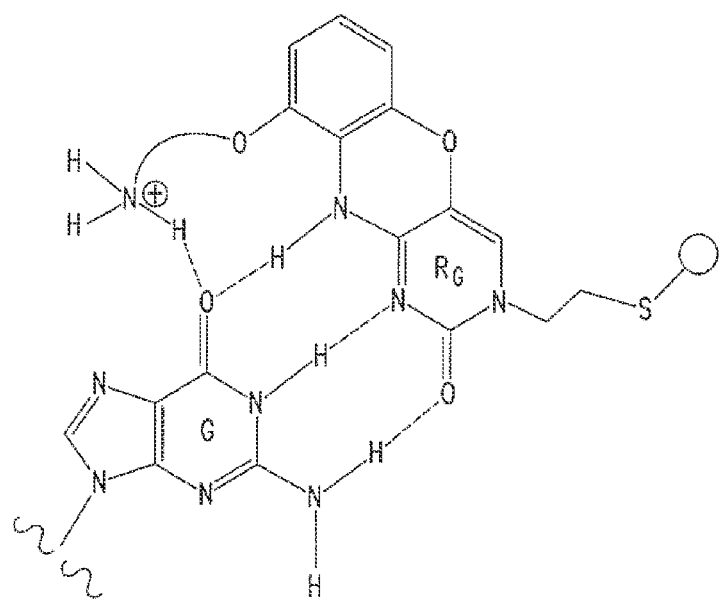
FIG. 15. Basepairing of the G-clamp with guanine.

FIG. 15 shows the basepairing of a tricyclic cytosine analogue (called a "G-clamp" with guanine. Lin and Mattecucci have reported that such a G-clamp can simultaneously recognize both Watson-Crick and Hoogsteen edges of a guanine when it was incorporated into DNA (FIG. 15). The G-clamp has shown a higher specificity than its counterpart, 5-methylcytosine. The G-clamp may also be evaluated for its suitability as a G reader. A thiolated G clamp can be synthesized based on a procedure published by Gait and coworkers.

The Thymine Reader (T Reader)

In one embodiment, 2-amino-8-mercaptoadenine, a derivative of 2-aminoadenine (DAP), can be used a T reader. FIG. 16 shows that DAP forms a more stable Watson-Crick base pair with thymine due to an additional N—H···O hydrogen bond. However, it has been reported that stability of the DAP-T base is sequence dependent in DNA, which is attributed to varied base-stacking interactions. Thus, a individual DAP coupled to an electrode should recognize thymines in a single stranded DNA with high selectivity, generating distinguishable electronic signals. DAP can form mismatched base pairs with C and A. Other types of mismatches, such as Hoogsteen base pairs, can also occur. As shown in FIG. 16, one may employ three analogues of diaminopurine to improve its specificity and affinity to the thymine base. 2,6-Diacetamido-4-mercaptopyridine, which can be synthesized by treating 2,6-diacetamido-4-iodopyridine with sodium hydrosulfide, is a simple DAP analogue which is more specific and stable. In general, the DAP-T base pair is less stable than the G-C base pair. Recently, Brown and coworkers reported an analogue of adenine, 7-aminopropargyl-7-deaza-2-aminoadenine, which could form an "A:T" base pair with stability comparable to G:C. One may therefore test the base pairing specificity and stability of its analogues 7-deaza-2-aminoadenine and 3,7-dideaza-2-aminoadenine by incorporating them into the PNA trimer, respectively. The corresponding PNA monomers can be synthesized from commercially available starting materials 6-Chloro-7-deazaguanine and 4,6-dichloro-1H-pyrrolo[3,2-c]pyridine using chemistries described above.

A Universal Reader

The present invention provides a universal reader and the use of a universal base reader in DNA sequencing. The universal base reader is capable of recognizing the four natural DNA bases with distinguishable signatures such as 4-(mercaptomethyl)-1H-imidazole-2-carboxamide. It includes two hydrogen bonding donors and two hydrogen bonding acceptors, one half on the aromatic imidazole ring and the other half on the amide side group. The molecule can be attached to the electrode through the thiol group.

FIG. 17 shows that the amide group is relatively free to rotate around bond a, and the whole imidazolecarboxamide can freely rotate around bond b. In the solution, the molecule exists in a mix of varied conformations. FIG. 17 also illustrates how this molecule base-pairs with each of DNA bases in a different conformation. This universal base is capable of forming two specific hydrogen bonds with all four bases indiscriminately. See FIG. 17. In the same manner, the universal reader can hydrogen bond with methylcytosine in DNA. Each of the conformations can be formed by free rotating the sigma bonds, so one may expect that each base pair has a similar free energy. However, the second universal base interacts with the universal-DNA base pairs differently (see FIG. 56). Thus, it may be possible to read unique signals out of the tunneling device.

The synthesis of 4-(mercaptomethyl)-1H-imidazole-2-carboxamide starts from (1-trityl-1H-imidazole-5-yl)methanol. First, the hydroxyl group can be converted to t-butyldisulfide as a latent thiol function, and then a cyano group introduced to 2-position of the imidazole ring, which can be hydrolyzed to carboxamide. Finally, the desired product can be obtained by detritylation and reduction of the disulfide.

Figure 55:
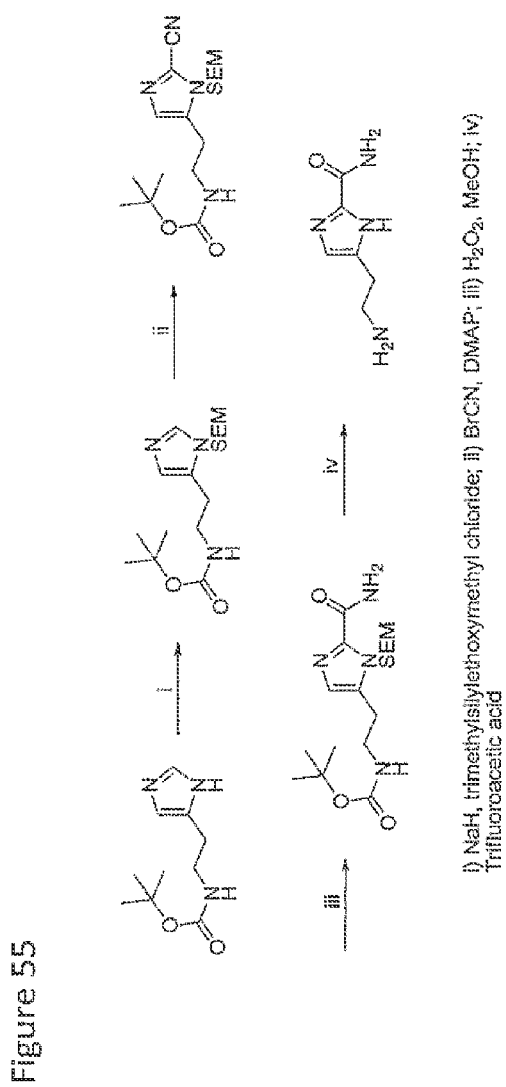
FIG. 55 provides a synthesis scheme for a universal base reader.

The present invention also provides another universal base reader: 5-(2-aminoethyl)-1H-imidazole-2-carboxamide. FIG. 55 shows a synthesis scheme for the universal reader 5-(2-aminoethyl)-1H-imidazole-2-carboxamide. Starting from amine-protected histamine (1), the imidazole ring is protected with 2-(trimethylsilyl)ethoxy)methyl group (SEM) (2), and then a cyano group is introduced to its position by treatment with 1-cyano-dimethylaminopyridinium bromide (3). Hydrolysis of the cyano group with basic hydrogen peroxide and removal of protecting groups will furnish the desired compound 5-(2-aminoethyl)-1H-imidazole-2-carboxamide (4).

For theory and modeling of base readers, see page 34 of U.S. provisional 61/103,019, which is incorporated by reference.

FIG. 56A shows that two universal readers can form triplexes with DNA bases through hydrogen bonding. In these triplexes, the universal reader interact with DNA bases differently so that each triplex generates a different current signal responding to a individual DNA base. The universal base reader can be used in the systems described herein for DNA sequencing in conjunction with a nanopore/carbon nanotube. The universal base reader is tethered to a nanopore and the ion current through the nanopore measured as DNA passes through it, stalling for delay times characteristic of the strength of binding to each base to the universal base reader. This readout is analogous to that demonstrated for a protein nanopore functionalized with a cyclodextrin adaptor (See Clark et al., Nature Nanotechnology, 2009. 4:265-270).

Figure 56:
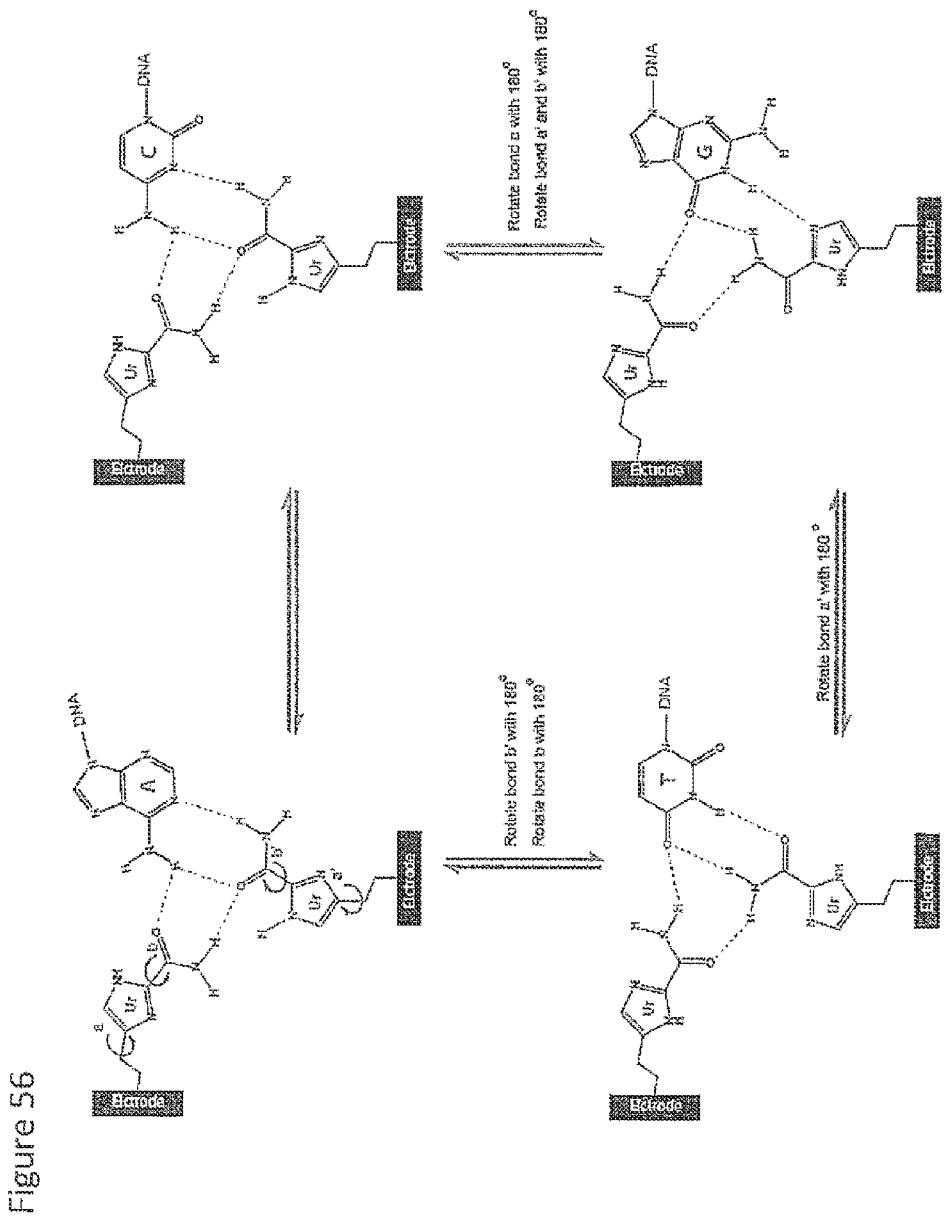
FIG. 56 provides a schematic diagram of DNA base recognition with the use of two universal base readers (designated as Ur). Pairs of electrodes, each functionalized with a universal base reader, will trap each of the bases in complexes that form a tunneling path across the electrode.

By using a pair of universal base readers, (one universal base reader attached to one electrode and a second universal base reader attached to a second electrode), preferably in any of the devices or methods disclosed herein or in PCT/US09/37563, filed on Mar. 18, 2009, one can read tunnel current across recognition complexes (shown in FIG. 56). The universal base pair reader may be coupled to single walled carbon nanotubes (SWCNT) by means of a primary amine tethered to the heterocylic ring by a short, but flexible ethylene linker. Covalent attachments to the ends of the carbone nanotube is carried out using EDC and sulfo-NHS as activating agents to couple the primary amine to the carboxylate residues induced by $O_2$ plasma etching of the SWCNT.

Thus, the universal base reader recognizes all bases and forms an additional set of hydrogen bonds with the complex of the base and another universal base reader so that a base can bridge the gap between two electrodes functionalized with the same type of universal base reader.

Figure 57:
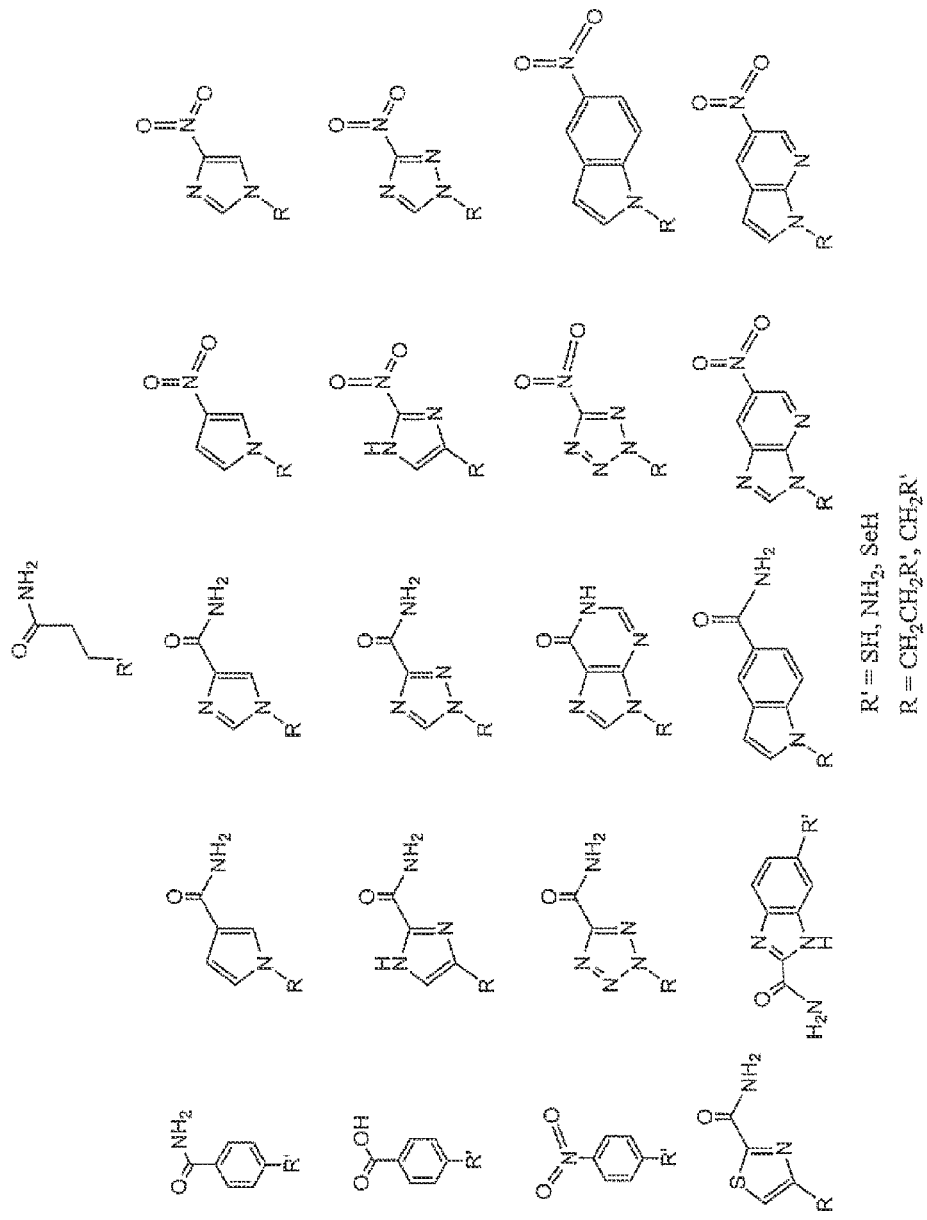
FIG. 57: provides examples of compounds that can function as a universal reader.
Figure 58A:
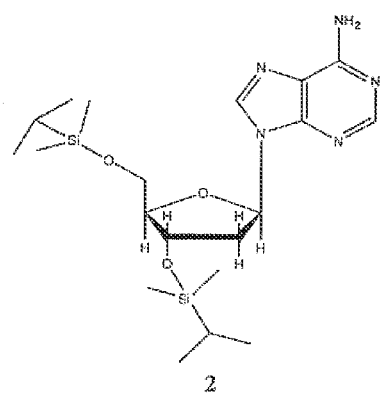
FIG. 58a provides the structure of an exemplary modified adenosine for use in an organic solvent (the OH groups in the deoxyribose ring were functionalized with t-butyldimethyl-silyl) (TBDMS).
Figure 58B:
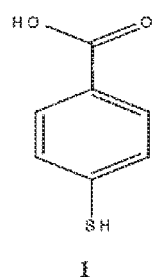
FIG. 58b provides the structure of one universal base reader, thiobenzoic acid.

The present invention also provides universal base readers shown in FIG. 57 and FIG. 58b (thiobenzoic acid). By using a universal base reader, this removes the need for selective functionalization of the nanoelectrodes. In addition, as seen in Example 6, use of a universal base reader may reduce or remove the need for sequence assembly (example 6 shows that at least two bases could be read with only one gap).

Base-Pair Readers

The present invention further provides an embodiment where devices of the present invention utilize a first recognition element comprising a base that will recognize and bind to its Watson-Crick complement (i.e. A, G, C or T) and a second recognition element comprising a base-pair reader discussed herein below. This provides a new method for forming chemically-specific chemical contacts so DNA, by forming self-assembled hydrogen bonded contacts across each base pair. It is based on the ability of certain reagents to form multiple, selective hydrogen bonded contacts to pairs of bases. See Doronina, S. O. and J.-P. Behr, Towards a general triple helix mediated DNA recognition scheme. Chemical Society Reviews, 1997. 26: p. 63-71; Fox, K. R. and T. Brown, An extra dimension in nucleic acid sequence recognition. Quarterly Reviews of Biophysics, 2005. 38: p. 311-320.

The inventors have determined that absolute tunnel conductance for A-Thymdine, 2AA-Thymidine and G-deoxythymidine and have used this data to understand and design an optimal fixed tunnel gap for readouts of DNA basepairs. There is very small conductance across an entire DNA molecule so obtaining electronic sequences of DNA utilizes readout schemes that involve short tunneling paths, such as those obtained with the use of base-pair readers (as one recognition element) and a base reader or base as the other recognition element.

Figure 38C:
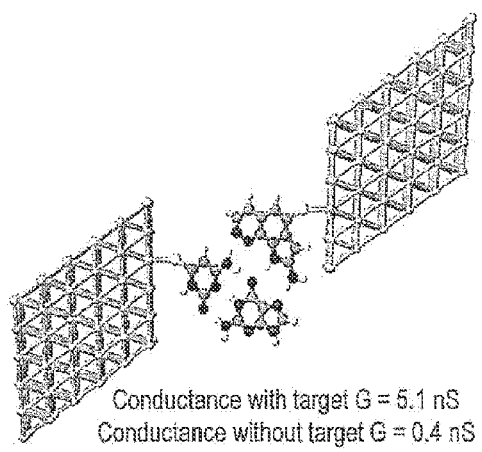
FIG. 38: Trans-base-pair readers in action. The readers (red) are attached to one electrode with a base (blue) attached to the other. A Watson-Crick complement on the target DNA strand results in complex stabilized by 6 hydrogen bonds for G, C and T targets and 5 for an A target. The H-bond structures shown are the lowest energy structures found in quantum-chemical simulations. The arrangements shown here are for a T-target (A) and a G-target (B). An A-target is read by replacing the 2AA on the second electrode with T in (A) and a G-target is read by replacing the C on the second electrode with G in (B). Operation of the G reader is illustrated by a calculation of the conductance of the junction with, and without the G target-base in (C) (the gold slabs shown constitute part of the structure projected into semi-infinite electrodes). The relative lifetimes of the bound and unbound complexes are expected to differ significantly too.

Preferably the base-pair readers are synthesized with a thiol linkage (for attachment to a gold electrode) and an amide linkage (for attachment to CNT). See FIG. 38 for exemplary trans base-pair readers in action. See also example 2.

This process is illustrated for an oligomer containing a guanine base in FIG. 24. By means of one of the nanopore-electrode schemes described above, an oligomer, 1, containing a G base passes by a first electrode 4 to which is attached a C base 2. This base forms a triply hydrogen bonded complex with the target G base as shown in 6. This complex then forms another three hydrogen bonds with the G-C basepair reader 3 that is attached to an adjacent electrode 5. The bonded complex is shown in 7. It is stabilized by a total of six hydrogen bonds and forms a short and direct tunneling path between the electrodes 4 and 5. The short path means that the tunnel conductance will be many orders of magnitude larger than for paths that cross the whole DNA, particularly because the backbone sugar appears to be a significant obstacle to tunneling, in contrast to the aromatic bases. This, in turn, means that the recognition reagents may be tethered to the electrodes with long (e.g., 3 or 4 methylene units) flexible linkers, greatly facilitating assembly of the reader.

A second advantage of the present invention is that that base-pair reader will work for each combination of the pairs, so long as it is free to rotate about the bond that holds it to an electrode. This rotated arrangement is shown in compound 8 of FIG. 24. In this geometry, a G base, tethered to the electrode 4 forms a Watson-Crick pair with a C target in the oligomer being sequenced. The C-G reader then forms another three hydrogen bonds with the paired GC to again complete a tunnel path, this time reading a C on the target DNA.

Figure 25:
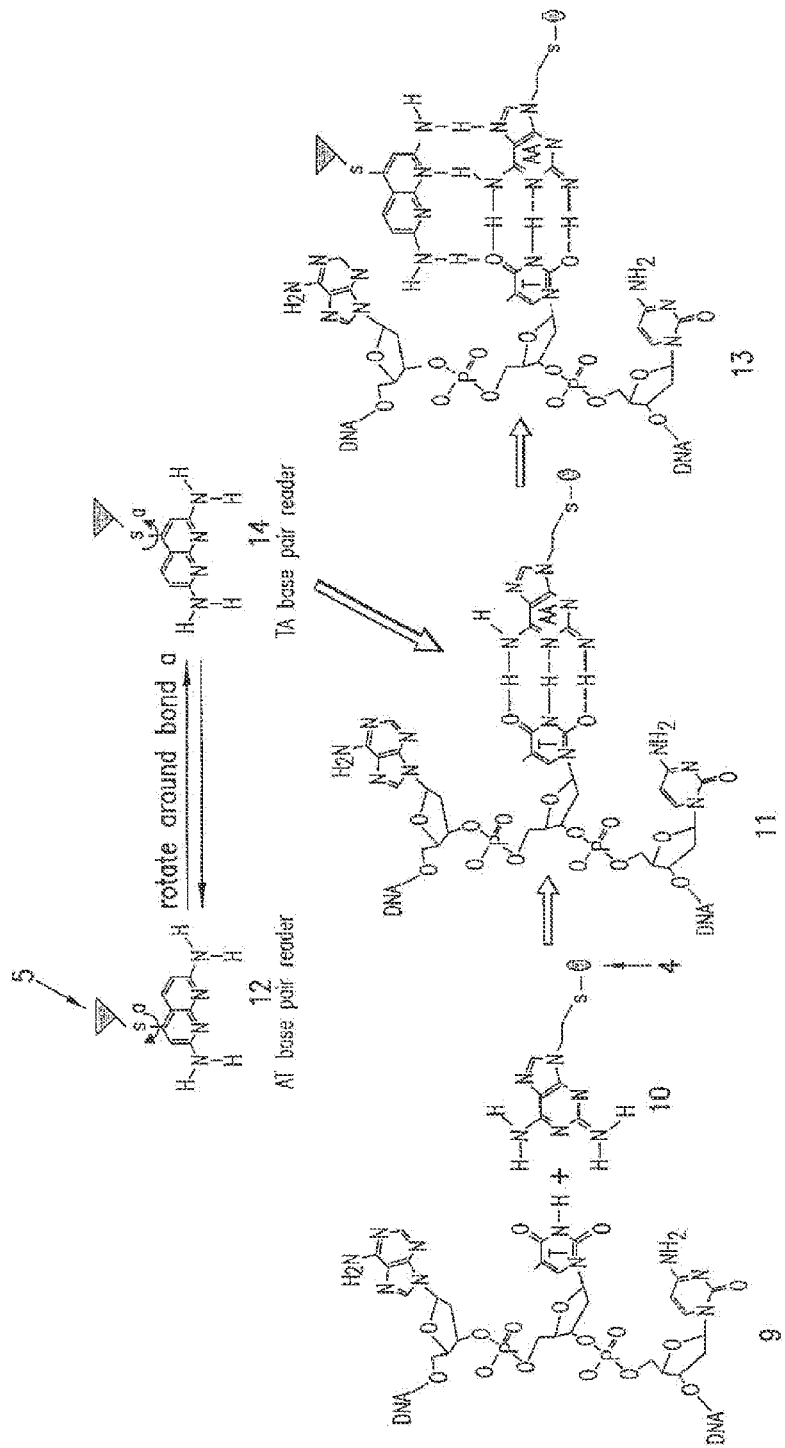
FIG. 25 shows one embodiment of the invention where a A-T or T-A base pair reader forms a triple hydrogen bond with the T base present on the DNA strand and the A base reader attached to one electrode.

A similar arrangement can be used to read A's or T's as shown in FIG. 25. Here a target T is shown on the oligomer, 9, and a 2-aminoadenine 10, tethered to an electrode, 4, is used to form a triply hydrogen bonded complex with the T, 11. This complex in turn forms another three hydrogen bonds with the A-T reader 12 attached to a second electrode 5. The complex, again stabilized by six hydrogen bonds is shown in 13. Once again a short and direct tunneling path is completed, allowing for the incorporation of flexible linkers if needed.

The reading of an A target proceeds the same way, except that the Watson-Crick base pair formed with a T tethered to the electrode 4 will only form 2 hydrogen bonds with the target A. The same A-T reader, if free to rotate about its attachment point to the second electrode (5) can again form 3 hydrogen bonds with the complex, which is now stabilized by 5 hydrogen bonds. This arrangement nonetheless offers a short and quite strong tunneling path between the electrodes 4 and 5.

As used herein, a DNA base pair reader recognizes DNA base pairs through hydrogen bonding, which can be used for DNA sequencing. As illustrated in FIG. 24, a specific base pair reader recognizes a particular DNA base pair that is formed by a base in a single stranded DNA and a base reader. The base readers discussed above and the base pair readers have the following common features: 1) able to form triple hydrogen bonds with bases and base pairs; 2) are structurally complementary to bases and base pairs in terms of size, shape, and hydrogen bonding pattern; 3) able to form thermodynamically stable complexes with bases and base pairs to reduce the entropy loss during the reading process based on the preorganization principle; 4) are fairly conductive: aromatic, plane, heterocyclic; 5) are synthetically available; and 6) are chemically stable under physiological conditions.

Figure 26:
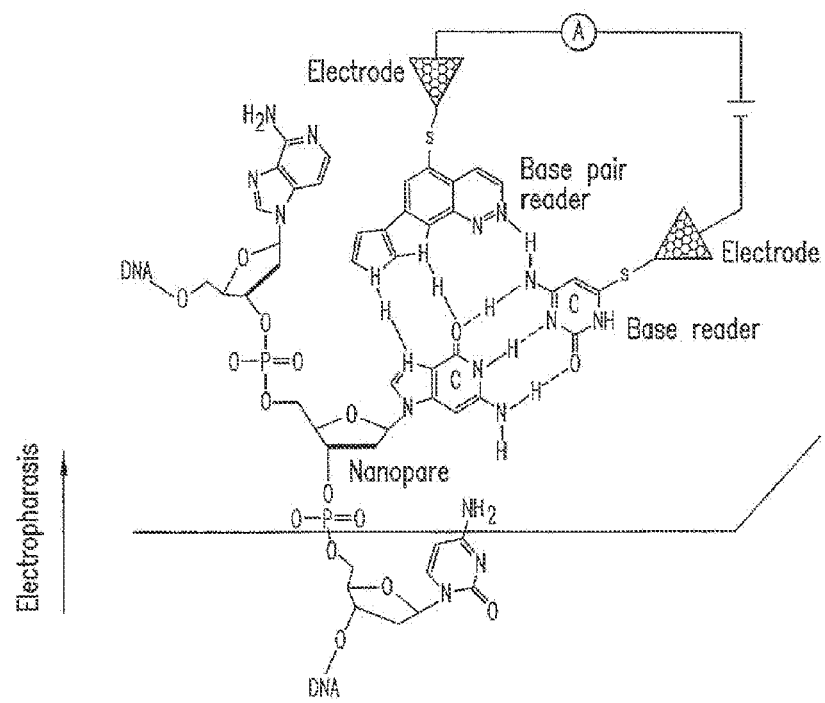
FIG. 26 shows an exemplary device with the DNA translocated through a nanopore and a base reader attached to one electrode and a base pair reader attached to a second electrode.

FIG. 26 illustrates a specific base pair reader recognizing a particular DNA base pair that is formed by a base in a single stranded DNA and a base reader attached to an electrode as the DNA passes through a nanopore.

Exemplary A-T and T-A base pair readers include 1,8 napthyridine and 1,10-Phenanthroline derivates that are capable of forming triple hydrogen bonds with a DNA base pair of T-A or A-T. A preferred A-T or T-A base pair readers comprises the compound of formula I:

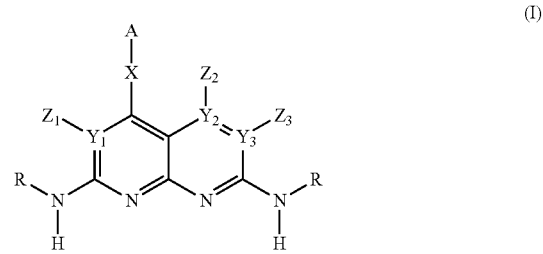

(I)

wherein X is an H, alkyl, $CH_2$, $CH_2CH_2$, alkene, alkyne, or an aromatic ring;

$Y_1$ is C, N or X-A (with the proviso that when $Y_1$ is X-A, $Z_1$ is not present);

$Y_2$ is C, N or X-A (with the proviso that when $Y_2$ is X-A, $Z_2$ is not present);

$Y_3$ is C, N or X-A (with the proviso that when $Y_3$ is X-A, $Z_3$ is not present);

$Z_1$ is O or N;

$Z_2$ is O or N;

$Z_3$ is O or N;

R is alkyl or carbonyl; and

A is S, Se, N, or carbonyl, with the proviso that when X is H or an alkyl, A is not present.

Another preferred A-T or T-A base pair reader is a 1,8-Napthyridine derivative comprising formula II:

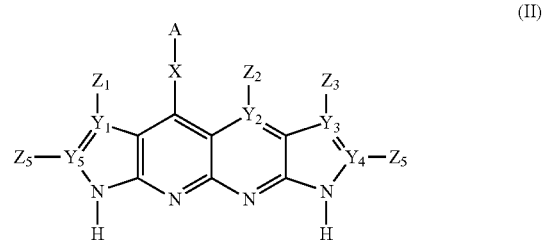

(II)

wherein is an H, alkyl, $CH_2$, $CH_2CH_2$, alkene, alkyne, or an aromatic ring;

$Y_1$ is C, N or X-A (with the proviso that when $Y_1$ is X-A, $Z_1$ is not present);

$Y_2$ is C, N or X-A (with the proviso that when $Y_2$ is X-A, $Z_2$ is not present);
$Y_3$ is C, N or X-A (with the proviso that when $Y_3$ is X-A, $Z_3$ is not present);
$Y_4$ is C, N or X-A (with the proviso that when $Y_4$ is X-A, $Z_4$ is not present);
$Y_5$ is C, N or X-A (with the proviso that when $Y_5$ is X-A, $Z_5$ is not present);
$Z_1$ is O or N;
$Z_2$ is O or N;
$Z_3$ is O or N;
$Z_4$ is O or N;
$Z_5$ is O or N; and
A is S, Se, N, or carbonyl, with the proviso that when X is H or an alkyl, A is not present.

Another preferred A-T or T-A base pair reader is a 1,10-Phenanthroline derivative comprising formula III:

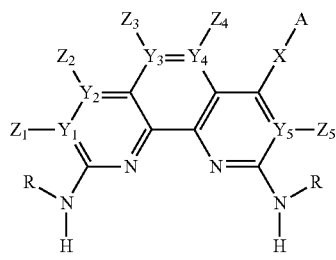

wherein is an H, alkyl, $CH_2$, $CH_2CH_2$, alkene, alkyne, or an aromatic ring;
$Y_1$ is C, N or X-A (with the proviso that when $Y_1$ is X-A, $Z_1$ is not present);
$Y_2$ is C, N or X-A (with the proviso that when $Y_2$ is X-A, $Z_2$ is not present);
$Y_3$ is C, N or X-A (with the proviso that when $Y_3$ is X-A, $Z_3$ is not present);
$Y_4$ is C, N or X-A (with the proviso that when $Y_4$ is X-A, $Z_4$ is not present);
$Y_5$ is C, N or X-A (with the proviso that when $Y_5$ is X-A, $Z_5$ is not present);
$Z_1$ is O or N;
$Z_2$ is O or N;
$Z_3$ is O or N;
$Z_4$ is O or N;
$Z_5$ is O or N; and
A is S, Se, N, or carbonyl, with the proviso that when X is H or an alkyl, A is not present.

Another preferred AT or T-A base pair reader is a 1,10-Phenanthroline derivative compound comprising formula IV:

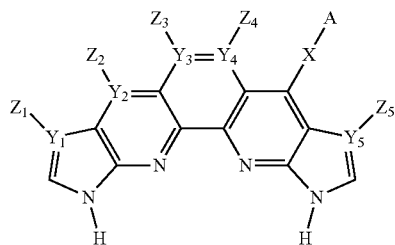

wherein is an H, alkyl, $CH_2$, $CH_2CH_2$, alkene, alkyne, or an aromatic ring;
$Y_1$ is C, N or X-A (with the proviso that when $Y_1$ is X-A, $Z_1$ is not present);
$Y_2$ is C, N or X-A (with the proviso that when $Y_2$ is X-A, $Z_2$ is not present);
$Y_3$ is C, N or X-A (with the proviso that when $Y_3$ is X-A, $Z_3$ is not present);
$Y_4$ is C, N or X-A (with the proviso that when $Y_4$ is X-A, $Z_4$ is not present);
$Y_5$ is C, N or X-A (with the proviso that when $Y_5$ is X-A, $Z_5$ is not present);
$Z_1$ is O or N;
$Z_2$ is O or N;
$Z_3$ is O or N;
$Z_4$ is O or N;
$Z_5$ is O or N; and
A is S, Se, N, or carbonyl, with the proviso that when X is H or an alkyl, A is not present.

Preferred G-C or C-G base pair readers include cinnoline derivatives that are capable of forming triple hydrogen bonds with a G-C or C-G DNA base pair. A preferred G-C or C-G base pair reader is a compound comprising formula V:

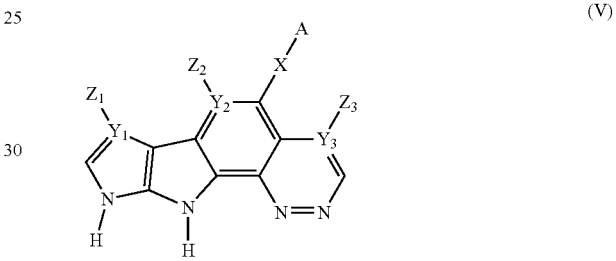

wherein X is an H, alkyl, $CH_2$, $CH_2CH_2$, alkene, alkyne, or an aromatic ring;
$Y_1$ is C, N or X-A (with the proviso that when $Y_1$ is X-A, $Z_1$ is not present);
$Y_2$ is C, N or X-A (with the proviso that when $Y_2$ is X-A, $Z_2$ is not present);
$Y_3$ is C, N or X-A (with the proviso that when $Y_3$ is X-A, $Z_3$ is not present);
$Z_1$ is O or N;
$Z_2$ is O or N;
$Z_3$ is O or N; and
A is S, Se, N, or carbonyl, with the proviso that when X is H or an alkyl, A is not present.

Another preferred G-C or C-G base reader is a cinnoline derivative compound that comprising formula VI:

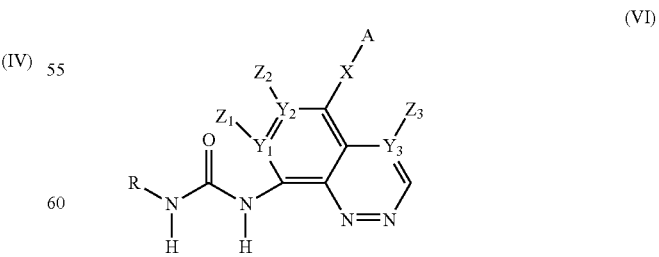

wherein X is an H, alkyl, $CH_2$, $CH_2CH_2$, alkene, alkyne, or an aromatic ring;
$Y_1$ is C, N or X-A (with the proviso that when $Y_1$ is X-A, $Z_1$ is not present);

$Y_2$ is C, N or X-A (with the proviso that when $Y_2$ is X-A, $Z_2$ is not present);

$Y_3$ is C, N or X-A (with the proviso that when $Y_3$ is X-A, $Z_3$ is not present);

$Z_1$ is O or N;

$Z_2$ is O or N;

$Z_3$ is O or N;

R is alkyl or carbonyl; and

A is S, Se, N, or carbonyl, with the proviso that when X is H or an alkyl, A is not present.

Additional readers include the compound of the following formula:

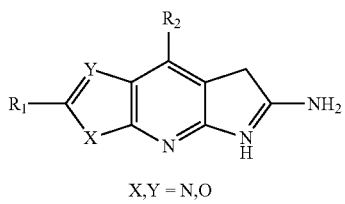

X,Y = N,O wherein $R_1$ can be H, $CH_3$, iso-propyl, tert-butyl, halogen, or any bulky groups such as, but not limited to, carborane, pyrene, adamantane, and fullerene. $R_2$ can be a short alkyl chain, or any conductive molecular fragments, such as, but not limited to, alkene linkages and phynylene-vinylidine linkages. Each of them contains a functional group that can be used for attachment to electrodes, such as amine and thiol, at its end.

Preferably the trans-base pair reader is synthesized with an amide and thiol linker (see example 2) for ease in attachment to the CNT and electrodes, respectively.

Characterization and Control of DNA translocation through a functionalized pore

The operation of the sequencer depends on the speed and controllability of translocation, the role of the sequence itself in pore-friction and the degree to which secondary structures delay transit. The many studies of DNA translocation through a nanopore have generally focused on unfunctionalized nanopores (the exception is Astier et al.). Translocation through a functionalized nanopore is different. This should be evident given that λ-DNA translocates a approximately 6 nm diameter pore in a few ms (at V=50 mV and 1M KCl), equivalent to a speed of 8 mm/s. It is has been measured that the H-bond lifetime is on the order of a few ms, which corresponds to a "speed" of just microns per second, on the assumption that each base is trapped in the reader for a millisecond or so, since even with negative base reads, the phosphate-guanidinium trapping still occurs. The force generated in the STM pull is probably dominated by the softer material in the gap, as disclosed in He et al., but it is surely quite large, as H-bonds require forces on the order of 100 pN to rupture at these pulling speeds (see FIG. 13 of U.S. provisional 61/103,019) and Ashcroft et al.)). In one study of (cyclodextrin) functionalized nanopores, nucleotides became trapped for significant times, illustrating the large effect of pore functionalization.

In accordance with one embodiment of the present invention, translocation of DNA through functionalized nanopores can be accomplished using magnetic beads affixed to a leading end of the DNA as the primary manipulation tool, because this technology is compatible with parallel operation of many reading heads. This is because one set of magnets can pull many beads. The force on a bead of volume v and magnetization m in a field gradient is given by:

$$\frac{\partial B}{\partial z} \text{ is given by } F_z = mv\frac{\partial B}{\partial z}.$$

With a field gradient of 100 T/m (readily obtained with permanent magnets) and 3 μm superparamagnetic beads available from Magsense (West Lafayette, Ind.), forces of up to 150 pN are obtainable. This is comparable to "optical tweezers" and also similar to the larger electrophoretic forces experienced in nanopores. A "magnetic tweezers" apparatus having a high field gradient magnet stack can be used to study translocation in functionalized nanopores.

FIG. 18 illustrates a device 320 that can track DNA transit to within 10 nm by fitting the Airy-fringe pattern around the bead when the objective is out of focus. The time resolution is limited to the 50 Hz frame-grabbing rate of the camera interface, but this is adequate with 1 ms transit times because the height resolution is limited to around 20 bases (and 20 bases can transit in about 20 ms, which is 1/50th of a second). The device 320 includes a light source 331 which projects a light beam past magnets 332 towards a DNA-tethered bead 333. A lens 334 amplifies the bead signal and the resulting image is directed to a camera 335 via a mirror 336. It is understood that other detection arrangements may also be employed.

FIG. 19A illustrates some of the factors controlling translocation. The electrophoretic force, $F_{elec}$, is opposed by H-bond friction 331 in the gap 332. The entry of the DNA 333 into the pore 334 is typically opposed by entropy fluctuations, and, more importantly, secondary structure 335. For a secondary structure undergoing random thermal openings at a rate $K_0$, the opening rate on application of a force f is $$k(f) = k_0 \exp\left[\frac{f \cdot x_{ts}}{k_B T}\right]$$

where $x_{ts}$ is the distance to the transition state from the folded state along the direction in which the force is applied. The smallest values of $K_0$ for hairpins trapped in a nanopore is about 1 s$^{-1}$ which is really very slow. Based on measured values for $x_{ts}$ for a tight molecular nanopore 50 (about 0.1 nm) an electrophoretic force of 100 pN would increase the opening rate to about 10 s$^{-1}$. Thus, secondary structure could be a significant obstacle to fast reads. The ssDNA could be pre-stretched using the magnetic bead 336 but this would reduce the net force across the pore 334, increasing the rate of backwards slippage.

As seen in FIG. 19B, pre-stretching would probably require a bead 335a, 335b trapped at both ends to form a rotaxane with the nanopore.

As depicted in FIG. 19B, in yet another arrangement, one may want to augment the electrophoretic force using a magnetic bead 335c.

In each of these experiments, one can measure the output of the sensing electrodes using a DNA molecule of known sequence. This allows one to correlate features in the gross transport (as measured by bead movement and pore current) with local features (as measured by the molecular recognition signal from the sensing electrodes). One approach is to use the M13 genome as a source of long ssDNA (6.5 kb). Cutting it requires hybridization with a short helper strand in order to form a local dsDNA template for a restriction enzyme. The short strand is easily removed by filtration after denaturation.

Next, splint-ligation may be used at both ends, putting in a biotin at one end and a digoxigenin at the other, with a two step affinity column purification of the long product. Modification of λ-DNA using incorporation of modified dNTPs followed by magnetic extraction of the desired strand at high pH may also be performed. The "flossing" experiment (FIG. 19B) can be carried out by trapping the DNA-antiDIG bead from the cis chamber using electrophoresis and then functionalizing the DNA in the trans chamber with a streptavidin coated magnetic bead. Finally, a novel "unstructured" DNA may be available for use that forms Watson-Crick basepairs with natural bases, but the modified bases will not pair with each other. Presently, the modified nucleotides can be incorporated in runs of up to 600 bases.

It should be evident to one skilled in the art that the foregoing enables one to improve upon the basis design and methodology. More particularly, one may: 1) measure the transit time of known oligomers through nanoelectrode pores; 2) re-measure transit times with functionalized pores. One can thus test to see if the asymmetry of the backbone (5'-3' vs. 3'-5') affects readout fidelity and transit times, using bead functionalization at one end or the other; or 3) measure transit times as a function of pH. Secondary structure is removed at low pH but the same conditions that remove secondary structure (pH>11.6) may also destroy H-bonding.

One may measure transit times through both functionalized and unfunctionalized pores with unstructured DNA to measure the extent to which secondary structure slows entry into the pore. These measurements can determine the relative contributions of secondary structure and H-bond friction in slowing transit. Magnetic bead experiments may be designed to speed up or slow down the translocation as needed. One may test these arrangements using the functionalized, linearized M13 DNA, correlating the local sequence data from the sensing electrodes with the progress of translocation as measured optically.

There are multiple forces acting on the ssDNA as it translocates—the magnetic force on the bead, the electrophoresis force on the charged ssDNA, the hydrogen bonding force of the guanidinium attempting to hold the DNA in place, the hydrogen bonding force of the base-reader on the target base, interactions of ssDNA with itself (secondary structure), the viscous force of the water on the magnetic bead, and interactions of the DNA with water and with the walls of the nanopore. The length of the tether molecules is also important. Varying it, even slightly, may change the number of contacts and/or the probability of simultaneous phosphate and base recognition.

Characterization of Signals from Oligomers and Genomic DNA Using a Set of Single Pores.

The sequence-reconstruction problem has two inputs. One is the optical tracking of transport which could give data at a resolution that could be as high as 20 bases. The second is the signals from the molecular reading heads themselves. Reading head data of adequate quality could permit alignment of data from all four reading heads with no other input. Data for each individual base that is 99.99% accurate may be obtained by a combination of improved affinity elements and multiple reads of the same sequences. If the data from each head are of adequate quality, one may record repeated runs for each type of base with high fidelity.

When sequencing four copies of ssDNA using four nanopores, each nanopore having a different base reader as the second affinity element, four component sequence reads are created. Each sequence read identifies, as a function of base location, the points at which a nucleotide of a particular type has been detected. Since there may be differences in the rates at which the four copies of the ssDNA electrophorese through their respective nanopores, there may be an issue of aligning the four component sequence reads to arrive at a final sequence read representing the sequenced ssDNA. Blocks of a repeated base (e.g., 4× or 5×) are rare enough that they can serve as good indices of position in the genome, and yet frequent enough so that a significant number of them occur in each read. Thus, upon obtaining a sequence of component reads of ssDNA from each of four readers, one may align the four sequences of component reads based on one or more preselected blocks of a repeated nucleotide (which hopefully will be present in at least one of the sequences of component reads.) For example, positive reads of an A5 tract (A-A-A-A-A) would be aligned with unique (or rare) gaps of null readings of 5 bases in extent from the C, G and T readers. This is called the "framing problem" in parallel transmission of digital data over noisy channels. The problem is greatly simplified if the direction of the data stream is fixed. Thus one can develop protocols for preprocessing input DNA and ligating beads (or even just form crosslinked dsDNA blockers) to control the entry direction. Once any such needed alignment has been done, one may then create a final sequence of reads representing the sequenced ssDNA from the four component sequences of reads.

The optical tracking data can record each translocation to within 20 bases at best, with maybe substantially poorer resolution when entropy and secondary structure fluctuations are taken into account. But it also serves as a check on the local alignment algorithms, eliminating gross mistakes (i.e., juxtaposition errors greater than the optical tracking resolution).

Quantitative data obtained from using the device of the present invention may be used to develop data analysis tools for rapid sequence recovery. Some of the issues that can be addressed by such quantitative data include: (1) the transit times per base in the read (base+phosphate H-bonds) vs. the no-read (phosphate H-bonds only); (2) the frequency with which a nucleotide is missed altogether; (3) the fluctuations in average read speeds; (4) the role of secondary structure; and (5) whether it would help if "stalling," owing to secondary structure, occurred predictably.

As discussed herein, one may construct a fixed-gap nanopore sequence device capable of reading single bases with high fidelity. Such a device may incorporate one or more of the following features: electrochemically grown self-aligning electrodes, active gap adjustment, and gold as the electrode material. In use, such a device may be able to deal with the potential problems of secondary and tertiary structures in long DNA transits. Furthermore, the assembly of such devices may be facilitated and even automated for consistency from unit to unit, thereby mitigating uncertainties in the performance of one-off designs. The assembly and functionalization methods allow for reforming and healing of devices whose readers have been damaged or otherwise spent.

Another Device of the Present Invention

The present invention further provides a DNA sequencing device configured to identify at least one portion of a target DNA molecule. The device comprises a partition having a first side and a second side, and at least one constriction passing between the first and second sides, the constriction being shaped and sized to permit translocation of only a single copy of the DNA target molecule therethrough. The device further comprises a first and second sensing electrodes associated with the first side of the partition and being separated from one another by a first gap. The device comprises a first affinity element comprising a base reader (as described above) connected to the first electrode; and a second affinity element comprising a base pair reader (as described above) connected to the second electrode. When a particular portion of the DNA target molecule translocates through the constriction, an electrical current passes through the first electrode, the base reader, said particular portion of the DNA molecule, the base pair reader, and the second electrode.

Preferably, the electrical current comprises a tunneling current that passes through: a first set of hydrogen bonds established between the base reader and a nucleotide base of the DNA target molecule, and a second set of hydrogen bonds established between the base pair reader and the nucleotide base of the DNA target molecule and the base reader.

The present invention further provides a method of sequencing DNA as the DNA molecule translocates through a constriction. The method comprises providing an apparatus comprising a DNA sequencing device as described above. The device is located in the apparatus such that a first chamber is located on the first side of the device and a second chamber is located on the second side of the device. A DNA molecule (preferably single stranded) is introduced into the second chamber. The DNA molecule is electrophoresed so that it translocates through the constriction. The electrical current passing through the first electrode, the base reader, a nucleotide base of the DNA molecule, the base pair reader and the second affinity element, and the second electrode is detected.

The present invention also provides a method of sequencing ssDNA comprising providing an apparatus having the DNA sequencing device as described above arranged such that a first chamber is located on the first side of the DNA sequencing device and a second chamber is located on the second side of the DNA sequencing device. At least four copies of the ssDNA to be sequenced are introduced into the second chamber. The four ssDNA copies are simultaneously electrophoresed the so that each copy translocates through one of the four constrictions of the DNA sequencing device. During electrophoreses, at each constriction, it is determined whether a nucleotide has been recognized based on an electrical current passing through the first electrode, the base reader, the nucleotide, the base pair reader and the second electrode, to thereby create four component read sequences, one component read sequence for each constriction.

Figure 34A:
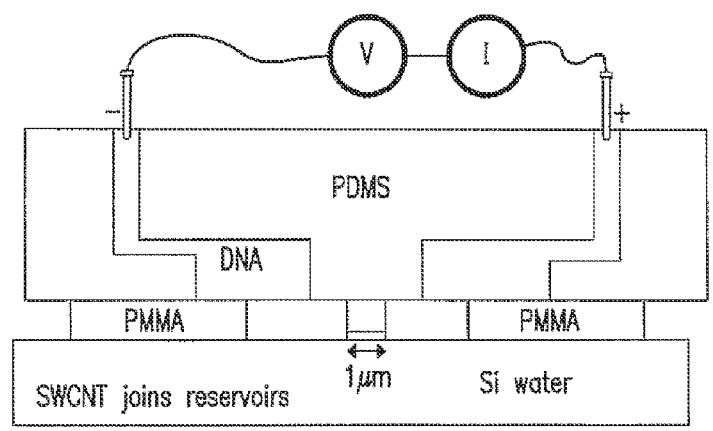
FIG. 34; Construction of a CNT nanopore device (A). (B) is SEM image (PMMA pegs prevent collapse of PDMS) Enhanced contrast region shows SWCNT in orange (prior to plasma etch). (C) Complete device with PDMS cover.

The present inventors have shown that electrode tethered guanidium ions can be used to complete an electrical circuit for reading bases in a single stranded DNA (see example 1, pages 47-49 of U.S. provisional 61/103,019). The inventors have also found that a readable signal is obtainable if the circuit is completed using a complementary DNA as a second connector (see example 2, pages 49-51 and FIGS. 34 and 37 of U.S. provisional 61/103,019).

In methods of the present invention, it may be preferable to perform the reaction in an aprotic solvent (an organic solvent without free proteins). For example, one universal reader, thiobenzoic acid, can act as a hydrogen bond donor and acceptor in aprotic solvents, since the carboxylate residue remains protonated. An exemplary solvent is trichlorobenzene. The OH group acts rather like a hydrogen bond donor and the doubly bonded oxygen is similar to a hydrogen bond acceptor so that these molecules are capable of quite strong pairing with each other. (Jeffrey, G. A., An Introduction to Hydrogen Bonding. 1997, Oxford: Oxford University Press).

Device Utilizing a SWCNT Comprising Small Gaps Functionalized with Recognition Elements.

SWCNTs a nanopores and as integrated electrodes off the benefit of providing a route to control translocation of DNA, especially if the DNA in the tube is essentially immobile at low electric fields. Using SWCNTS as integrated electrodes has the advantage in that the CNT serves an electrode already aligned with the nanopore. They also provide specific and stable sites for chemical linkages (i.e. for linking recognition elements) and they provide multiple sites surrounding the nanopore.

Serial Recognition Sequencer

The present invention provides a device comprising a SWCNT for characterizing a biopolymer. The device comprises a carbon nanotube having an interior channel through which the biopolymer is driven by electrophoresis. The carbon nanotube comprises a plurality of gaps cut into the carbon nanotube. The plurality of gaps are functionalized to provide a characteristic signal at each of the gaps. In a preferred embodiment, the biopolymer is a nucleic acid such as DNA or RNA, and the carbon nanotube comprises four gaps cut into the carbon nanotube. In this embodiment each gap is functionalized with a different nucleoside reader.

Figure 27:
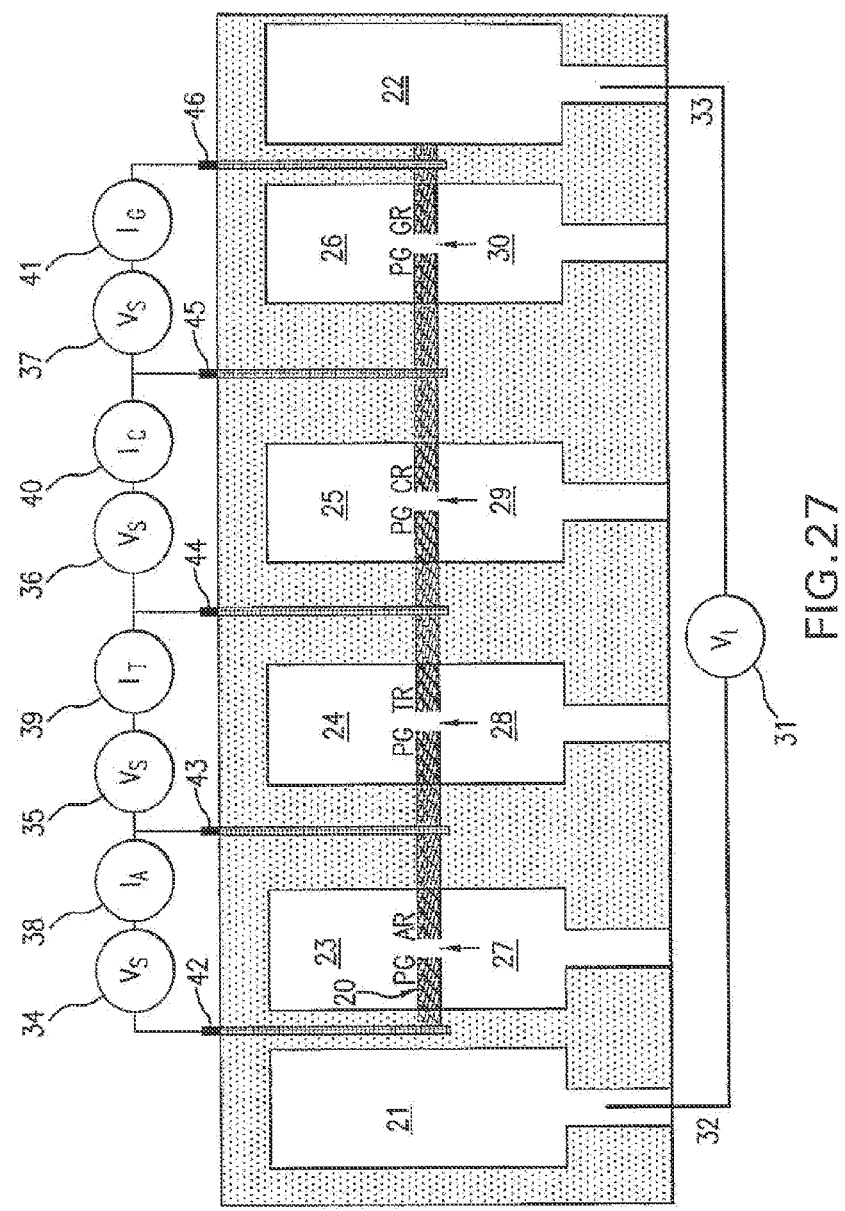
FIG. 27: A serial recognition sequencer

With reference to FIG. 27, the present method further provides a device for determining the sequence of a nucleic acid comprising: a) a solid surface to support a carbon nanotube (20) having an interior channel through which the nucleic acid can travel; and b) an insulating film layer disposed on top of the carbon nanotube.

Preferably the solid surface is an oxidized silicon wafer upon which the carbon nanotube can be grown. The insulating film layer is a material that provides insulation against an electrical current, such as polymethyl methacrylate (PMMA).

The insulating film layer comprises an origination (21), a first (23), a second (24), a third (25), a fourth (26) and a termination (22) well capable of containing an electrolyte. As shown in FIG. 27, the origination well (21) is proximal to the first, second, third, fourth and termination wells, and the termination well (22) is distal to the first, second, third, fourth and origination wells.

The carbon nanotube comprises a first (27), second (28), third (29) and fourth (30) gap cut into the carbon nanotube. The first gap (27) contacts the first well (23), the second gap (28) contacts the second well (24), the third gap (29) contacts the third well (25) and the fourth gap (30) contacts the fourth well (26).

Each of the first, second, third and fourth gaps of the carbon nanotube has a first gap end and a second gap end. Each of the first gap ends is functionalized with a first recognition element (e.g. in FIG. 27 ("PG")) and each of the second gap ends is functionalized with a second recognition element (e.g. in FIG. 27 ("AR," "TR," "CR" or "GR")).

The carbon nanotube has an origination end (OR) in contact with the origination well (21) and a termination end (TE) in contact with the termination well (22). An origination electrode (32) contacts the origination well (21) and a termination electrode (33) contacts the termination well (22). The origination and termination electrodes do not contact the carbon nanotube.

As used herein the term "contact" means directly contacting or also means being contacted to. Thus the electrode could directly contact the well or the electrode may be contacted to the well via a salt bridge, for example. Similarly the electrodes contacting the carbon nanotube (discussed below) may directly contact the carbon nanotube or may be contacted to the carbon nanotube indirectly.

The device further comprises a first electrode (42) contacting the carbon nanotube between the origination well (21) and the first well (23); a second electrode (43) contacting the carbon nanotube between the first (23) and the second well (24); a third electrode (44) contacting the carbon nanotube between the second (24) and third (25) well; a fourth electrode (45) contacting the carbon nanotube between the third

(25) and fourth (26) well; and a fifth electrode (46) contacting the carbon nanotube located between the fourth (26) and termination well (22).

The gaps cut into the carbon nanotube are small and are preferably only a few nm in width.

A voltage bias $V_t$ (31) may be applied between the origination well (21) and the termination well (22) by the origination electrode (32) and the termination electrode (33) to produce a positive bias in the termination well with respect to the origination well to allow translocation of DNA along the length of the carbon nanotube through the carbon nanotube channel from the origination well through the first, second, third, and fourth wells to the termination well.

So long as the geometry in each well is similar, a voltage drop of $V_t/4$ appears at each of the four gaps in the absence of any other connection. If the termination well (22) is biased positive with respect to the origination well (21) (by a voltage between 0.5 and 2V) DNA will translocate along the length of the nanotube (20), from well (21) to well (22) (through wells 23, 24, 25 and 26).

Each part of the carbon nanotube is, in turn, connected by an electrode. As mentioned above, referring to FIG. 27, the device comprises a first electrode (42) contacting the carbon nanotube between the origination well (21) and the first well (23); a second electrode (43) contacting the carbon nanotube between the first (23) and the second well (24); a third electrode (44) contacting the carbon nanotube between the second (24) and third (25) well; a fourth electrode (45) contacting the carbon nanotube between the third (25) and fourth (26) well; and a fifth electrode (46) contacting the carbon nanotube located between the fourth (26) and termination well (22). Because of the low resistance of these connections compared to the electrical path through the electrolyte, the four voltage sources, (34, 35, 36 and 37) will set the bias across the gaps. Since the required bias across a gap required for translocation (0.2 to 1V) is quite compatible with the bias required for tunnel current readout (0.2 to 0.6V) the gaps can be biased close to the required voltage drops for translocation while the overall bias (31) adds an additional drop at each end to drive DNA translocation from the origination well (21) and out of well (26) into the termination well (22).

Each of the gaps has a first and second end, wherein each of the first ends of the gaps is functionalized with a first recognition element coupled to the carbon nanotube and is optionally coupled via a flexible linker, such as an amine terminated flexible hydrocarbon linker (e.g. an amine terminated (—$CH_2$—)$_2$ flexible linkers). In one embodiment the first recognition element comprises a phosphate grabber (PG) (gaunidinium) that has the ability to recognize and form a hydrogen bond with the backbone phosphate of the nucleic acid. See PCT/US08/59602 (incorporated herein by reference). The second ends of each of the gaps are functionalized with a second recognition element coupled to carbon nanotube. Preferably when the polymer to be sequenced is DNA, the second recognition elements are an adenine reader (AR), a thymine reader (TR), a cytosine reader (CR) and a guanine reader (GR). See PCT/US08/59602 (incorporated herein by reference) for exemplary base readers. In addition, in certain embodiments, the base readers are connected to the carbon nanotube via an amine terminated flexible hydrocarbon linker (e.g. an amine terminated (—$CH_2$—)$_2$ flexible linkers).

In another embodiment, the first recognition element comprises a base that will recognize its Watson-Crick complement on the DNA and the second recognition element comprise a base-pair reader that recognizes either an A-T or a G-C base pair.

Referring again to FIG. 27, a current output signal (38, 39, 40 and 41) is generated each time a base is recognized by its reader. The present invention has the advantage that all four reads, $I_A$, $I_T$, $I_C$ and $I_G$ come from the same molecule. Thus, a mixture of molecules, such as sheared fragments of a genome, can be presented to the device without confusion caused by the need to identify the signal for each base with a particular fragment.

Figure 28:
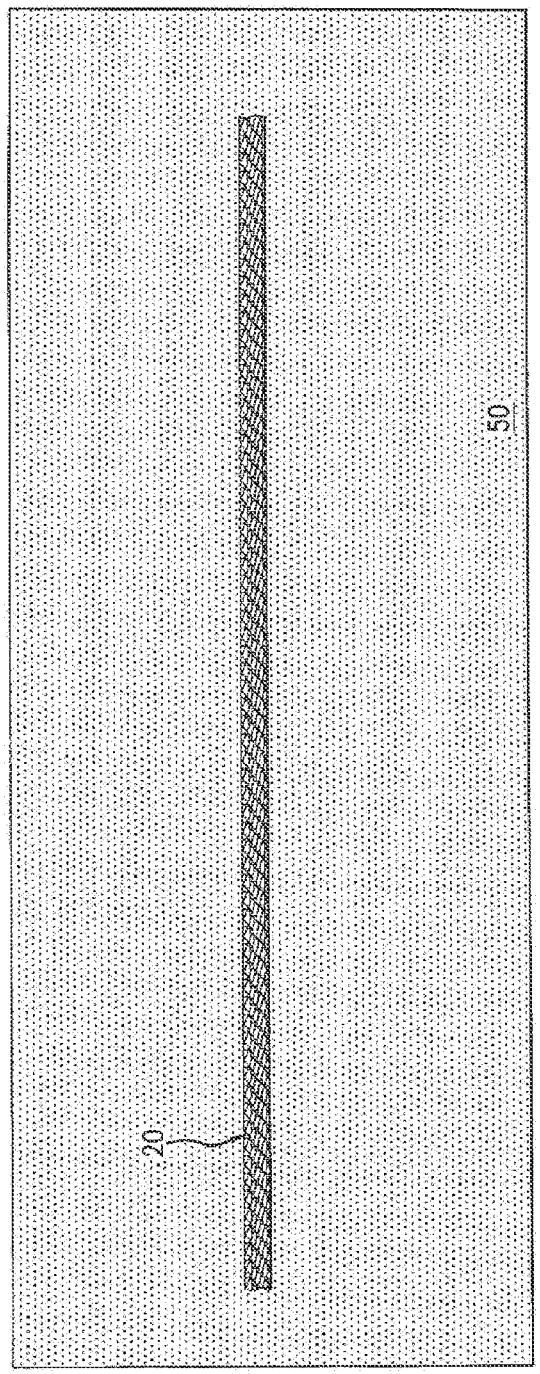
FIG. 28: Oxidized silicon wafer bearing a carbon nanotube.
Figure 29:
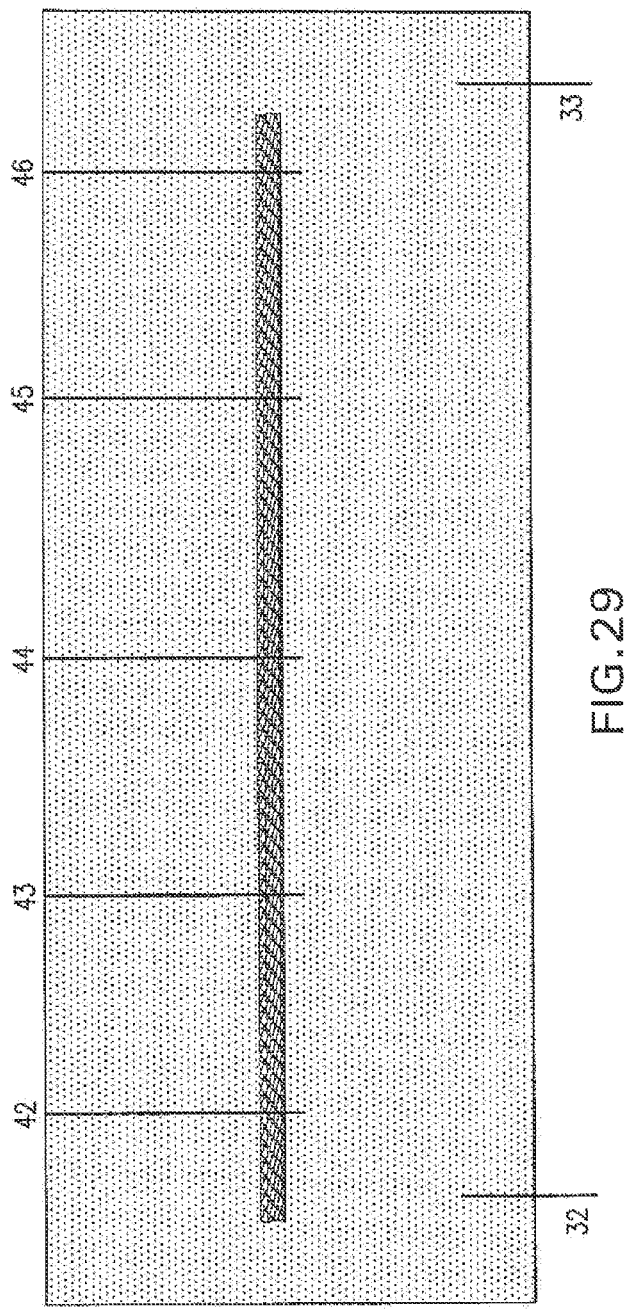
FIG. 29: Carbon nanotube patterned with electrodes

The assembly of one of the devices of the present invention is shown in FIGS. 7 to 12. FIG. 28 shows a single carbon nanotube (20) grown on a silicon wafer (50) by means well known to those skilled in the art. Using conventional lithography or metal deposition through a mask, electrodes are then deposited as shown in FIG. 29. Electrodes (42, 43, 44, 45 and 46) contact the carbon nanotube, and should ideally be made from a metal such as palladium that makes good electrical contacts to nanotubes.

Figure 30:
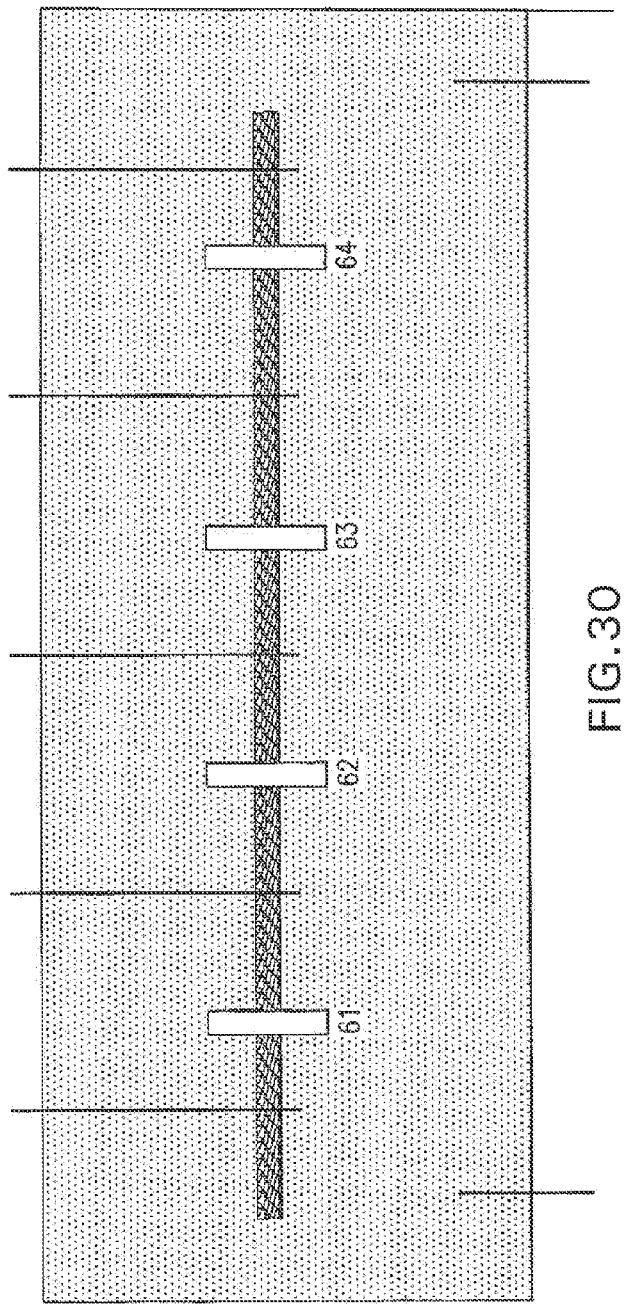
FIG. 30: Device after masking, formation of wells and oxygen plasma etch.
Figure 31:
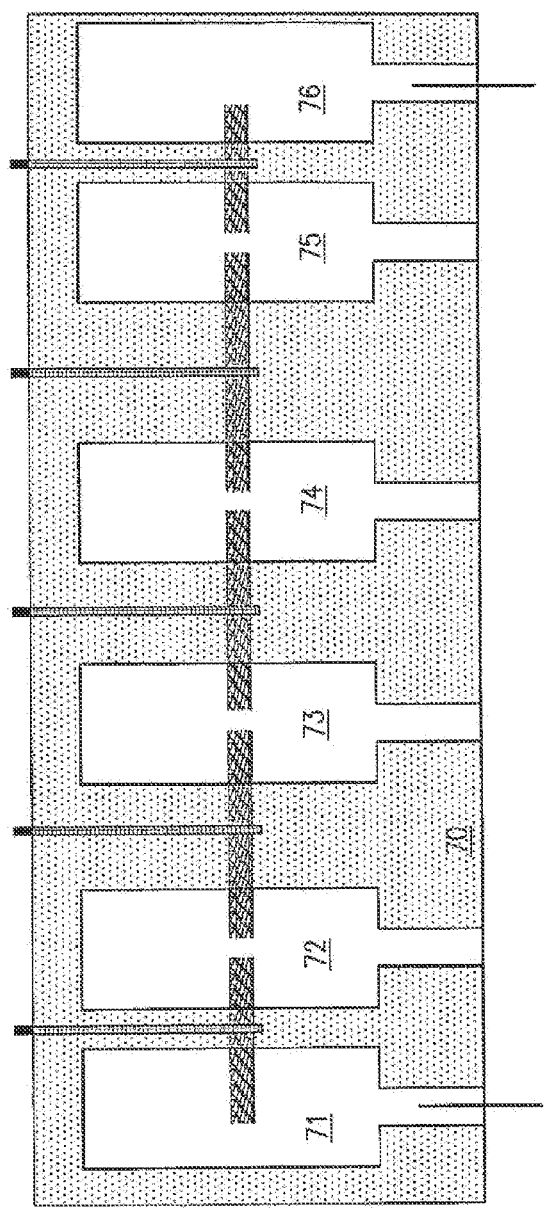
FIG. 31: Wells cut into a second PMMA film.
Figure 32:
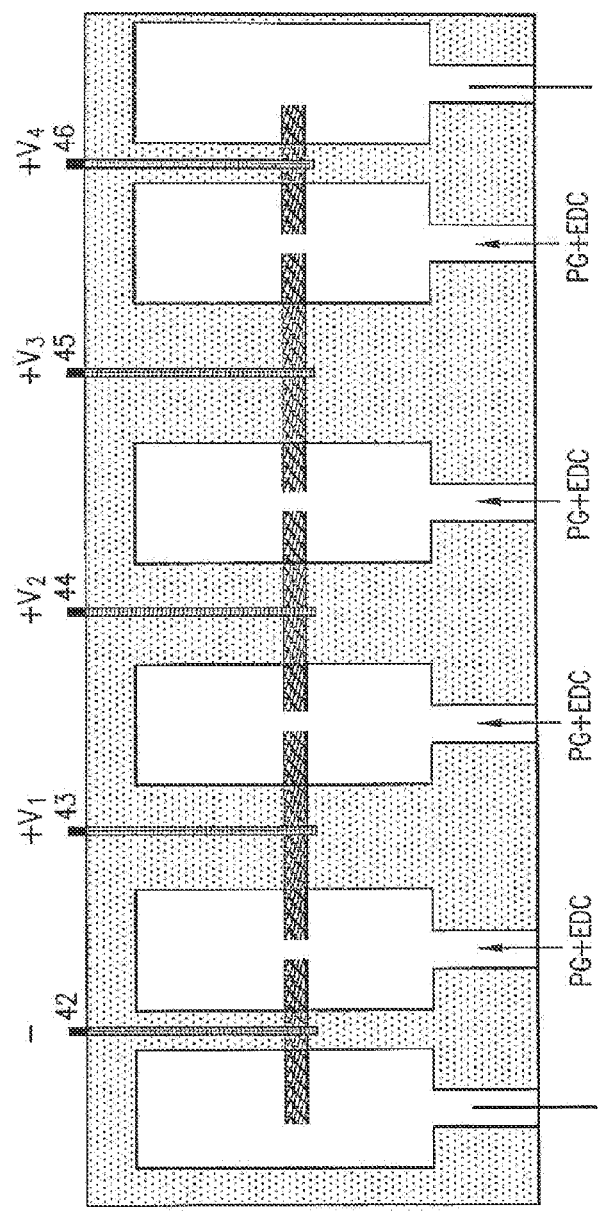
FIG. 32: Selective functionalization of one side of the pairs of reading electrodes with the phosphate grabber ("PG").

Electrodes (32 and 33) are used to contact the electrolytes in the fluid wells, and can be made from any noble metal. Notably, electrodes (32 and 33) do not contact the carbon nanotube. Fabrication of the small gaps along the nanotube is illustrated in FIG. 30. A thin layer of PMMA resist is spun over the nanotube and the regions to be cut, (61, 62, 63 and 64) defined by e-beam lithography. The PMMA is removed in the exposed regions and an oxygen plasma used to make the four cuts shown. As an alternative, the cuts can be made directly with an electron beam in the presence of water vapor. The next step is shown in FIG. 31. The original layer of resist is removed and a new layer deposited, and six wells, (71, 72, 73, 74, 75 and 76) opened up by conventional lithography. The ends of the carbon nanotubes at the four cuts (27 through 30 in FIG. 27) are carboxylated by the exposure to the oxygen plasma (or water vapor), and so can be chemically modified using amine terminated reagents with an EDC catalyst to form amide bonds. FIG. 32 shows the process for modifying the left electrode in each cut with the "phosphate grabber." This is an amine terminated, ethylene linked guanidinium, which is positively charged in pH 7 buffer. Thus, when the amine terminated reagent is flowed into each of the four wells containing the cut tube, with the junctions biased so that the left electrode is biased negative with respect to the right, the positively charged reagent couples only to the left electrode. This biasing is achieved with a bias $V_1$ applied across electrodes (42 and 43), a bias $V_2$ ($>V_1$) applied at electrode (44), a bias $V_3$ ($>V_2$) applied at electrode (45) and a bias $V_4$ ($>V_3$) applied at electrode (46). The four fluid reservoirs that feed in the reagents to the four wells must be electrically isolated from each other to maintain this biasing arrangement. As an alternative, each of the four wells may be separately functionalized by biasing each electrode pair in turn, and flowing reagents into only the biased well. Such a process would be a little more cumbersome, but would eliminate the risk of the positively charged guanidinium being swept into the chamber with the most negatively charged electrode (though this is unlikely given the relatively slow translocation rates through small nanotube). Once a sufficient time for the reaction has passed (1 to 5 minutes), the reagents may be flushed out of the wells and the bias removed. This process leaves only the left electrode at each cut functionalized. The next step is to expose each well in turn to the appropriate reagents, as illustrated in FIG. 33. Here the first well is exposed to the adenine reader (AR)+EDC, the second well to the thymine reader (TR)+EDC, the third well to the cytosine reader (CR)+EDC and the final well to the guanine reader (GR)+EDC. After the reaction, the wells may be flushed and the device is ready for operation.

Repeated reads may be needed to establish the sequence to the desired level of accuracy. In the case of a mixture of input molecules such as might arise from sheared genomic DNA, this would require alignment of the different reads based on sequence overlap. This would be straightforward to do for the longer runs (i.e., runs of many kilobases) even in the presence of noise. The present invention has the advantage that, for each fragment that passes through the device, the mismatch signals can be used to verify a base call. Thus a positive signal at one reader, accompanied by three mismatch signals at the other three would allow for assignment of a base read with much higher confidence that could be obtained from a single reader. Such "super assignments" would then aid in the assembly of the final sequence, even for input samples that are a random selection of fragments of genomic DNA.

Control of DNA Translocation

In a preferred embodiment the SWCNT are 2 nm in diameter. The present inventors have found that in tubes this size, the DNA gets "stuck," requiring some kind of cooperative process for passage. It appears that the DNA enters the tube and "piles up" in the tube until some event or passage of time, the DNA is released from the end of the tube. Thus, the inventors contemplate "freezing" the DNA in place in the tube, by removing the electrophoretic driving field (temporarily suspending) once the DNA has entered the tube. Translocation is then restored by reapplying an appropriate field. Reversing the field might even allow the same molecule to be read many times by "flossing" it back and forth in the SWCNT. See FIG. 43 that shows one embodiment of the invention showing feedback circuitry comprising a current sensing device and a translocation control signal. See also example 5.

The present invention also provides a method of sequencing DNA using devices of the present invention by providing a ssDNA that will be translocated through the nanopore or CNT. As the DNA travels through the pore or the CNT, it will reach the recognition elements attached to the CNT or to other areas of the device as described above. In a preferred embodiment, one recognition element is a base or base reader that will recognize and bind (interact) with its Watson-Crick complement. The other recognition element is a base pair reader that will recognize and interact (through hydrogen bonding) with either an A-T or a G-C base pair. When the DNA coming through the pore or CNT has the base that allows for both recognition elements to bond to the DNA, a closed circuit between the electrodes will occur and a signal is generated. For example, if one of the recognition elements is a T base and the other is an A-T base pair reader, when the DNA strand coming through the pore or CNT has an "A" there will be a bond with the A of the DNA and the T on one of the electrodes and another bond between the resulting A-T base pair and the A-T base reader on the other electrodes. As discussed above, 4 different readers could be run serially, each having an A, G, C or T base as one recognition element and a corresponding A-T or G-C base pair reader or in other embodiments, the DNA runs through a serial reader having 4 gaps, each gap functionalized with a different base.

Single Molecule Characterization

The present inventors have developed a measurement technique for single molecule characterization called the "telegraph noise" technique. See example 4. The present inventors have designed a readout system that uses a shorter tunneling path rather than measuring conductance of a junction spanning an entire DNA molecule (i.e. use of base readers and base-pair readers as two recognition elements tethered to electrodes) and have used this to determine the conductance of individual molecular pairs. The inventors have exploited the stochastic switching of hydrogen-bonded DNA base-nucleoside pairs trapped in a tunnel junction to determine the conductance of individual molecular pairs. This conductance is found to be sensitive to the geometry of the junction, but a subset of the data appears to come from unstrained molecular pairs. The conductances determined from these pairs are within a factor of two of the predictions of density functional calculations. The experimental data reproduces the counterintuitive theoretical prediction that guanine-deoxycytidine pairs (3H-bonds) have a smaller conductance than adenine-thymine pairs (2H-bonds). Analysis of the lifetimes of the complexes indicates a change in the type of bond-breaking as the tunnel gap is made smaller.

Previously, the present inventors and others have shown that electron tunneling can be used as a sensitive local probe to identify individual bases in DNA, a possible basis for direct electronic sequencing. The inventors have found that current-distance curves collected from junctions in which bases attached to a probe are hydrogen bonded to nucleosides or even to intact DNA on an electrode surface faithfully report the base composition of the target. A careful analysis of these signals shows that they do not arise from single-molecule interactions. Rather, the overall conductance of the tunnel gap is probably set by through-space tunneling across a large-area junction containing several (two to ten) molecular pairs. Conducting-AFM measurements provide a rough estimate of the conductance of base-nucleoside pairs as lying somewhere near 100 to 300 pS. Can the conductances of single base-nuleoside pairs be measured directly and accurately? Break-junction techniques for measurement of single molecule conductance are difficult to apply to a system as complex as a base-nucleoside hydrogen bonded pair and they do not report the conductance as measured in the type of fixed junction that would be required for DNA sequencing. Stochastic switching of bonds between molecules and the electrodes of a tunnel junction offers another approach to measuring single molecule conductance. Ramachandran et al. demonstrated that, for tunnel junctions using gold electrodes with thiol-attachment chemistry, fluctuations in the molecule-metal contact result in the stochastic-switching of STM images of molecules embedded in a monolayer. Fluctuations in the C—Si bond were monitored in an STM while the transient binding and unbinding of a carboxylate-EDC complex was monitored via conductance fluctuations in a carbon nanotube. Haiss et al. showed that the time course of bond-fluctuations in a gold-thiol-molecule-thiol-gold tunnel junction could be followed by the simple expedient of placing a gold STM probe above a gold surface functionalized with bis-thiolated alkane molecules. As the molecules spanning the gap bound and unbound to make and break the junction, the tunnel current showed a characteristic fluctuation between two-levels. The two-level nature of the signal is a strong indication that a single molecule is trapped in the gap, as switching of multiple molecules would generate more complex signals. The single-molecule conductance deduced from the amplitude of these tunnel current fluctuations yielded values for the conductance of alkane thiols that were in good agreement with the break junction method. The present inventors have made telegraph-noise measurements made by forming a fixed gap between a probe functionalized with a DNA base and a surface functionalized with nucleosides. See Example 4.

Accordingly, the present invention provides a method of detecting a tunnel current signal that switches between two levels, which is characteristic of an interaction with a single base, and wherein said signal is used to identify the target base in the tunnel gap. The present invention also provides a method of identifying a target base in a tunnel gap by detecting a tunnel-current signal that switches between two levels, wherein the signal switch is characteristic of an interaction with a single base.

GLOSSARY

Base-Reader (BR): A class of molecule, natural or manmade that contains a predetermined pattern and spacing of Hydrogen bond donors and acceptors fixed in space on a molecular scaffold to allow the molecule to bond and recognize molecules with complementary patterns and spacing of Hydrogen bond donors and acceptors.

Universal-Base-Reader (UBR): A class of molecule, natural or manmade that contains sufficient predetermined pattern and spacing of Hydrogen bond donors and acceptors fixed in space on a molecular scaffold to allow the molecule through conformational changes to bond and recognize all molecules of interest with complementary patterns and spacing of Hydrogen bond donors and acceptors.

Adenine-Base-Reader (ABR): A class of molecule, natural or manmade that contains a predetermined pattern and spacing of hydrogen bond donors and acceptors fixed in space on a molecular scaffold to allow the Base-Reader to bond and recognize adenine (abbreviated A). A few examples of an ABR class of molecule are thymine (T), uracil (U) and Riboflavin. These molecules have complementary patterns and spacing of Hydrogen bond donors and acceptors to recognize adenine (A).

Cytosine-Base-Reader (CBR): A class of molecule, natural or manmade that contains a predetermined pattern and spacing of Hydrogen bond donors and acceptors fixed in space on a molecular scaffold to allow the Base-Reader to bond and recognize cytosine (abbreviated C). A few examples of a CBR class of molecule are guanine (abbreviated G) and isoguanine. These molecules have complementary patterns and spacing of Hydrogen bond donors and acceptors to recognize cytosine (C).

Guanine-Base-Reader (GBR): A class of molecule, natural or manmade that contains a predetermined pattern and spacing of Hydrogen bond donors and acceptors fixed in space on a molecular scaffold to allow the Base-Reader to bond and recognize guanine (abbreviated G). A few examples of a GBR class of molecule are cytosine (C) and 5-Methylcytosine. These molecules have complementary patterns and spacing of Hydrogen bond donors and acceptors to recognize guanine (G).

Thymine-Base-Reader (TBR): A class of molecule, natural or manmade that contains a predetermined pattern and spacing of Hydrogen bond donors and acceptors fixed in space on a molecular scaffold to allow the Base-Reader to bond and recognize thymine (abbreviated T) and or uracil (U). A few examples of a TBR class of molecule are adenine (abbreviated A) and Coenzyme A. These molecules have complementary patterns and spacing of Hydrogen bond donors and acceptors to recognize thymine (T) and uracil (U).

Base Pair Reader: A class of molecule, natural or manmade that contains a predetermined pattern and spacing of Hydrogen bond donors and acceptors fixed in space on a molecular scaffold to allow the Base Pair Reader to bond and recognize a G-C or C-G pair or a A-T or T-A pair.

For additional glossary of terms, see pages 73-77 of U.S. provisional 61/103,019.

EXAMPLES

Example 1

DNA Translocation Through Single-Walled Carbon Nanotubes

Figure 34B:
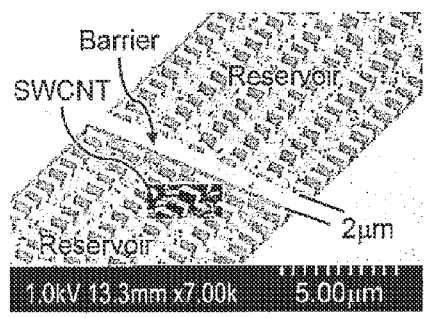
Figure 34C:
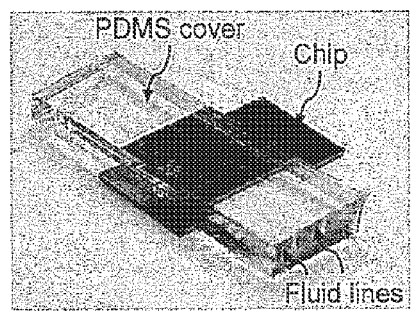

To test the possibility that tunnel signals could be generated by smaller CNTs, we built a nanopore-like device (FIG. 34) was built using lithography. Commercially-available MWCNTS (4 to 5 nm diameter) were spread on a silicon wafer, located relative to fiducial marks on the chip using low-voltage SEM, then covered in 700 nm of PMMA. E-beam lithography was used to create a series of wells in the PMMA lying on the path of a CNT (FIG. 34B). The exposed regions of the CNT in the wells were removed with an oxygen plasma, leaving intact CNT segments that connect adjacent wells. The device was completed with a molded PDMS microfluidic cover that allowed injection of fluids into and out of the reservoir wells (FIG. 34C). SWCNT (<1 to 2 nm diameter) devices were made by CVD growth from Co nanoparticles followed by the same set of lithographic steps.

Figure 35B:
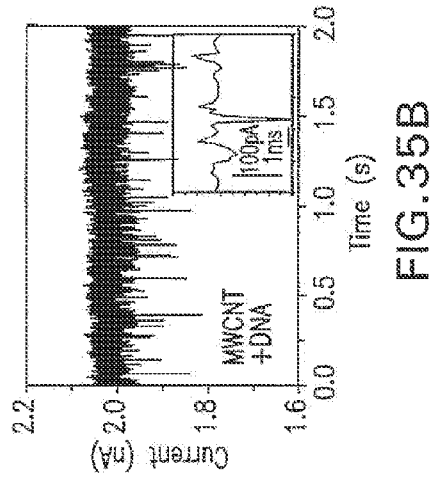
FIG. 35: Special mode of transport for DNA in a "tight" nanotube: (A) current through 5 nm MWCNT prior to DNA addition and (B) after addition of 0.1 nM 60 nt Oligo. (C) 2 nm SWCNT signal prior to DNA addition and after addition (D) of same DNA as above, and shows current over a 10 minute interval (vertical lines are 2 minute markers). This tube gave about a spike (red arrows) per minute. The unstable background is characteristic of DNA addition and not seen for salt alone. Tubes less than 2 nm diameter give no translocation. Bias=0.2V3 electrolyte is 2M KCl.
Figure 35D:
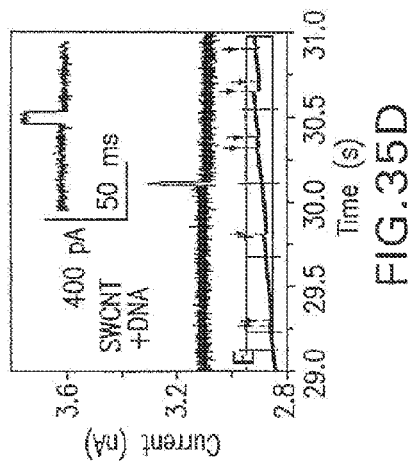
Figure 35A:
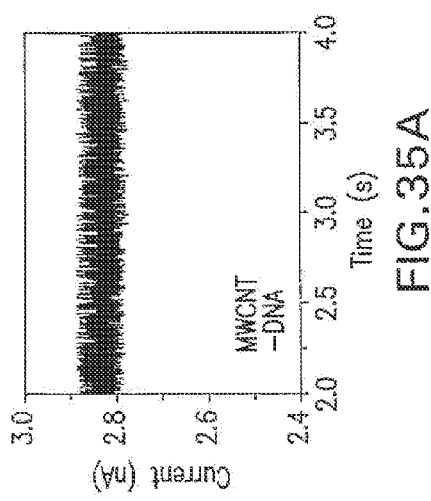
Figure 35C:
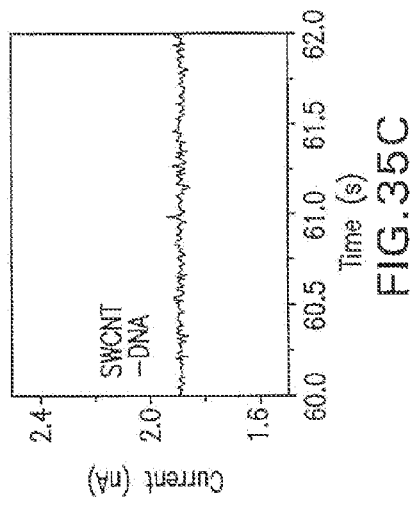
Figure 36A:
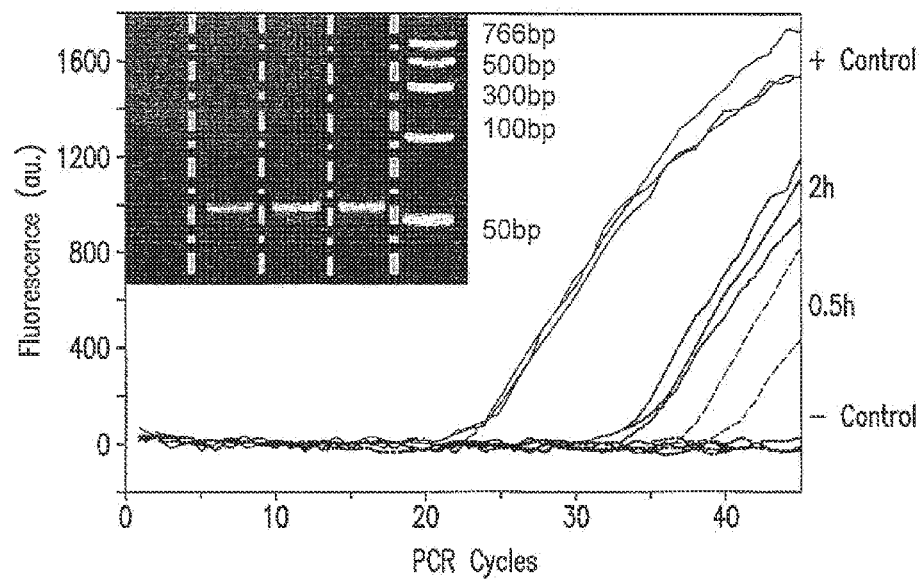
FIG. 36: Many molecules translocate per current spike. (A) Typical qPCR signal for controls and two different translocation times. Product is verified by gels and also direct sequencing. (B) Number of molecules translocated vs. number of spikes. Uncertainties are owing variable filter performance and cut-off criteria for counting spikes. The slope (100 molecules per spike) is clearly much larger than one.
Figure 36B:
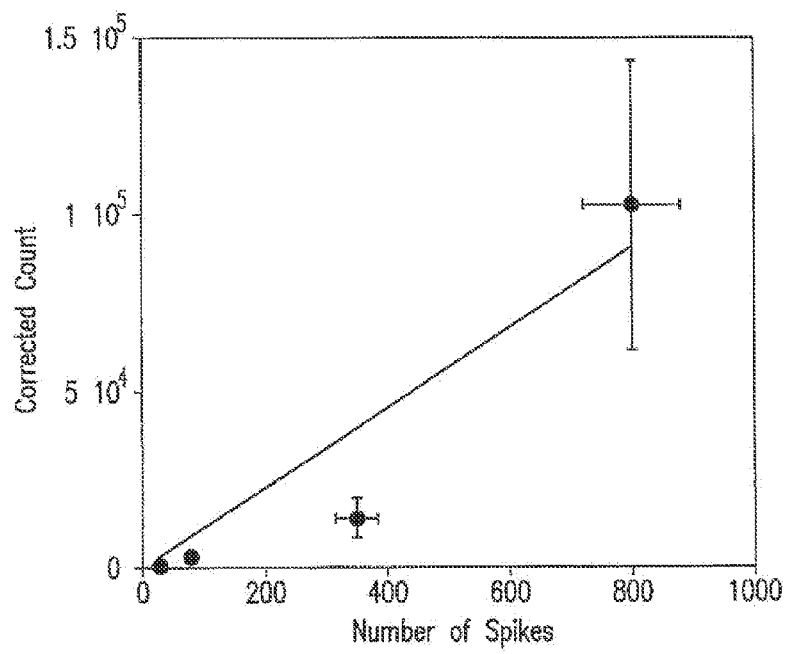

5 nm MWCNT tubes showed fast (µs—limited by the electronics) current blockade pulses when 60 nt ssDNA oligomers were introduced into the 2M KCl electrolyte (FIGS. 35 A and B). Signals from the SWCNT tube devices were quite different. Introduction of the oligomers resulted in much longer pulses (30 ms) of increased current (FIGS. 35 C and D). Translocation events were much rarer (a spike per minute in the example shown, increasing to 10 spikes/sec at 0.5V). In order to confirm that these unusual pulses were indeed associated with DNA translocations, we carried out quantitative PCR (qPCR) on aliquots collected from the output reservoir. Control samples ("(-) control") were collected prior to initiating translocation. A typical qPCR output is shown in FIG. 36A. The (-) control shows no DNA even after 45 cycles. Samples collected after translocation gave the green curves (0.5 h translocation) and the red curve (2 h translocation). A (+) control (blue curves) was used for calibration. Data were quantified by correcting for dilution and filter losses (the main source of uncertainty) and a plot of the number of molecules translocated vs. the number of spikes for four different devices is shown in FIG. 36B. The amount of DNA translocated is indeed approximately proportional to the number of translocation spikes, however, the slope of this plot implies that about 100 molecules translocate for each pulse.

We carried out control experiments using devices with unopened SWCNTs and devices exposed to oxygen plasma but containing no tube. Only in devices containing cut SWCNTs did we see spikes (with the corresponding DNA translocation). In addition, we found that (a) Translocation requires at least 0.2V across the tube, the frequency and intensity of spikes increasing as the bias is increased. (b) Translocation requires at least 50 mM KCl, and the frequency of spikes increases with salt concentration above this threshold. (c) Ion mobilities appear to be enhanced by about 2 orders of magnitude in the SWCNTs, consistent with the outcome of membrane experiments. (d) Pulse widths and intensities vary considerably from tube to tube and even within a run, but are generally on the order of 30 ms with the intensities being about 10% of the background conductance. (e) Pulse widths do not change significantly with bias.

Figure 37A:
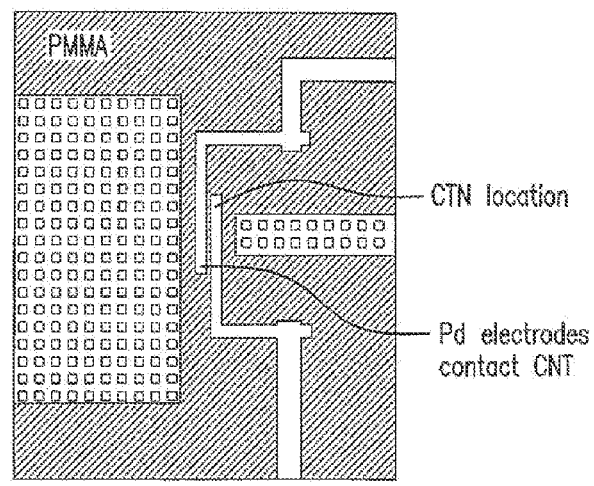
FIG. 37: Wetted CNTs conduct. (A) Device with pair of Pd electrodes contacting CNT under PMMA barrier. (B) Current through CNT as a function of back-gate voltage for dry (red, black) and wet (green blue) tube.
Figure 37B:
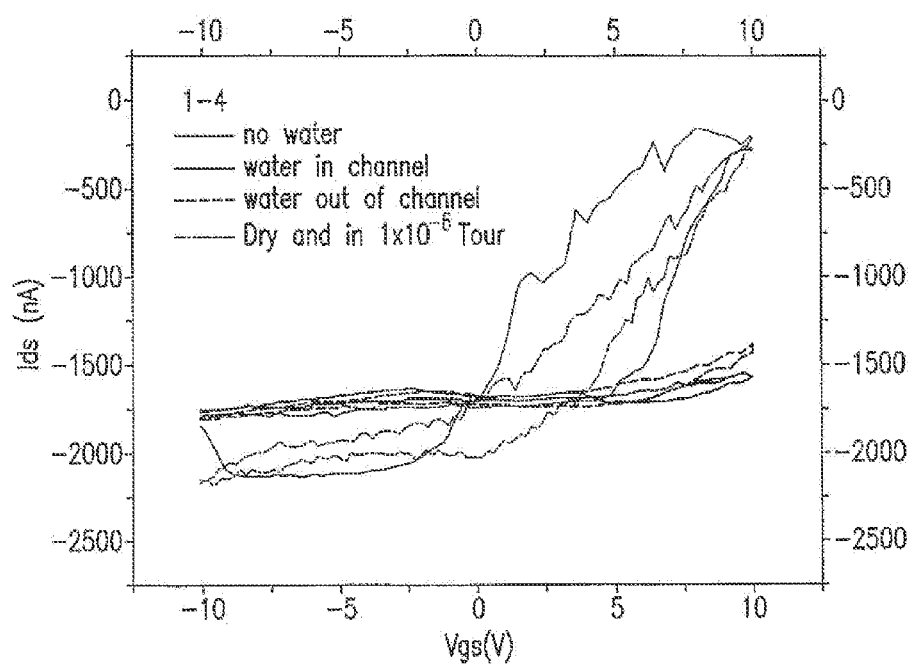

We also measured the electronic properties of the SWCNT directly in a device with two palladium electrodes crossing the tube underneath the PMMA barrier (FIG. 37A). This tube was semiconducting, and we used the underlying silicon as a back-gate to turn the tube on (red trace FIG. 37B). However, once the inside of the tube was wetted (blue and green traces) it remained "on," only returning to its semiconducting state when water was removed in high vacuum (black trace). Thus, it appears that the tubes are all conductive (being either metallic or "turned on" semiconductors). This unexpected result has some precedent in the better known adsorbate-induced surface conductivity of diamond. This would imply that there is little electric field inside the tube to move DNA once it has entered. Thus the DNA may stick in the tube until rammed in further by another molecule entering. If the tube had to fill and/or empty cooperatively, this could account for the 100:1 ratio of molecules to translocation spikes, since the ratio of the length of the tube (2 μm) to the length of the DNA (20 nm) is also 100:1. Clearly this hypothesis can be tested using different oligomer lengths and different CNT lengths. This mechanism has obvious implications for the control of translocation.

Example 2

Synthesis of Trans-Base-Pair Readers with Amide and Thiol Linkers

Propargyl amine and propargyl thiol are used as the molecular linker for attachment of the trans-base-pair readers to CNT and metal electrodes respectively. Our S™ data has shown that the propargyl group is a suitable molecular linker in terms of conductivity and flexibility. These linkers are synthesized and incorporated into the trans-base-pair readers in their amine and thiol protected forms: N-propargyltrifluoroacetamide and propargyl S-thiobenzoate. We have developed an in situ method to remove these protecting groups before use without need of further purification. The Sonogashira Reaction will be employed for incorporation of the molecular linkers into the trans-base-pair readers as discussed in the following sections.

Synthesis of molecular linker functionalized [1,8]Naphthyridine-2,7-diamines

Figure 40:
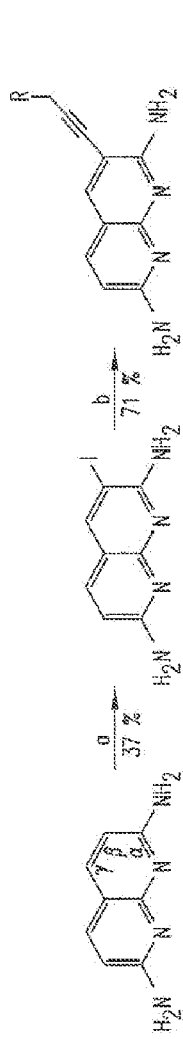
FIG. 40 provides Scheme 1 to synthesize a base-pair reader.

[1,8]Naphthyridine-2,7-diamine has been synthesized using a procedure reported in literature. We have developed a facile method to incorporate propargyl S-thiobenzoate into the β position of the naphthyridine as shown in Scheme 1 in FIG. 40. The naphthyridine was first iodinated with iodine and then reacted with propargyl S-thiobenzoate under the Sonogashira conditions. Apparently, the yield of the first step is relatively low. We will optimize the reaction conditions for scaling up. We will extend the method to synthesis of propargylamine functionalized[1,8]Naphthyridine-2,7-diamine. Meanwhile, we will develop a method to introduce the molecular linker at the γ position of the naphthyridine. We will design improved trans-base-pair readers as suggested by modeling.

Synthesis of molecular linker functionalized 9H-pyrrolo[3,2-h]cinnoline

The basic structure of a GC trans-base-pair reader (FIG. 38B) is fusion of cinnoline with pyrrole or indole with pyridazine, which poses more challenges to its synthesis than the synthesis of the AT base-pair-reader. We have worked out a number of synthetic routes for the synthesis of the GC base pair reader. One of the possible routes is delineated in Scheme 2 (FIG. 41). Cinnolin-8-amine is used as a starting material, which can readily be synthesized according the published procedure. The first step is to brominate the starting material with dibromodimethylhydantion, followed by reduction of the amine to hydrazine. The pyrrole-2-ethyl carboxylate will be constructed on the cinnoline moiety by means of the classic Fischer reaction. After protecting the NH of the pyrrole ring, the ethyl ester will be hydrolyzed to the acid. The carboxylic acid will be converted to Boc-amine by means of the Curtius rearrangement under the conditions reported by Lebel and Leogane. The incorporation of the molecular linker will be finished in the same way as mentioned above. Both PMB and Boc protecting group can be removed with trifluoroacetic acid simultaneously to complete the synthesis.

NMR Studies on Interactions of the DNA Trans-Base-Pair Readers with the DNA Base-Pairs.

We will conduct NMR recognition studies of the base pairs by these new synthetic trans-base-pair readers in an aprotic solvent, such as chloroform. NMR titration and temperature dependent measurement allows us to determine association constants, association enthalpies and entropies, and 2D NOE may allow us to establish the hydrogen bonding modes. Four natural nucleosides will be used as target molecules. All the nucleosides, base readers and trans-base-pair readers will be modified to improve their solubility in the NMR solvent without impairing their hydrogen bonding capacities. First, we will study interactions of base readers with four natural nucleosides, determining the base reading specificity and affinity. Next, we will study the base pair recognition by trans-base-pair readers. We expect to achieve two goals from the NMR studies: (1) establishing thermodynamics of the recognition of base and trans-base-pair readers; (2) confirming their recognition patterns. Combining chemical information with their electronic properties will allow us to design the next generation of trans-base-pair readers using computer modeling.

Example 3

Attachment Schemes

Design and Modeling of Trans-Base-Pair Reader Reagent Attachment Schemes.

Oxygen-plasma etching of CNTs leaves the ends predominantly functionalized with carboxylic acid residues, so amide linkages can readily be made. However, our device requires different reagents on each electrode. There are currently three options, each of which will be explored as required to produce the required degree of functionalization of each electrode:

Random Functionalization.

Figure 39:
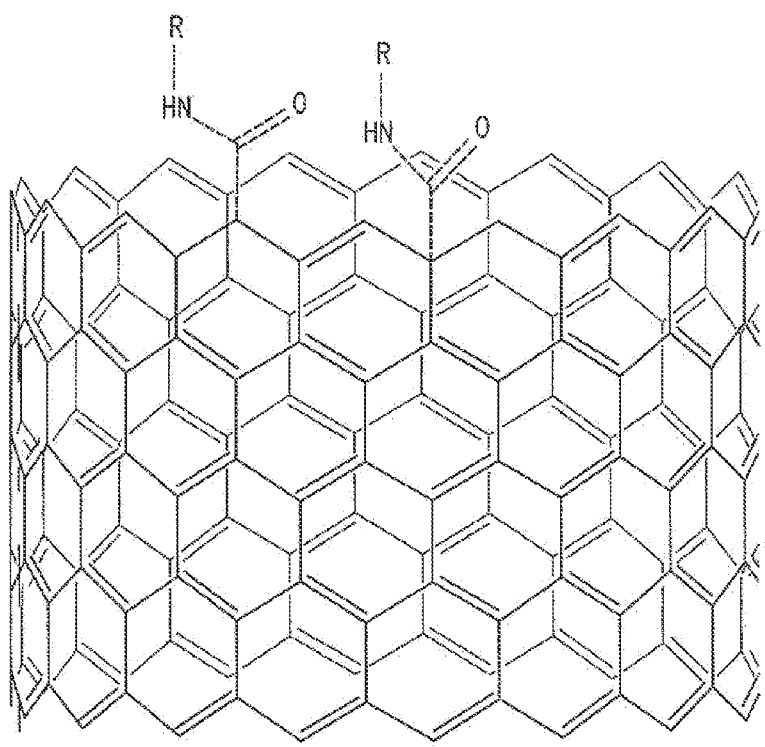
FIG. 39: Showing two sites (red, green) for amide linkages on an 18,0 CNT (of the required 2 nm diameter). A total of 36 sites are available in this model.

There are many sites available on the ends of 2 nm diameter tubes (FIG. 39). If the probability of each reagent binding a particular site is equal, then on the 18,0 tube shown, the probability that each site on a given tube binds just one of the two reagents is (0.5) which is vanishingly small. In practice, not every site will be reacted and there is the possibility of fruitless assemblies with the target base across the end of one tube. These may not matter if fluctuations drive an assembly across the electrodes frequently enough.

Electrochemical Functionalization.

Figure 46:
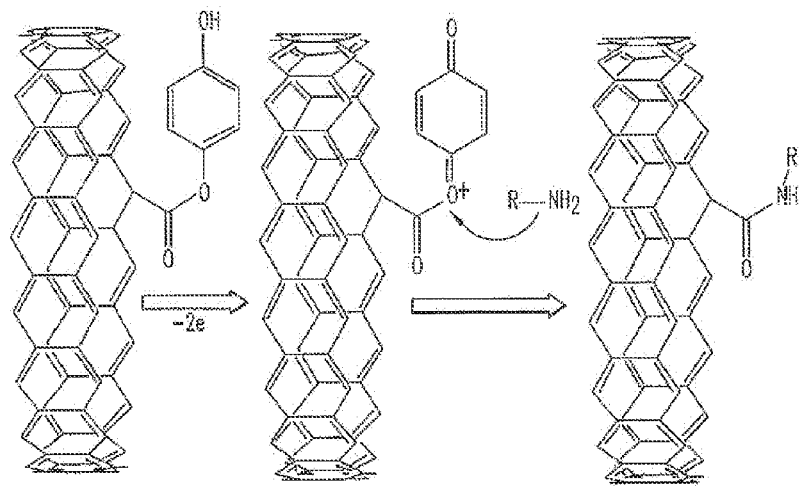
FIG. 46 Selective attachment of DNA base reader (R) by electrochemical oxidation at one of the electrode ends of a hydroquinone-functionalized CNT gap.
Figure 47A:
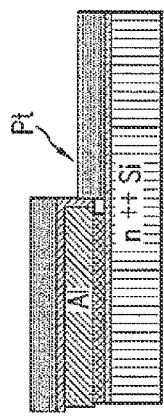
FIG. 47: Heterogeneous junction without EBL; (A) A thin layer of Aluminum is patterned. (B) Exposed CNT is etched by $O_2$ plasma with nanometer over-etch and Al is slightly oxidized. (C) Structure is coated with Pt to form a Pt electrode facing the CNT across a gap. (D) Metal electrode is patterned overlapping with Al. (E) Oxide etch, lift off, leaving CNT-metal nanometer gap, the Al will be oxidized again to form insulating Alumina oxide layer. (F) SEM showing 4.5 nm junction. (G) Corresponding tunnel characteristics confirming gap size.
Figure 47B:
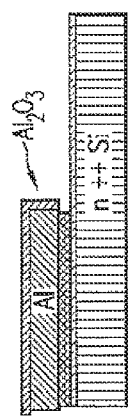
Figure 47C:
Figure 47D:
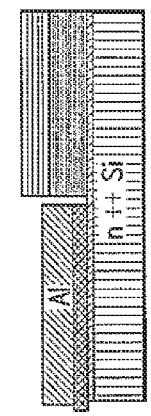
Figure 47E:
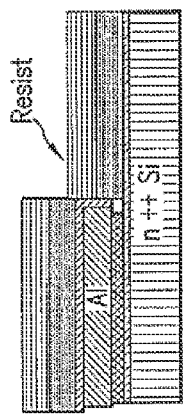
Figure 47F:
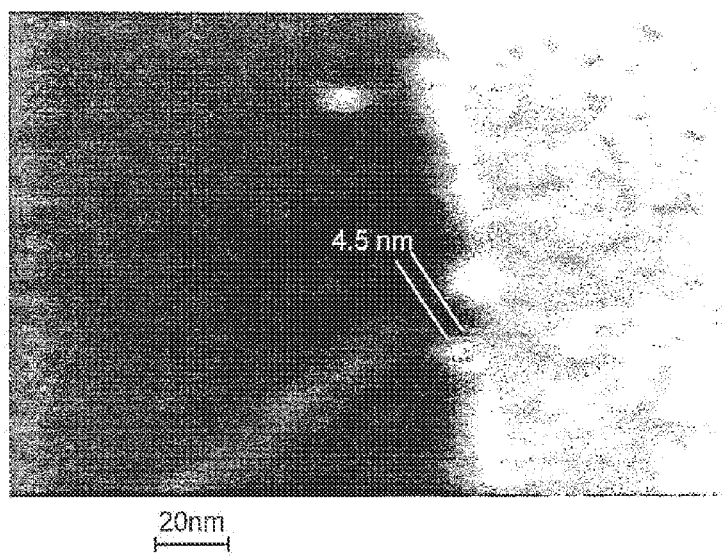
Figure 47G:
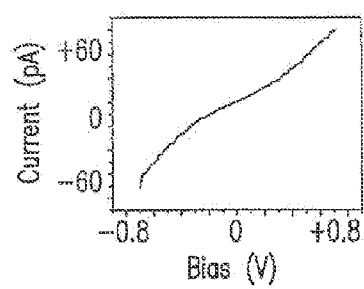

The use of electrochemistry to generate a reactive species only in the immediate vicinity of one electrode is a well-developed technology. The challenge here lies with confining electrochemically-generated reactive species to just one electrode in a gap of nanometer dimensions. Selective electrochemical functionalization of SWCNTs by reduction of aryl diazonium salts has been widely used since its introduction and it is claimed to be localized to within 1 nm. The diazonium radical attaches to any $sp^2$ hybridized carbon so the process is not very selective, though it does appear to functionalize the ends of tubes preferentially. This will be one approach we will try. A more attractive possibility is the oxidation of hydroquinone-modified tubes, to produce benzoquinone as a good leaving group. This scheme is shown in FIG. 46. The hydroquinone is first coupled to the carboxylate residues on the CNT with EDC or DCC chemistry. It is selectively oxidized on one electrode to benzoquinone in the presence of the amine-terminated trans-base-pair reader, which is attached to the CNT by an amide linkage in one step. The electrode to be functionalized will be poised at the oxidation potential with respect to a reference electrode. The process will be repeated on the second electrode with an amine-functionalized base. We expect that oxidation potentials will be modified a little by the close proximity of the second electrode but the effect can be minimized by operating at high electrolyte concentration.

Analysis of the functionalization is also challenging on this length scale. Goldsmith et al. describe some remarkable electrochemical measurements on SWCNTs that lead us to believe that useful electrical signals may be obtained even on these small length scales. They also describe an ingenious approach for detecting modified sites based on imaging bound functionalized gold nanoparticles in an SEM, a technique we will apply here.

Metal-CNT Gap.

Below we outline an alternative strategy for fabrication of a metal-CNT tunnel gap. This has the advantage of eliminating all nanofabrication steps and making small (nm) gaps routinely between a CNT and a metal electrode. Orthogonal attachment chemistries are then readily available (e.g., amide linkages to the CNT and thiol linkages to the metal).

A CNT to Metal Electrode Gap.

We have a method to create small gaps using an overhanging oxidized layer on aluminum, illustrated in FIG. 47 and described for the case of metal-metal junctions elsewhere. The result is a device in which a Pt electrode faces a CNT over a gap of a few nm. These devices are fairly straightforward to fabricate, and we will first characterize translocation in such devices using the methods described above. If reliable translocation is obtained, we will then proceed to functionalize the devices using amide linkages to the CNT and thiol linkages to the Pt. We will characterize the devices and compare their performance to devices based on CNT gaps.

Characterize Base Reading and Incorporation of Translocation Control.

We will use nucleotides to characterize signals arising from the capture of matched and mismatched targets, much as was described for gold-gold junctions, comparing the signals to the results of the simulations described above. We have allowed for one complete cycle of refinement (theoretical modeling and design, synthesis and characterization) driven by the insights gained from these first rounds of tests. This will also represent our first opportunity to check the interplay between translocation bias and reading bias and we will study these effects with small oligomers. We have emphasized changes in conductance as a readout mechanism, but we expect changes in the lifetime of the bonded complex to be an important signal too. We further expect these lifetimes to be exponentially-sensitive to the force pulling on the DNA. We will characterize the interactions between translocation and readout to characterize the way in which the readout is affected by the electrophoretic force on the translocated DNA and compare our results to computer models Example 4

Determining Tunnel Conductance of a Single Hydrogen Bonded Pair

Here, we report on "telegraph-noise" measurements made by forming a fixed gap between a probe functionalized with a DNA base and a surface functionalized with nucleosides.

We synthesized the nucleosides 5'-S-acetyl-5'-thiodeoxycytidine and 5'-S-acetyl-5'-thiothymidine following published protocols. These compounds were employed to prepare the nucleoside monolayers on freshly-prepared Au(111) substrates using the method developed in our lab. Gold STM probes were prepared and functionalized with 8-mercaptoadenine (A), 2-amino-8-mercaptoadenine (2-AA) and 8-mercaptoguanine (G) as previously described. The Watson-Crick base pairings are shown below for (i) adenine-thymidine, (ii) 2-aminoadenine-thymidine and (iii) guanine-deoxycytidine.

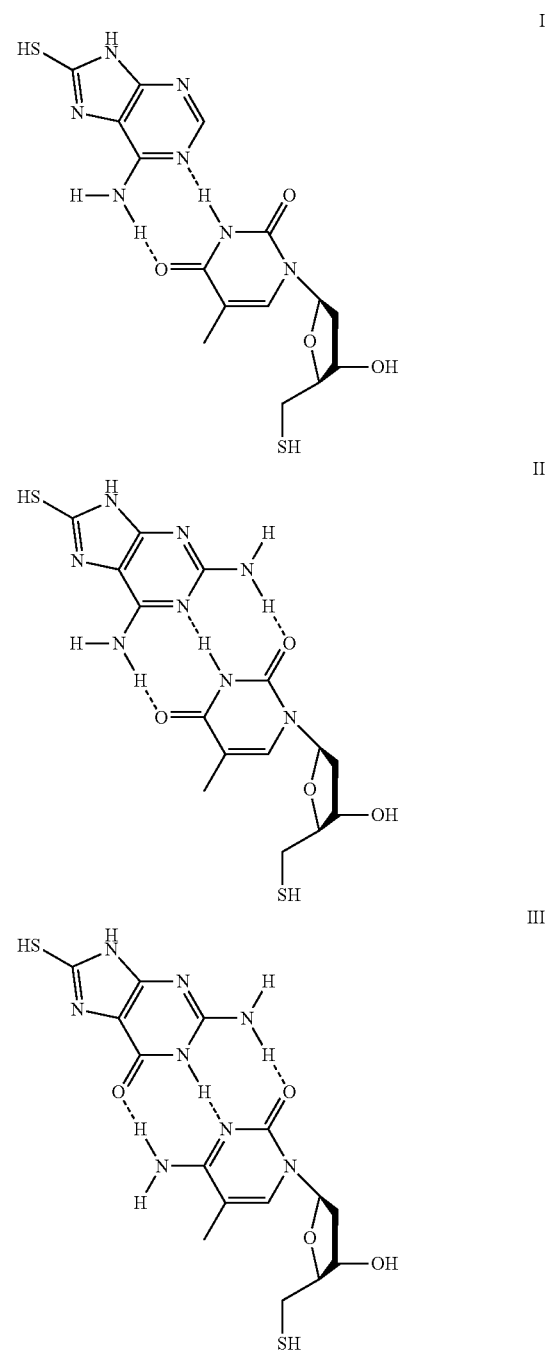

We also prepared STM probes and gold substrates functionalized with a monolayer of thiophenol as controls. Further controls employed bare gold probes or substrates. Measurements were carried out on a PicoSTM (Agilent, Chandler) with the sample and probe submerged in 1,2,4-trichlorobenzene. The system was first left to stabilize for three to four hours, and then the probe was advanced towards the surface to achieve a chosen set-point current ($I_{SP}$) at a tip to substrate bias, $V_b$. Immediately after the set-point was achieved, the servo-control was broken using custom LabView software, and the tunnel current recorded as a function of time using a digital oscilloscope. The tunnel junctions remained stable without servo control for up to ten seconds.

Figure 48A:
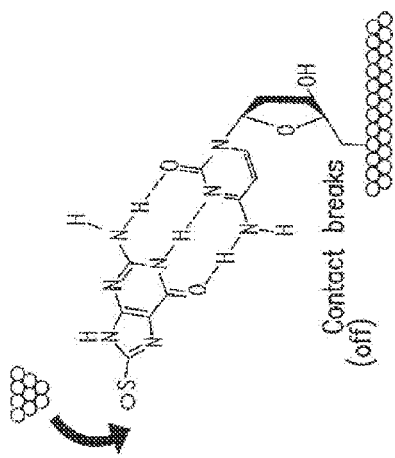
FIG. 48: (a) An intact junction in which the tunnel gap is spanned by a guanine attached to the probe, hydrogen bonded to a deoxycytidine attached to the substrate. (b) Fluctuations that break the metal-molecule contact will reduce the conductance, as will fluctuations that break the hydrogen bonds (c). (d) An example of the telegraph noise signal produced as bonds break and reform.
Figure 48B:
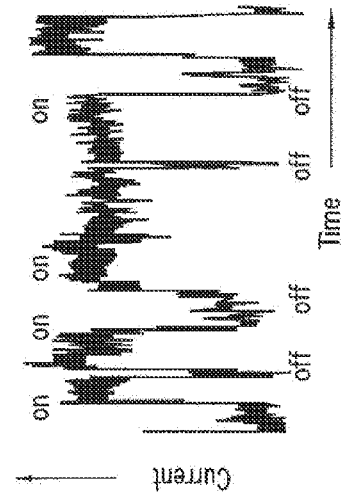
Figure 48C:
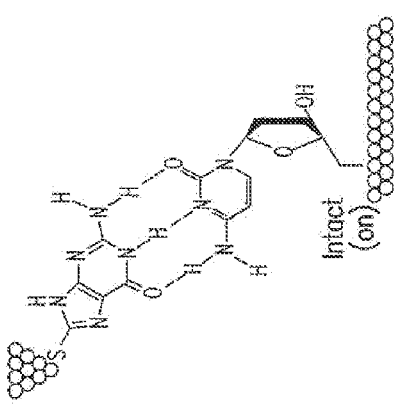
Figure 48D:
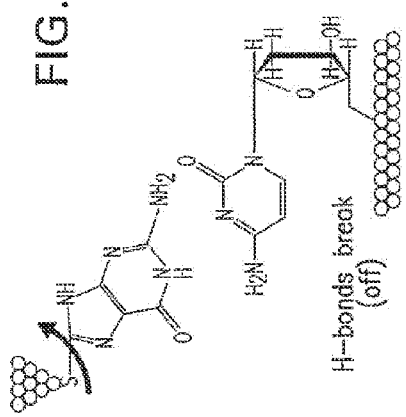

In the hydrogen bonded systems, bursts of "telegraph noise" like that shown in FIG. 48*d* were recorded in about half the data collection runs. Usually (>95% of the data collected) the noise reflected stochastic switching between just two distinct levels, indicative of a single base-nucleoside pair fluctuating in the junction. Some bond-breaking possibilities are illustrated in FIG. 48. The molecule-metal contacts may "break" (FIG. 48*b*) as in the case of similar recordings from simple bis-thiolated molecules. The motion in the figure is exaggerated for effect, for the frequent re-connection suggests only a small motion of the contact (which is probably not at the Au—S bond, but rather at the Au—Au bonds that surround the Au atom attached to the S atoms—motion in many such thiol-tethered systems is also affected strongly by interactions with the surrounding molecular matrix.) Simultaneous breaking of all the hydrogen bonds (FIG. 48*c*) is yet another possibility for the systems studied here, and it appears that both processes contribute to the observed telegraph noise, as evidenced by a bimodal distribution of switching times (see below).

Figure 49A:
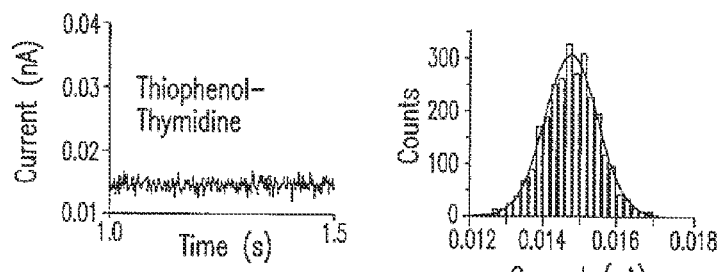
FIG. 49: Recordings of tunnel current vs. time (left column) together with the corresponding distributions of current for (a) a control junction with thiophenol on the probe and thymidine on the surface, (b) adenine on the probe and thymidine on the surface, (c) 2-aminoadenine on the probe and thymidine on the surface and (d) guanine on the probe and deoxycytidine on the surface. Solid lines are Gaussian fits to the upper and lower switching level distributions. These fits are used, together with the bias, to determine the molecular switching conductance in a given run. High-current switching data are given in FIG. 53.
Figure 49B:
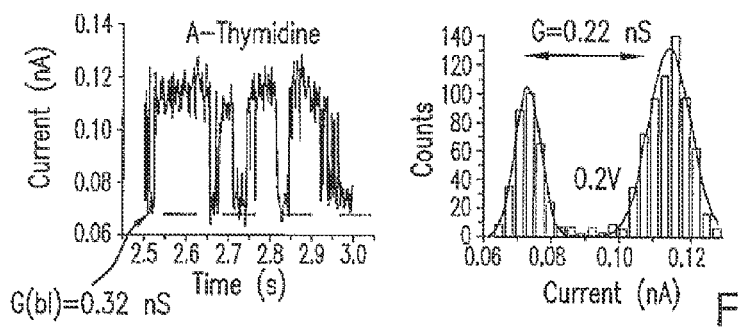
Figure 49C:
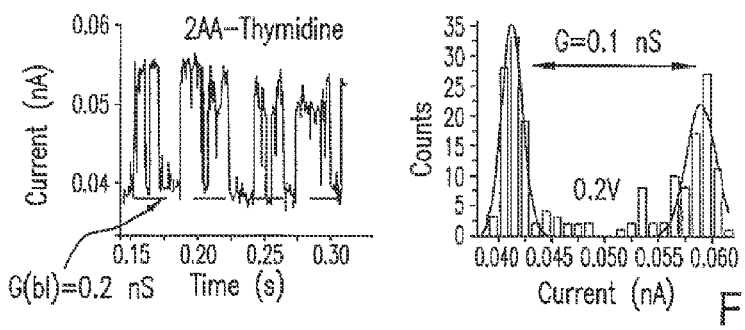
Figure 49D:
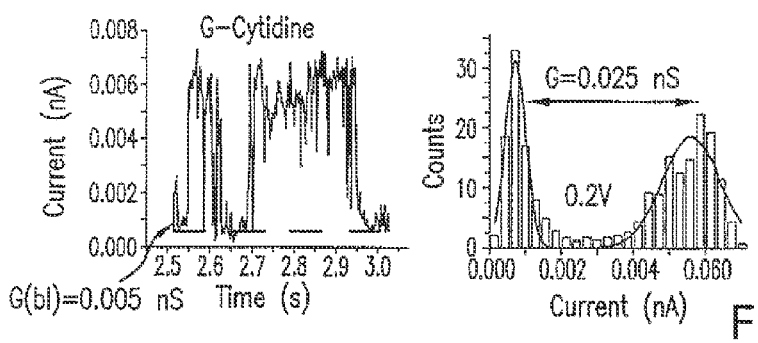

The result of a typical control experiment (thiophenol probe, thymidine monolayer) is shown in FIG. 49*a* with a current trace for 0.5 s worth of data on the left, and a histogram of the current distribution on the right. The current noise is distributed evenly around the mean. In contrast, the H-bonded systems (FIGS. 49*b*, *c* and *d*) all show distinct telegraph noise with a corresponding bimodal current distribution. We characterized the frequency with which telegraph signals occurred as follows: once the instrument was stabilized and a signal first recorded, we measured the fraction of each 5 s run occupied by telegraph noise. These fractions are shown as percentages in Table 1. For control experiments where telegraph noise was not seen at all ("0" in Table 1) we followed the same stabilization procedure and then recorded current data for the same overall experimental duration. Interestingly, thiophenol on the probe or substrate did show rare (few percent) instances of telegraph noise in contact with a base or nucleoside but only at the very lowest bias used. Presumably, interactions between the aromatic benzene ring and the heterocycle can occasionally result in complexation. These rare exceptions aside, the experiments summarized in Table 1 show that the entire metal-thiol-molecule-H-bonds-molecule-metal system needs to be assembled for telegraph noise to be observed.

TABLE 1

Observed frequency of switching (fraction of time occupied by telegraph noise in a 5 s run) for various preparations of the probe (left column) and the surface (top row).

| | Thio-thymidine | Thio-deoxycytidine | Thiophenol | Bare |
|---|---|---|---|---|
| 8-Mercapto-adenine | 47 ± 8% | — | 1 ± 0.3%* | 0 |
| 8-Mercapto-2-aminoadenine | 51 ± 7% | — | — | 0 |
| 8-Mercapto-guanine | — | 52.5 ± 13% | — | 0 |
| Thiophenol | 2.5 ± 1%* | — | 0 | 0 |
| Bare | 0 | 0 | 0 | 0 |
| Adenine | 0 | — | — | — |
| 2-Aminoadenine | 0 | — | — | — |

Errors are ±1sd.
"—" represents untried combinations.
*indicates that the observed switching only occurred at low bias (50 mV).
The bottom two rows are for bases physisorbed onto the probes (no thiol attachments).

Figure 50A:
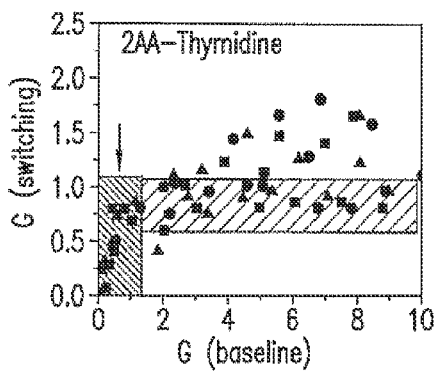
FIG. 50: Plot of molecular switching conductance vs. baseline conductance for the three base-nucleotide combinations (a-c). (d) illustrates mechanisms for the various regions. For (1) the tunnel gap is larger than the equilibrium length of the molecular pair, leading to a region of rapid increase in conductance (shaded gray in a-c) as the strain required to span the gap decreases. When the gap is equal to or smaller than the equilibrium length of the molecular pairs, they may span the gap in either the equilibrium configuration (3—shaded green in a-c, $\theta$=0) or tilted configurations (2—unshaded data in a-c). The applied biases were 0.05V (squares), 0.1V (circles) and 0.2V (diamonds).
Figure 50B:
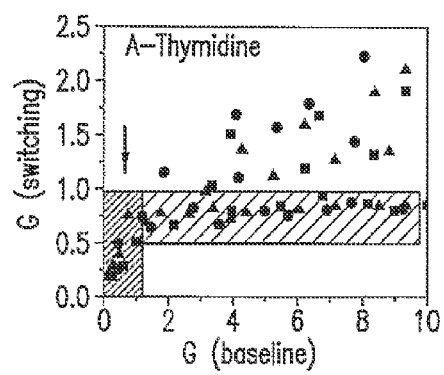
Figure 50C:
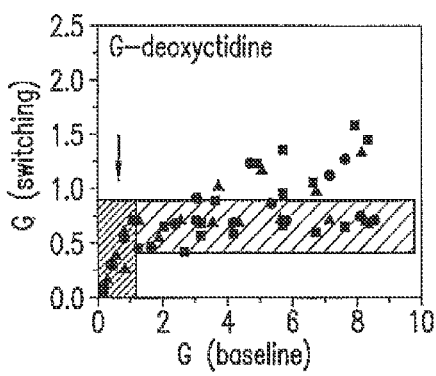
Figure 50D:
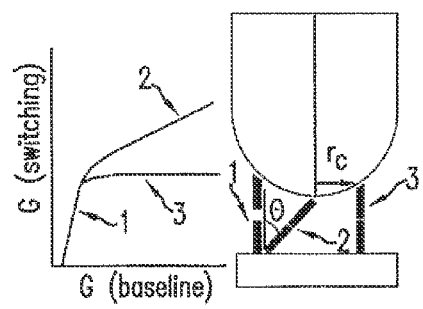

Haiss et al. have found that the measured conductance of a rigid molecule increased approximately exponentially as the tunnel gap was made smaller, an effect they attributed to movement of the molecular levels relative to the Fermi level as the molecule is rotated towards the surface. In the present, more complex system, the measured switching conductances display a variety of dependences on the baseline conductance (G(bl) in FIG. 49), shown for the three types of molecular pair in FIG. 50. We have chosen to plot the switching conductance vs. G(bl) rather than against the gap value itself because of the rather complex relationship between gap and conductance in these systems. Plotted this way, an exponential increase in conductance with gap appears as a linear increase of conductance with G(bl). In all cases, the switching conductance increases rapidly with G(bl) at first (gray shaded boxes, FIG. 50*a-c*). Above a critical conductance (similar in all three cases, and marked by an arrow) the switching conductance takes on a broad range of values. The upper limit clearly increases linearly with G(bl), consistent with the tilting mechanism described by Haiss et al. (though other types of distortion are surely also possible in this more complex system). However, about half of the total data points (green shaded boxes) lie on a plateau of constant conductance. One interpretation of these data is shown in FIG. 50*d*. In the region labeled "1", the gap is too large to be spanned by molecular pairs at their equilibrium spacing, so molecular-pairs that do span the gap are strained, with a conductance that falls exponentially with strain (i.e., falls linearly as G(bl) falls). Once the gap becomes equal to the length of an unstained molecular pair, further decreases in the gap result in an increase in molecular switching conductance, possibly owing to the tilting mechanism described by Haiss et al. This is the region labeled "2". However, the smaller gaps should also accommodate a number of molecular-pairs of equilibrium length at some critical radius of the probe ($r_c$ in FIG. 50*d*), resulting in a plateau of constant conductance ("3", shown as the green shaded region). The onset of this plateau will occur when the gap can first just accommodate an unstrained molecule, presumably at the point marked by the arrows on FIG. 50. Molecules attached at intermediate points in smaller junctions ($0 < r < r_c$) will generate conductances that lie in between these two limits, generating data points above the plateau, but smaller than the maximum values measured. Haiss et al. discuss these possibilities, but conclude that their experiments capture molecules only at the minimum gap, because molecules are pulled into this region by the tip-sample electric field. Our experimental arrangement is different, because one half of the molecular pair is attached to the probe before the junction is made. Thus, we believe that all geometries can be captured in gaps smaller than the critical value. It is also possible that other arrangements such as bent nucleoside-base-pairs could occur. Both geometry (the number of available sites increasing with available tip radius) and energetics (equilibrium molecular pairs have the lowest energy) favor equilibrium pairs, and we find that about half the total data points lie in region 3.

Figure 51:
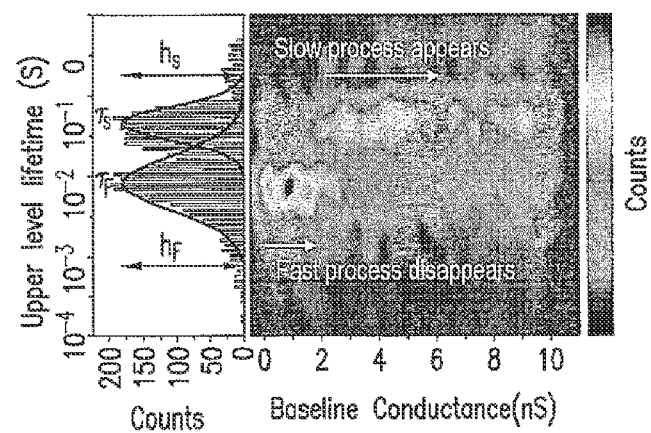
FIG. 51: Distribution of "on" times for G-deoxycytidine (left). The distribution is plotted as a function of G(bl) in the 2D color plot on the right (red=high counts). Parameters obtained from Gaussian fits ($\tau_F$, $\tau_S$ and $h_F/h_S$) are listed in Table 2. Data for the other base-nucleoside pairs are given FIG. 54.
Figure 54A:
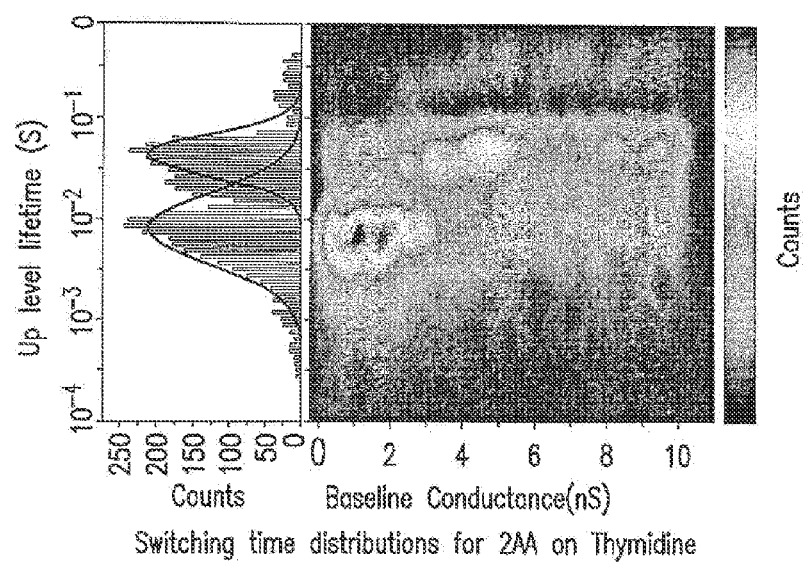
FIG. 54 provides data for additional nucleoside pairs.
Figure 54B:
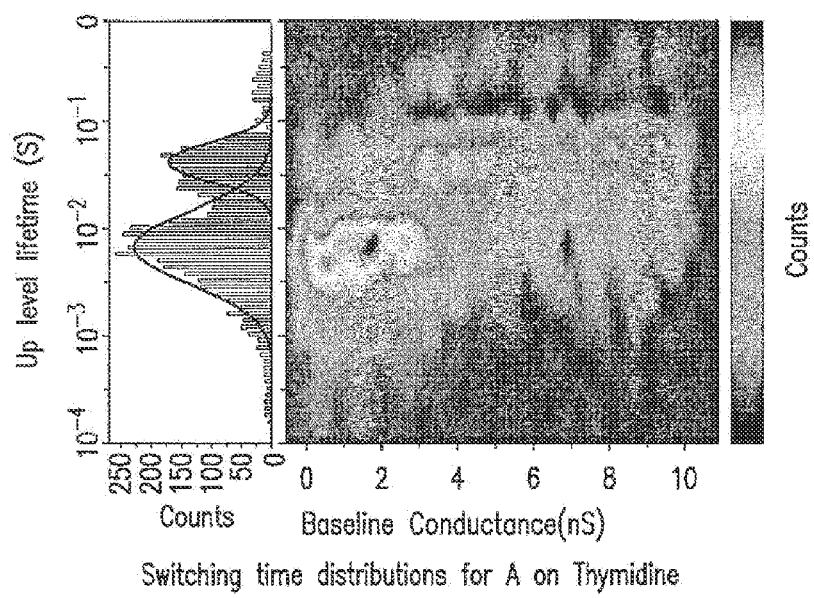

Support for two different types of bonding (stretched vs. equilibrium and equilibrium but tilted) can be found in an analysis of the switching times. The peaks in all the bimodal current histograms are well separated, so the duration of the on-state is easily extracted by recording the intervals for which the current remains above 50% of the switching range in a given run. We plotted distributions of these switching times using logarithmic histograms and data for the G-deoxycytidine pair are shown in FIG. 51 (similar plots for the other base-nucleotide combinations are shown in FIG. 54). The distribution of switching times is clearly also bimodal. We fitted Gaussians to the two peaks ("F"=fast, ~8 ms, "S"=slow, ~50 ms) and the fitting parameters are listed in Table 2 for all three base-nucleoside combinations. The fast peak is somewhat faster and noticeably more prominent in junctions held together by two hydrogen bonds (A-thymidine) compared to junctions held together by 3 (G-deoxycytidine, 2AA-Thymidine). Further, the timescales are very similar to the characteristic times for opening of DNA bases in a double helix. Thus, the fast process appears to be a consequence of H-bond opening of the complex (FIG. 48 c). The slow peak does not appear to change with H-bonding. In view of the similarity with the timescale for opening of thiol-gold contacts we ascribe this feature to fluctuations in the molecule-metal contact (FIG. 48b). The distribution of switching times is broken down as a function of baseline conductance in the 2D plot on the right of FIG. 51 (and see FIG. 54).

functional methods have been used to calculate the conductances of these base-nucleoside pairs and the results of these calculations are reproduced in the third column ($G_{pred}$) of Table 2. It is striking that the conductances obtained from the plateau regions agree with the predicted conductances within a factor of two, remarkably good agreement in the field of single molecule conductance measurements. Even more strikingly, the surprising prediction that G-deoxycytidine (3H-bonds) is less conductive than that A-thymidine (2H-bonds) is supported by this analysis. (This unusual result is, in the theory, a consequence of the different relative position of the Fermi-level in the two cases.).

We have determined the absolute tunnel conductance for A-Thymidine, 2AA-Thymidine and G-deoxythymidine spanning gold electrodes. Further, the analysis of switching conductance as a function of baseline conductance facilitates design of an optimal fixed tunnel gap for readouts of DNA basepairs. Clearly, the gap must be smaller than the critical value at the transition from region 1 to regions 2 and 3. The close correspondence between the measurements and theory for the present case of base-nucleoside interactions adds credibility to the DFT calculations. These same calculations predict very small (fS) conductance across an entire DNA molecule. Thus, electronic sequencing of DNA probably requires readout schemes that involve shorter tunneling paths, and these schemes are currently under investigation in our laboratory.

Electronic Characterization of Trans-base-pair Readers.

We will use the telegraph-noise measurement perfected above to characterize the trans-base-pair readers with, and without target nucleotides in a fixed gold electrode tunnel gap (FIG. 42). Measurements will be carried out in buffered aqueous electrolyte, and we will first obtain baseline data for the

TABLE 2

Measured conductances obtained from the conductance plateau region ("3" in FIG. 3) compared to calculated values ($G_{pred}$).

| Base-nucleoside pair | $G_{meas.}$ (nS) | $G_{pred.}$ (nS) | $\tau_F$ (ms) | $\tau_S$ (ms) | $h_F/h_S$ |
|---|---|---|---|---|---|
| A-thymidine | 0.76 ± 0.01 (±0.03) | 1.62 | 7 ± 3.6 | 46 ± 11 | 1.3 ± 0.1 |
| 2AA-thymidine | 0.80 ± 0.03 (±0.14) | 1.43 | 8.3 ± 3.9 | 45 ± 11 | 1 ± 0.1 |
| G-deoxycytidine | 0.66 ± 0.007 (±0.07) | 0.96 | 8.4 ± 3.4 | 47 ± 11 | 1 ± 0.1 |

Values are best-fits to the I-V curves in FIG. 5 with fitting errors shown.
Error values in parenthesis are derived from the SDs of the single molecule measurements (spread of data in the green boxes in FIG. 50).
Also shown are mean lifetimes ($\tau_F, \tau_S$) with associated halfwidths, and ratios of the peak heights, $h_F/h_S$, for Gaussian fits to the switching time distributions.

The fast process diminishes rapidly with increasing baseline conductance, while the slow process becomes more important with increasing baseline conductance. The turn-over, which starts in the neighborhood of G(bl)=1 nS, begins in about the same place that the molecular switching conductance moves from region 1 to regions 2 and 3 (FIG. 50). This is consistent with the idea that the hydrogen bonding is more stable (less strained) when the molecular pairs span junctions smaller than the equilibrium length of the pairs. The "disappearance" of H-bond openings in very small gaps is unexpected, and possibly reflects the consequences of confining the molecular pair to a very small volume.

Figure 52:
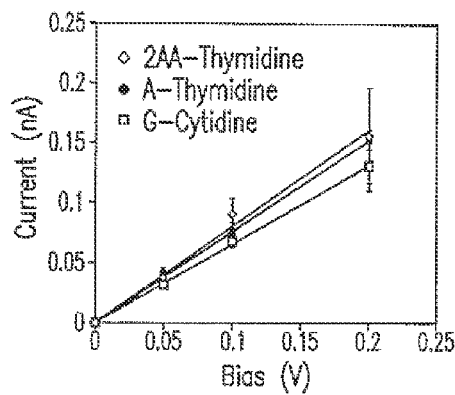
FIG. 52: Current-voltage curves for 2AA-thymidine (diamonds), A-thymidine (circles) and G-deoxycytidine (squares). Each data point is the mean obtained from data with conductances >0.5 nS. The error bars correspond to ±1 sd.
Figure 53A:
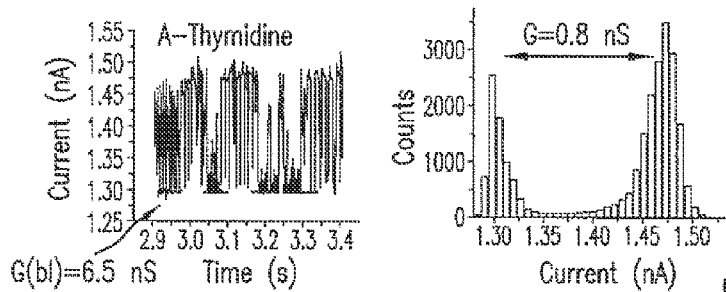
FIG. 53 provides high current switching data.
Figure 53B:
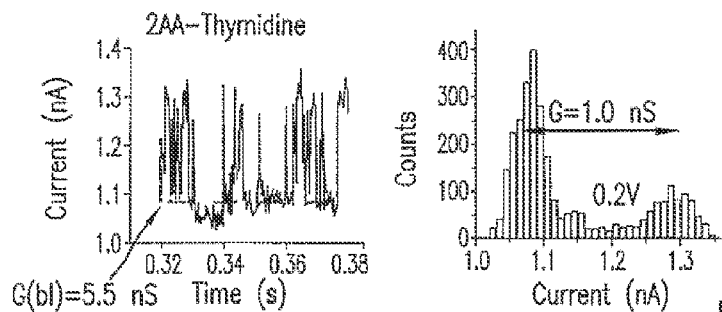
Figure 53C:
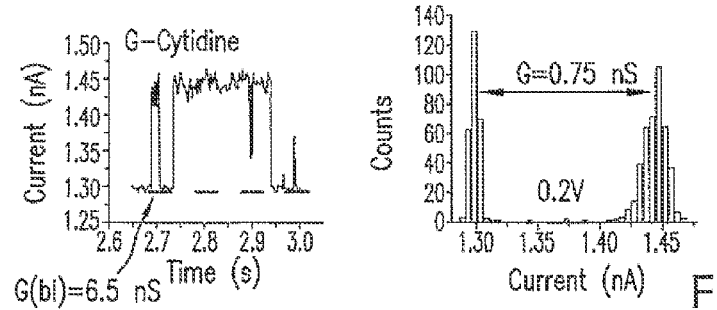

If this interpretation is correct, then the conductance of the relaxed molecular pairs will be given by the data in the plateau regions in the green boxes (region 3) on FIG. 50. Using these data, we plot the mean currents (error bars are ±1sd) as a function of $V_b$ in FIG. 52. The current-voltage relationships for all three Watson-Crick bonded pairs are linear, and the slopes yield the conductances listed in Table 2. Densityreader-pair alone (FIG. 42A, B). We expect to see significant differences when nucleotides are introduced into the solution and bind to the recognition molecules (FIG. 42C, D). This electronic detection of a single nucleotide is a significant milestone, and the resulting signals will yield a distribution of single molecule conductances and lifetimes for the various complexes. These can be compared to the theoretical predictions (for gold-gold junctions) and used to help refine the models discussed above. We will measure signals from each of the four nucleotides, and characterize all of the 12 possible mismatches, once again comparing the data to the predictions, refining calculations as needed. We will determine the effects of high salt and strong buffers, and test the consequences of chemical changes, such as moving the linker attachment site, once again, comparing our measurements to the predictions of theory. These iterations will allow us to refine the theory for the gold-gold junctions, giving us a better starting point for modeling behavior in a CNT gap. The two systems differ substantially (probably requiring different choices of exchange-correlation functional) but the lessons learned from the gold-gold junctions (which we presently have working) will surely be valuable to us in designing the less-familiar CNT gaps.

Example 5

Characterization of DNA Translocation through "Tight" SWCNTs

Testing translocation of DNA through tight SWCNTs experimentally will require translocation of long molecules. As a first step, we will further explore translocation of small oligomers. Our present model predicts that the number of molecules translocated per signal pulse, $N_T$ is given by $$N_T = \frac{L_{CNT}}{L_{DNA}}$$

and this can be tested by varying the length of the SWCNT, $L_{CNT}$ and/or the length of the oligomer, $L_{DNA}$, and measuring the amount of DNA translocated with qPCR. The shortest DNA length we can use is limited by the required PCR primers, while the longest is limited by the precipitous drop in translocation rate as oligomer length is increased in a nondenaturing environment. In practice this allows for a factor 3 in DNA length (60 nt to 180 nt) while tube lengths can be changed over a larger range (2μ to at least 20μ). We do not understand the origin of the positive current spikes in tight tubes (FIG. 35D) but expect that insights will come from the use of salts other than KCl (e.g., LiCl, NaCl, CsCl). Characterization of the spikes is a key requirement for developing feedback control of the translocation process. Progress will be enhanced by improving the yield of devices. The block-copolymer catalyst we currently use yields a most probable tube diameter of about 1 nm, with only a fraction the required 2 nm. Better control of CNT position and size would also shorten the manufacturing process. We will adopt the method reported by Dai et al. to grow SWCNTs at specific locations with specific sizes on an Si wafer. This approach uses e-beam lithography to pattern nanometer sized holes on the photoresist coated substrate. A thin film of Co and Fe is deposited by e-beam evaporation. After lift-off, the substrate is annealed at high temperature. During the annealing, the catalyst atoms diffuse to form small nanoparticles that can be used as SWCNT catalysts. By controlling the diameter of the e-beam patterned hole and the thickness of the catalyst film, the diameter of the nanoparticle is controlled.

Building a Model of Transport in "tight" SWCNTs.

We will perform molecular dynamics simulations to compute the optimal parameters for controlling the motion of a DNA molecule through the interior of the SWCNT as well in the high-field region near the entrance to the tube. The parameters of interest for given dimensions of the SWCNT and the DNA are voltages applied across the reading gaps, the electric field for the DNA electrophoresis through the SWCNT, and the concentration of electrolytes. These simulations will be based on prior experience at Oak Ridge in simulating DNA in aqueous solution. We will use the force fields based on AMBER, UFF and Tersoff-Brenner potentials (REBO, AIREBO). The polarization effect of the conducting CNT will be included using the ECD method. The large scale molecular dynamics packages NAMD and NWCHEM will be used to solve the equations of motion. These codes scale well with large number of processors and are appropriate for large scale calculations. We will perform a series of computational simulations as follows: (1) Perform MD simulations of DNA molecules in aqueous solution of the SWCNT to determine the optimal conditions for the DNA translocation through the pore at an appropriate speed. We anticipate these will be molecular dynamics simulations in a time scale of tens or hundreds of nanoseconds. (2) Project the results to longer time scales. The ideal signature detection timescale in experiments may be well beyond the timescale that standard MD can reach with the current state-of-the-art computational facilities. A series of constrained simulations will be performed at various steps as the molecule moves through the detection gate to measure the external forces required to maintain its translocation and orientation. This will yield a force profile for determining the lower bound for the feasibility of an actual device. The calculations for longer times (up to ms and longer) rely on the solution of the master transport equation (of Liouville type), a 6-dimensional 2nd order partial differential equation in configuration space of representative coordinates and momenta, which we will solve by well known Monte Carlo techniques. Although the calculations in this approach are much less intensive, these critically depend on the input (sources and sinks) provided by the reaction rates, diffusion coefficients and dynamical variables, obtained by MD and from other methods, including experiments.

Build a Device with a Nano Gap and Test Translocation.

Figure 43:
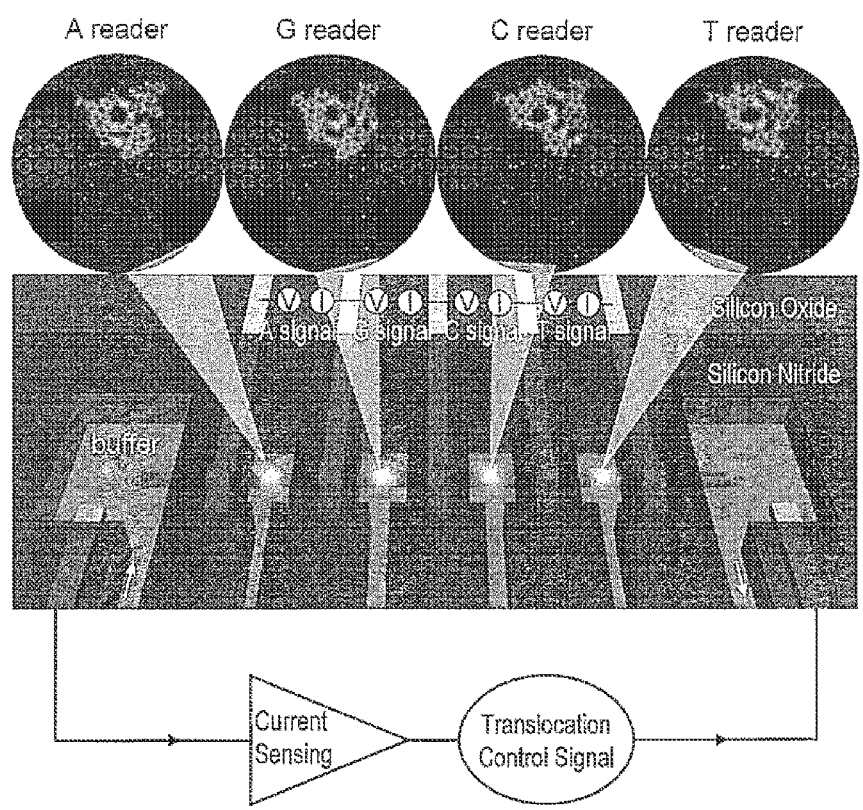
FIG. 43 shows a device of the present invention showing feedback circuitry for controlling translocation of ssDNA through the CNT.
Figure 44:
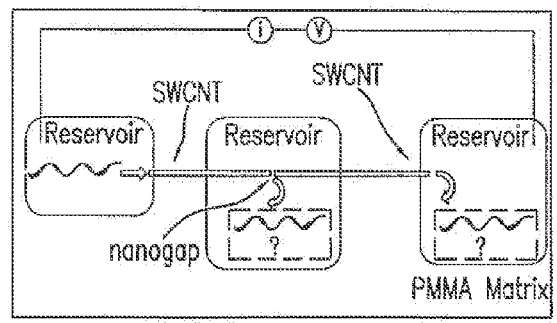
FIG. 44 provides a three well device for comparing translocation out of or across a small gap.
Figure 45:
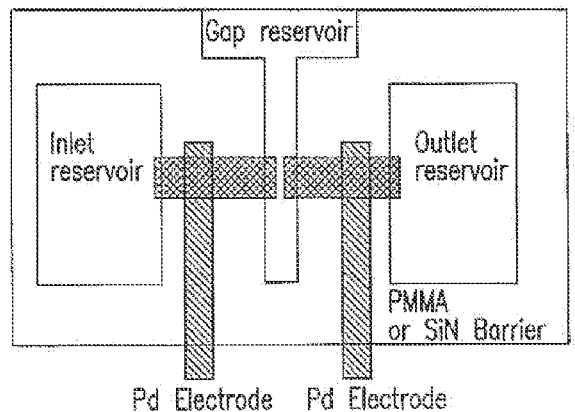
FIG. 45 provides a device with electrical contacts used to probe the effects of reading bias across the gap.

DNA is clearly capable of exiting a "tight" SWCNT, but what happens if another CNT is close by, as in the proposed reading gap? As DNA molecules approach the nanometer-size gap in the SWCNT, they have two possible destinies. They can either (a) move directly into the other half of the SWCNT, or (b) leave the nanogap and diffuse into the solution. We can read the DNA sequence with the "recognition molecules" in both cases, but translocation across the gap would enable sequential reads of all four bases on each molecule (FIG. 43). We will build the three-well device outlined in FIG. 44. In this device, a nanogap is cut in the SWCNT using e-beam lithography. DNA will be injected into the left reservoir and allowed to translocate through the SWCNTs. Solutions in the other two reservoirs will be collected and analyzed with qPCR to quantify the number of DNA copies translocated into each reservoir as a function of the electrophoretic driving field, $V_E$. Further control can be added by using a third reference electrode to control the potential of the middle reservoir. Finally, a device with electrical contacts (FIG. 45) will be used to probe the effects of the reading bias applied across the gap (a higher bias should enhance trans-gap translocation). These data will be used to refine our computer model of translocation, so that we can find optimal biases for both translocation and readout.

Active Translocation Control.

The positive current spikes characteristic of translocation through "tight" CNTs span 5 to 30 ms in measurements made to date. These signals appear to be a consequence of the cooperative emptying of the tubes, and so may be determined more by the tube itself than the length of the DNA. Whatever their origin, the signals are much longer than the 100 μs response of our measurement system (FIG. 35D). We will build a feedback-controlled bias source, designed to switch the bias across the tube to zero at a chosen interval after a translocation signal is detected. If the DNA remains stuck in the tube, we expect to see evidence of this in a current signal that differs from the background once the bias is restored. If we can do this, we should be able to detect signals as the same molecule is moved back and forth through the nanopore, much as has been done with a conventional nanopore. We will carry out a systematic study of signals as a function of DNA length, bias, CNT length and diameter and salt concentration. It may prove possible to detect a signal representative of the purine/pyrimidine content of various sequences if specific chemical interactions with the wall of the tube differ enough between different natural sequences. When combined with the theoretical simulations described above we hope to understand how to control the dwell time on each base, how to minimize "stutter" (the DNA goes backwards), how uniform (or otherwise) translocation speed is, and how to do multiple reads on the same molecule.

Example 6

A number of types of "universal reader" molecules are discussed above. These have in common the ability to form hydrogen bonds with all four bases, and to do so in a way that a tunnel gap will be spanned when a base in bonded by the same reagent on both surfaces. The use of the same reagent on both electrodes is an important simplification that can be achieved with the use of certain universal readers. A generic feature of these molecules is that they posses both hydrogen bond donors and acceptors, spaced in a way that allows them to form hydrogen bonds with multiple sites on the DNA bases. Thiobenzoic acid (see FIG. 58B) is a simple molecule which can act as a hydrogen bond donor and acceptor in aprotic solvents (i.e., organic solvent without free proteins). This is because the carboxylate residue remains protonated as shown in FIG. 58B. The OH group acts rather like a hydrogen bond donor and the doubly bonded oxygen is similar to a hydrogen bond acceptor so that these molecules are capable of quite strong pairing with each other. Monolayers of thiobenzoic acid were made on Au(111) surfaces, and their density, height and orientation was verified with STM imaging, FTIR and ellipsometry. Contact angle measurements showed the films to be highly hydrophilic in a humid atmosphere, confirming that the surface was terminated by the carboxylate residue. To make nucleosides soluble in an organic solvent (trichlorobenzene, TCB), the OH groups in the deoxyribose ring were functionalized with t-butyldimethylsilyl (TBDMS). This was performed for all four nucleosides and also 5-methyl cytidine. FIG. 58A shows the modified adenosine as an example.

Figure 59:
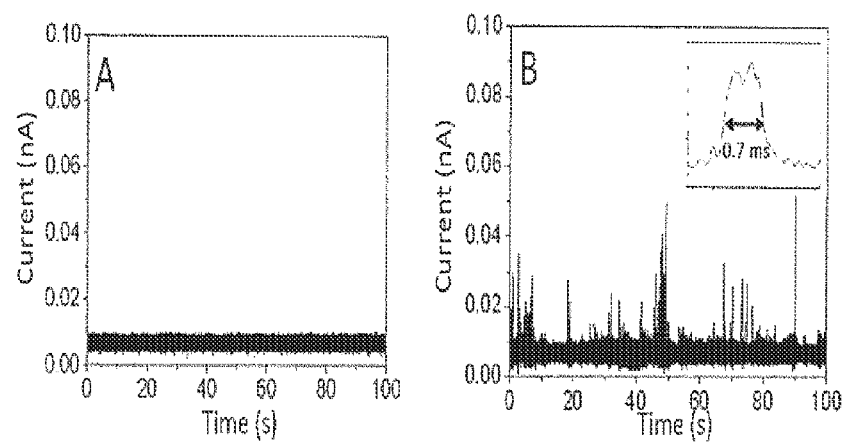
FIG. 59 provides the results of a study detailed in Example 6.
Figure 60:
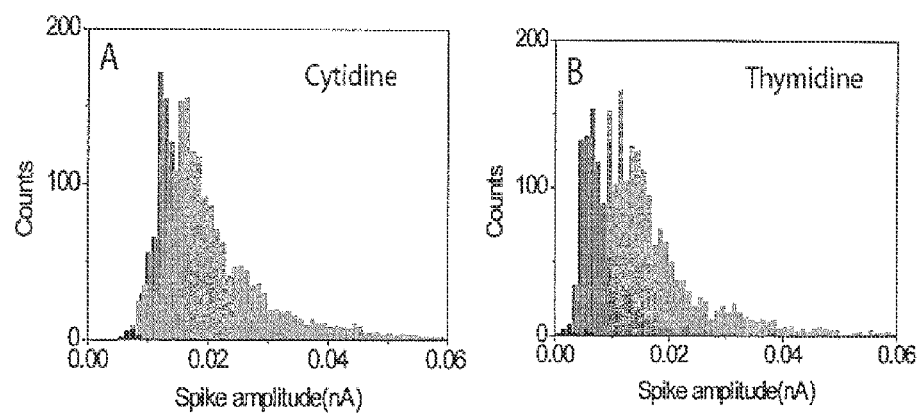
FIG. 60 is a histogram of current spike amplitudes as nucleosides pass through a tunnel gap. Dependence of mean current and the width of the distribution on the tunnel gap for (A) cytidine and (B) Thymidine. At $G_{bl}$=4 pS (black) there are very few reads. As $G_{bl}$ is increased from 12 pS (dark grey) to 20 pS (light grey) the reads move to higher values and the distribution broadens. The light grey background is what happens with no functionalization of probe and surface. The dark grey distributions are for the functionalization shown—in aprotic solvent COOH is one part H bond acceptor (=O) and one part donor (—OH). So this one very simple reagent forms H bonds with both bases to complete the circuit across the (now much larger) tunnel gap. There is no signal at all without nucleosides present in solution, and the dark grey distributions show that one can clearly distinguish C from T in single molecule reads with amazing fidelity on one read in one gap.

A gold probe was functionalized with thiobenzoic acid and a tunnel gap over a functionalized gold surface submerged in freshly distilled trichlorobenzene (TCB) in an STM was established. At high tunnel currents, signals were noisy, indicative of interactions between the benzoic acid residues on the probe and substrate. However, when the gap conductance was reduced below 100 pS, the signal became quiet (FIG. 59A shows data for a baseline conductance, $G_{BL}$, of 12 pS). When nucleosides were flowed into the liquid cell, sharp spikes appeared as shown in FIG. 59B. The distribution of spike heights depended upon the size of the tunnel gap, as might be expected, given the analysis of telegraph noise shown in FIG. 50. Data for cytidine and thymidine are presented in FIG. 60. At very large gaps ($G_{BL}$=4 pS) very few events are recorded. Many more are recorded at $G_{BL}$=12 pS. The number increases again as the gap 1s decreased to give $G_{BL}$=20 pS, but the width of the distribution increases substantially, again, in line with the trends displayed in FIG. 50.

Figure 61:
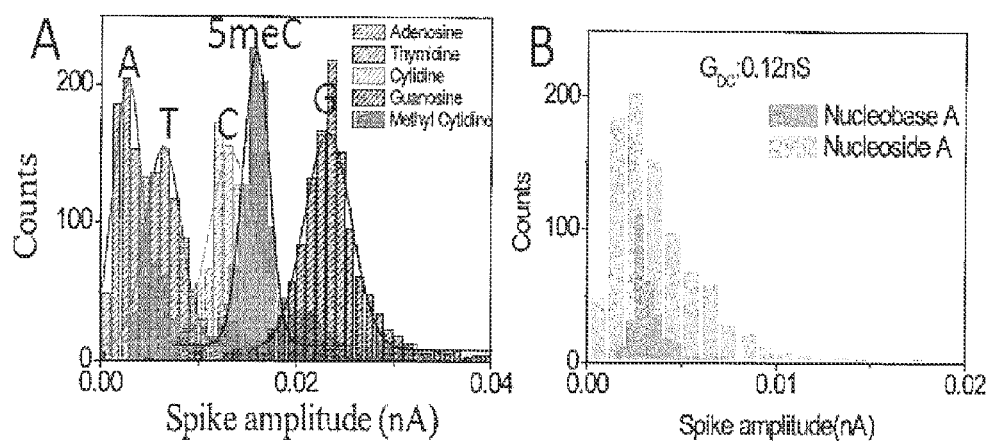
FIG. 61(a) provides spike height distributions for all four nucleosides and 5-methyl cytidine. (b) Blow up of the data for adenosine (light grey) with the distribution for adenine superimposed (dark grey) showing the reproducibility and demonstrating that interactions are dominated by the base.

Spike distributions for all four nucleosides and 5 methyl-cytidine are shown in FIG. 61A. It is clear that the nucleosides can be read with some degree of discrimination. A single tunneling read holds promise for recognizing all four nucleotides as well as 5 methyl-cytidine.

FIG. 61B superimposes data taken from adenine, superimposed on top of the distribution obtained from adenosine. The peaks are in the same position, showing that the base dominates the tunneling. However, the data for adenosine are substantially broader, suggesting that fluctuations involving the sugar ring contribute to the spread of the data.

Figure 62:
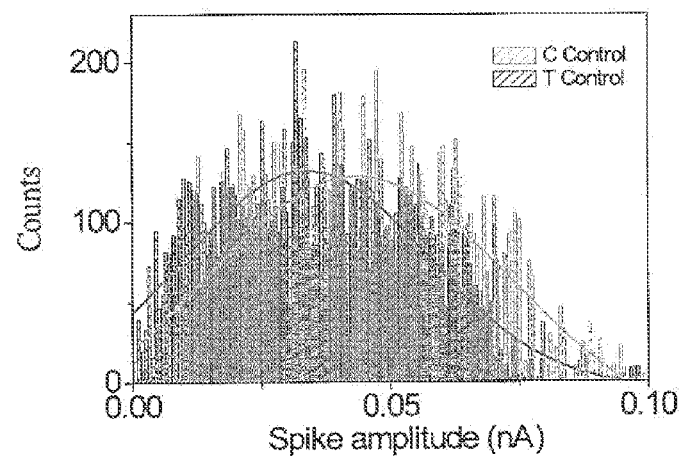
FIG. 62 shows tunnel current distribution without functionalized electrodes for thymidine (dark grey) and cytidine (light grey).

Finally, the degree of discrimination obtained here is much better than that theoretically predicted for tunneling through bases without functionalized electrodes. This point is demonstrated experimentally, with measurements of the spike distribution made with bare gold electrodes (and $G_{BL}$ increased to 40 pS to get a signal). The results are shown for cytidine and thymidine in FIG. 62.

The invention claimed is:

1. A molecular recognition chip configured to identify at least one portion of a target molecule, the chip comprising:
    a) a substrate;
    b) a first nanotube passing through at least a portion of the substrate, the first nanotube provided with a nanopore and configured and dimensioned to permit the translocation of a target molecule therethrough;
    c) a second nanotube supported by the substrate and disposed in a fixed relationship with respect to said first nanotube so as to form a first gap with the first nanotube; and
    d) an electrical circuit configured to detect an electrical current between the first and second nanotubes, upon passage of the target molecule past said gap;
    wherein the first nanotube comprises a first recognition element connected to an end thereof, the second nanotube comprises a second recognition element connected to a first end thereof, and wherein each of the first and second recognition elements further comprise a universal base reader.

2. The chip of claim 1 wherein the universal base reader is capable of recognizing different DNA bases and is also capable of forming a set of hydrogen bonds with a complex of a DNA base and the universal base reader.

3. The chip of claim 2 wherein the base reader comprises 4-(mercaptomethyl)-1H-imidazole-2-carboxamide.

4. The chip of claim 2 wherein the base reader comprises 5-(2-aminoethyl)-1H-imidazole-2-carboxamide.

5. The chip of claim 2 wherein the base reader comprises thiobenzoic acid.

6. The device of claim 5 wherein the universal base readers comprise 4-(mercaptomethyl)-1H-imidazole-2-carboxamide.

7. The device of claim 5 wherein the universal base readers comprise 5-(2-aminoethyl)-1H-imidazole-2-carboxamide.

8. The device of claim 7 wherein the molecular linker is functionalized with an anchoring group selected from the group consisting of amine, thiol, carboxylic acid, halogen, selenium, and hydroxyl.

9. The device of claim 5 wherein the universal base reader comprises thiobenzoic acid.

10. The device of claim 5 wherein the universal base readers comprise a conjugate of a planar n system with a functional group, amine, amide, nitro, carboxylic acid, and halogen, connected to a molecular linker or a conjugate of the functional group with a molecular linker.

11. The device of claim 1, wherein the universal base readers are selected, independently, from the group consisting of:

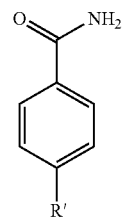

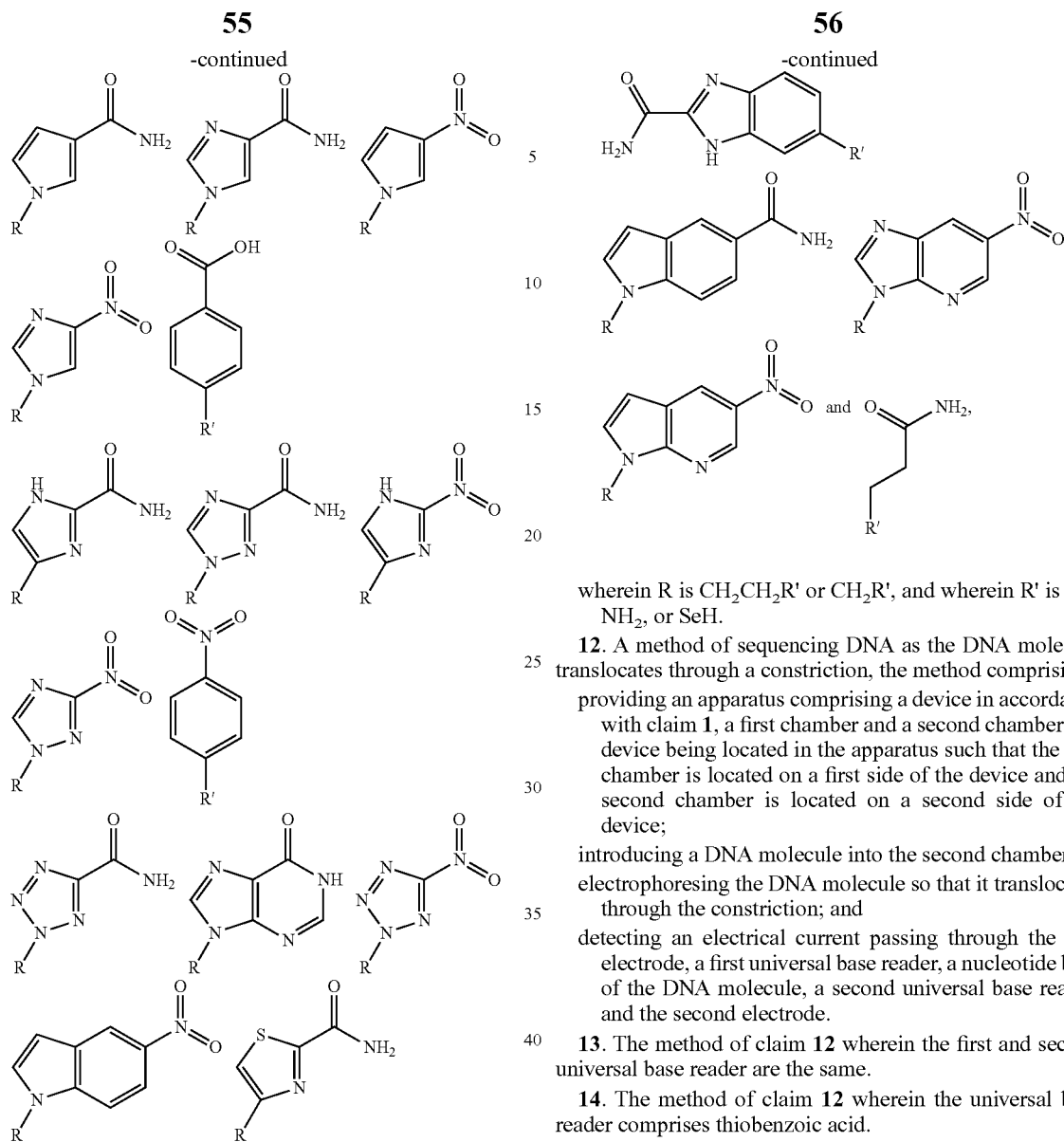

wherein R is CH$_2$CH$_2$R' or CH$_2$R', and wherein R' is SH, NH$_2$, or SeH.

12. A method of sequencing DNA as the DNA molecule translocates through a constriction, the method comprising:
providing an apparatus comprising a device in accordance with claim 1, a first chamber and a second chamber, the device being located in the apparatus such that the first chamber is located on a first side of the device and the second chamber is located on a second side of the device;
introducing a DNA molecule into the second chamber;
electrophoresing the DNA molecule so that it translocates through the constriction; and
detecting an electrical current passing through the first electrode, a first universal base reader, a nucleotide base of the DNA molecule, a second universal base reader, and the second electrode.

13. The method of claim 12 wherein the first and second universal base reader are the same.

14. The method of claim 12 wherein the universal base reader comprises thiobenzoic acid.

* * * * *